(12) United States Patent
Fleischmann et al.

(10) Patent No.: US 9,115,206 B2
(45) Date of Patent: Aug. 25, 2015

(54) NUCLEIC ACID EXPRESSION CONSTRUCT AND ITS USE AS A CELL PROLIFERATION MARKER

(75) Inventors: Bernd K. Fleischmann, Bonn (DE); Michael Hesse, Bonn (DE); Alexandra Raulf, Bonn (DE)

(73) Assignee: RHEINISCHE FRIEDRICH-WILHELMS-UNIVERSITAET BONN, Bonn (DE)

( * ) Notice: Subject to any disclaimer, the term of this patent is extended or adjusted under 35 U.S.C. 154(b) by 0 days.

(21) Appl. No.: 13/383,580

(22) PCT Filed: Jul. 15, 2010

(86) PCT No.: PCT/EP2010/060208
§ 371 (c)(1),
(2), (4) Date: Jan. 12, 2012

(87) PCT Pub. No.: WO2011/006962
PCT Pub. Date: Jan. 20, 2011

(65) Prior Publication Data
US 2012/0117668 A1    May 10, 2012

(30) Foreign Application Priority Data
Jul. 15, 2009    (EP) .................................... 09009233

(51) Int. Cl.
*C07K 14/47*    (2006.01)
*C12N 15/63*    (2006.01)

(52) U.S. Cl.
CPC ............ *C07K 14/4738* (2013.01); *C12N 15/63* (2013.01)

(58) Field of Classification Search
IPC .............................. C07K 14/4738; C12N 15/63
See application file for complete search history.

(56) References Cited

U.S. PATENT DOCUMENTS

| | | | |
|---|---|---|---|
| 7,235,401 B2* | 6/2007 | Pines et al. ................. | 435/320.1 |
| 2005/0112765 A1* | 5/2005 | Li et al. ........................ | 435/456 |
| 2006/0206950 A1* | 9/2006 | Kaelin, Jr. ..................... | 800/18 |
| 2006/0292694 A1* | 12/2006 | Clark et al. ................... | 435/370 |
| 2007/0238123 A1 | 10/2007 | Pines et al. | |
| 2010/0016408 A1* | 1/2010 | Pagano et al. ................ | 514/44 A |
| 2011/0135647 A1* | 6/2011 | Nakamura et al. ......... | 424/139.1 |

FOREIGN PATENT DOCUMENTS

WO    WO 03/031612 A    4/2003

OTHER PUBLICATIONS

Corish and Tyler-Smith. Protein Engineering 12(12):1035-1040, 1999.*
Mouse Anillin sequence. Printout from www.ncbi.nlm.nih.gov/nuccore/BC032164.1, printed Sep. 16, 2013, pp. 1-4.*
Hamanaka et al. Cell Growth and Differentiation 5:249-257,1994.*
NM_001285998.1. Printout from PubMed. http://www.ncbi.nlm.nih.gov/nuccore/NM_001285998.1. pp. 1-5, printed Dec. 12, 2014.*
Tsoporis et al. Experimental Cell Research 303:471-481, 2003.*
A. E. Ross et al.: "Overlapping signals for protein degradation and nuclear localization define a role for intrinsic RAG-2 nuclear uptake in dividing cells", Molecular and Cellular Biology, vol. 23, No. 15, pp. 5308-5319 (Aug. 2003).
C. Mateus et al.: "Destabilized Green Fluorescent Protein for Monitoring Dynamic Changes in Yeast Gene Expression with Flow Cytometry", Yeast, John Wiley & Sons Ltd, GB, vol. 16, No. 14, pp. 1313-1323, (Jan. 1, 2000).
P. Steigemann et al.: "Cytokinetic abscission: cellular dynamics at the midbody", Trends in Cell Biology, vol. 19, No. 11, pp. 606-616 (Nov. 2009).
Y. N. Tallini et al.: "c-kit expression identifies cardiovascular presursors in the neonatal heart", Proceedings of the National Academy of Sciences of the United States of America, vol. 106, No. 6, pp. 1803-1813 (Feb. 2009).
S. F. Altschul et al.: "Basic Local Alignment Search Tool", J. Mol. Biol. 215, pp. 403-410 (1990).
A. N. Alexopoulou et al.: "The CMV early enhancer/chicken β actin (CAG) promoter can be used to drive transgene expression during the differentiation of murine embryonic stem cells into vascular progenitors", BMC Cell Biology, 9:2, pp. 1-11 (2008).
K. A. Becker et al.: "Self-Renewal of Human Embryonic Stem Cells is Supported by a Shortened G1 Cell Cycle Phase", Journal of Cellular Physiology 209, pp. 883-893 (2006).
A. P. Beltrami et al.: "Evidence that Human Cardiac Myocytes Divide After Myocardial Infarction", The New England Journal of Medicine, vol. 344, No. 23, pp. 1750-1757 (Jun. 7, 2001).
J. J. Breunig et al.: "Everything that Glitters Isnt't Gold: A Critical Review of Postnatal Neural Precursor Analyses", Cell Stem Cell 1, pp. 612-627 (Dec. 2007).
W. Y. Brodsky et al.: "Cell Polyploidy: Its Relation to Tissue Growth and Function", Int. Rev. Cytol. 50, pp. 275-332 (1977).
J. C. Cross: "How to Make a Placenta: Mechanisms of Trophoblast Cell Differentiation in Mice—A Review", Placenta, vol. 26 Supplement A, Trophoblast Research, vol. 19, pp. S3-S9 (2005).
P. P. D' Avino: "How to scaffold the contractile ring for a safe cytokinesis—lessons from Anillin-related proteins", Journal of Cell Science 122, pp. 1071-1079 (2009).
V. Dubreuil et al.: "Midbody and primary cilium of neural progenitors release extracellular membrane particles enriched in the stem cell marker prominin-1", The Journal of Cell Biology, vol. 176, No. 4, pp. 483-495 (2007).
H. P. Easwaran et al.: "Cell Cycle Markers for Live Cell Analyses", Cell Cycle 4:3, pp. 453-455 (Mar. 2005).
E. Endl et al.: "The Ki-67 Protein: Fascinating Forms and an Unknown Function", Experimental Cell Research 257, pp. 231-237 (2000).
C. M. Field et al.: "Anillin, a Contractile Ring Protein That Cycles from the Nucleus to the Cell Cortex", The Journal of Cell Biology, vol. 131, No. 1, pp. 165-178 (Oct. 1995).

(Continued)

*Primary Examiner* — Marcia S Noble
(74) *Attorney, Agent, or Firm* — Norman B. Thot

(57) ABSTRACT

A nucleic acid expression construct which encodes a fusion protein includes a reporter protein and a protein with a wild-type destruction signal. A sequence encoding the fusion protein is operably linked to a non-endogenous promoter. The fusion protein localizes during a cell cycle progression to subcellular structures selected from a cell cortex, a contractile ring, and a midbody.

14 Claims, 19 Drawing Sheets

(56) References Cited

OTHER PUBLICATIONS

A. C. Fluckiger et al.: "Cell cycle features of primate embryonic stem cells", Stem Cells, 24(3), pp. 547-556 (Mar. 2006).

S. H. L. George et al: "Developmental and adult phenotyping directly from mutant embryonic stem cells", PNAS, vol. 104, No. 11, pp. 4455-4460 (Mar. 13, 2007).

C. Gieffers et al.: "Expression of the CDH1-associated form of the anaphase-promoting complex in postmitotic neurons", Proc. Natl. Acad. Sci., vol. 96, pp. 11317-11322 (Sep. 1999).

B. Hein et al.: "Stimulated emission depletion (STED) nanoscopy of a fluorescent protein-labeled organelle inside a living cell", PNAS, vol. 105, No. 38, pp. 14271-14276 (Sep. 23, 2008).

P. C. H. Hsieh et al.: "Evidence from a genetic fate-mapping study that stem cells refresh adult mammlian cardiomyocytes after injury", Nat. Med., 13(8) pp. 970-974 (Aug. 2007).

J. B. Kim et al.: "Direct reprogramming of human neural stem cells by OCT4", Nature, vol. 461, pp. 649-654 (Oct. 1, 2009).

E. Kolossov et al.: "Engraftment of engineered ES cell-derived cardiomyocytes but not BM cells restores contractile function to the infarcted myocardium", JEM, vol. 203, No. 10, pp. 2315-2327 (Oct. 2, 2006).

Y. Kosodo et al.: "Cytokinesis of neuroepithelial cells can divide their basal process before anaphase", The EMBO Journal, vol. 27, No. 3, pp. 3151-3163 (2008).

M. Li et al.: "The function of APC/$C^{Cdh1}$ in cell cycle and beyond", Cell Division 4:2, pp. 1-7 (2009).

P. C. Meckert et al.: "Endomitosis and polyploidization of myocardial cells in the periphery of human acuted myocardial infarction", Cardiovascular Research 67, pp. 116-123 (2005).

S. Munakata et al.: "Effect of fixation time and microwave oven heating time on retrieval of the Ki-67 antigen from paraffin-embedded tissue", Journal of Histochemistry & Cytochemistry, vol. 41, No. 8, pp. 1241-1246 (1993).

A. Nagy et al.: "Derivation of completely cell culture-derived mice from early-passage embryonic stem cells", Proc. Natl. Acad. Sci., vol. 90, pp. 8424-8428 (Sep. 1993).

L. Naldini: "Lentiviruses as gene transfer agents for delivery to non-dividing cells", Current Opinion in Biotechnology, 9, pp. 457-463, (1998).

P. Nurse: "A Long Twentieth Century of the Cell Cycle and Beyond", Cell, vol. 100, pp. 71-78 (Jan. 7, 2000).

M. Okabe et al.: "Green mice' as a source of ubiquitous green cells", FEBS Letters 407, pp. 313-319 (1997).

K. B. S. Pasumarthi et al.: "Cardiomyocyte Cell Cycle Regulation", Circulation Research, 90, pp. 1044-1054 (2002).

W. R. Pearson et al.: "Improved tools for biological sequence comparison", Proc. Natl. Acad. Sci., vol. 85, pp. 2444-2448 (Apr. 1988).

A. Pfeifer et al.: "Transgenesis by lentiviral vectors: Lack of gene silencing in mammalian embryonic stem cells and preimplantation embryos", PNAS, vol. 99, No. 4, pp. 2140-2145 (Feb. 19, 2002).

C. Pohl et al.: "Final Stages of Cytokinesis and Midbody Ring Formation Are Controlled by BRUCE", Cell, 132, pp. 832-845 (Mar. 7, 2008).

B. A. Rabinovich et al.: "Visualizing fewer than 10 mouse T cells with an enhanced firefly luciferase in immunocompetent mouse models of cancer", PNAS, vol. 105, No. 38, pp. 14342-14346 (Sep. 23, 2008).

W. Roell et al.: "Cellular Cardiomyoplasty in a Transgenic Mouse Model", Transplantation, vol. 73, No. 3, pp. 462-482 (Feb. 15, 2002).

A. Sakaue-Sawano et al.: "Visualizing Spatiotemporal Dynamics of Multicellular Cell-Cycle Progression", Cell, 132, pp. 487-498 (Feb. 8, 2008).

M. H. Soonpaa et al.: "Cardiomyocyte DNA synthesis an binucleation during murine development", Am. J. Phys. 271: H2183-H2189 (1996).

M. H. Soonpaa et al.: "Survey of Studies Examining Mammalian Cardiomyocyte DNA Synthesis", Circulation Research 83, pp. 15-26 (1998).

Z. Storchova et al.: "From Polyploidy to Aneuploidy, Genome Instability and Cancer", Nature Reviews, Molecular Cell Biology, vol. 5, pp. 45-54 (Jan. 2004).

K. Takahashi et al.: "Induction of Pluripotent Stem Cells from Mouse Embryonic and Adult Fibroblast Cultures by Defined Factors", Cell 126, pp. 663-676 (Aug. 25, 2006).

J. A. Thomson et al.: "Embryonic Stem Cell Lines Derived from Human Blastocysts", Science, vol. 282, pp. 1145-1147 (Nov. 6, 1998).

J. J. Tyson et al.: "Temporal Organization of the Cell Cycle", Curr. Biol, 18, pp. R759-R768 (Sep. 9, 2008).

A. Ventura et al.: "Cre-Iox-regulated conditional RNA interference from transgenes", PNAS, vol. 101, No. 28, pp. 10380-10385 (Jul. 13, 2004).

K. Vintersten et al.: "Mouse in Red: Red Fluorescent Protein Expression in Mouse ES Cells, Embryos, and Adult Animals", Genesis, 40, pp. 241-246 (2004).

J. I. Virag et al.: "Myofibroblast and Endothelial Cell Proliferation during Murine Myocardial Infarct Repair", American Journal of Pathology, vol. 163, No. 6, pp. 2433-2440 (Dec. 2003).

J. White et al.: "Cell Cycle Controls of Embryonic Stem Cells", Stem Cell Reviews, pp. 131-138 (2005).

A.M. Wobus et al.: "Pluripotent mouse embryonic stem cells are able to differentiate into cardiomyocytes expressing chronotropic responses to adrenergic and cholinergic agents and $Ca^{2+}$ channel blockers", Differentiation, 48, pp. 173-182 (1991).

H. Zaehres et al.: "Induction of pluripotency in human cord blood unrestricted somatic stem cells", Experimental Hematology, 38 pp. 809-818 (2010).

W. M. Zhao et al.: "Anillin Is a Substrate of Anaphase-promoting Complex/Cyclosome (APC/C) That Controls Spatial Contractility of Myosin during Late Cytokinesis", The Journal of Biological Chemistry, vol. 280, No. 39, pp. 33516-33524 (Sep. 30, 2005).

E. V. Zybina et al.: "Polytene Chromosomes in Mammalian Cells", International Review of Cytology, vol. 165, pp. 53-119 (1996).

G. W. Herget et al.: "DNA content, ploidy level and number of nuclei in the human heart after myocardial infarction", Cardiovascular Research 36, pp. 45-51 (1997).

J. J. Tasto et al.: "An anillin homologue, Mid2p, acts during fission yeast cytokinesis to organize the septin ring and promote cell separation", The Journal of Cell Biology, vol. 160, No. 7, pp. 1093-1103 (Mar. 31, 2003).

K. Oegema et al.: "Functional Analysis of a Human Homologue of the *Drosophila* Actin Binding Protein Anillin Suggests a Role in Cytokinesis", The Journal of Cell Biology, vol. 150, No. 3, pp. 539-551 (Aug. 7, 2000).

\* cited by examiner

Fig. 1
A
B
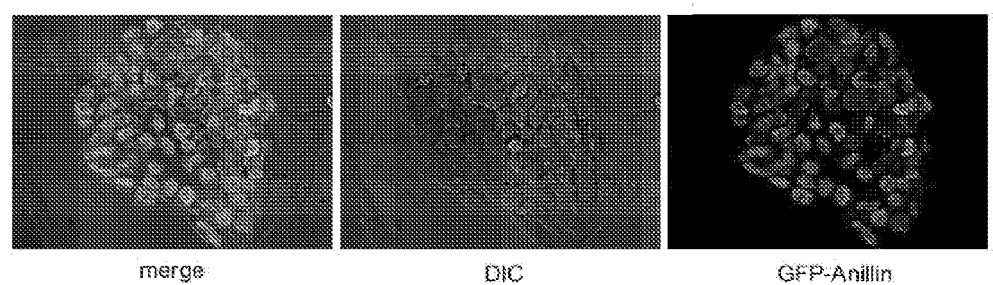
C
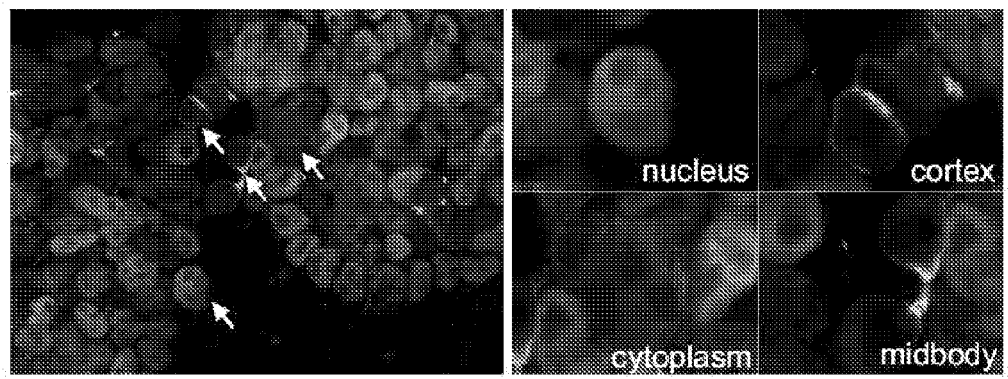
D
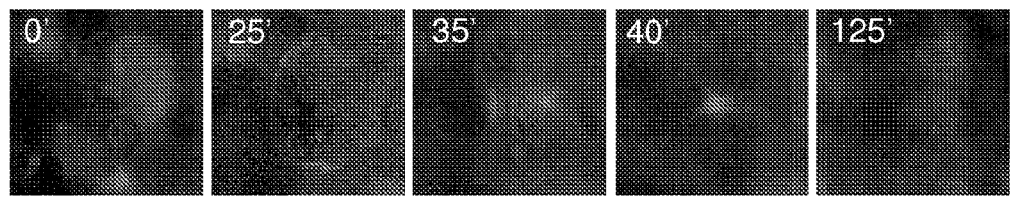

Fig. 2
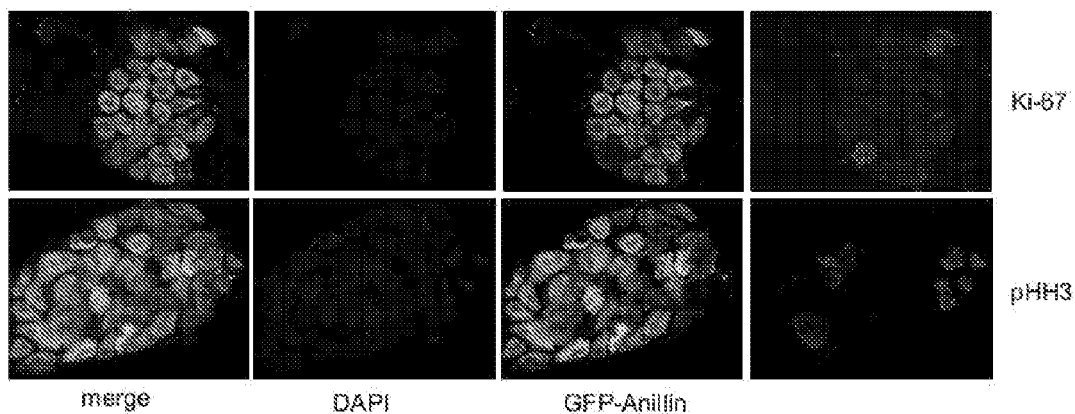
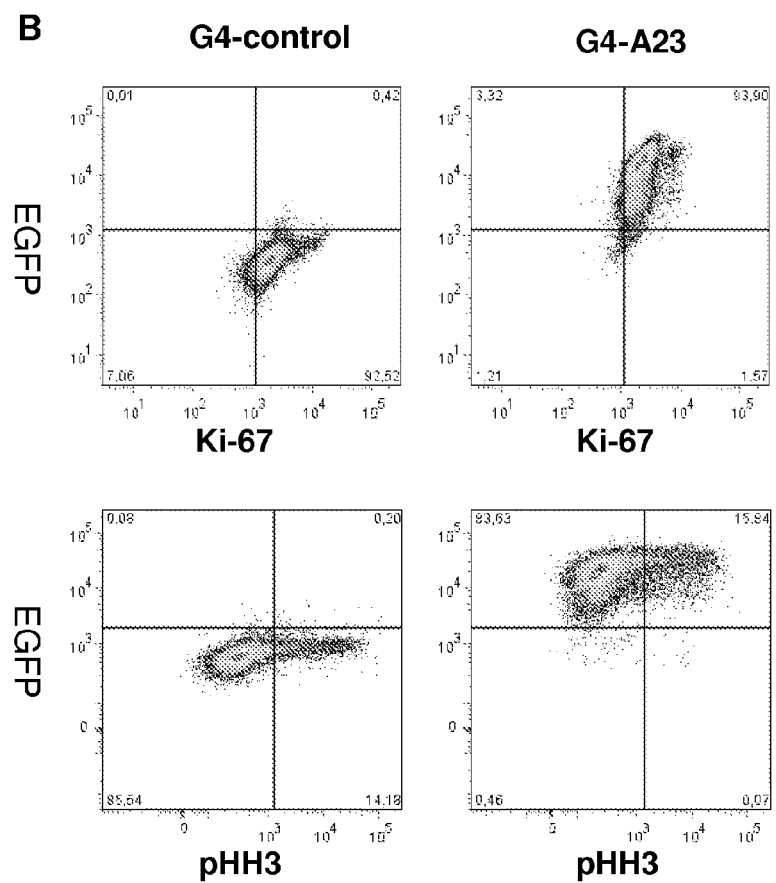

Fig. 3
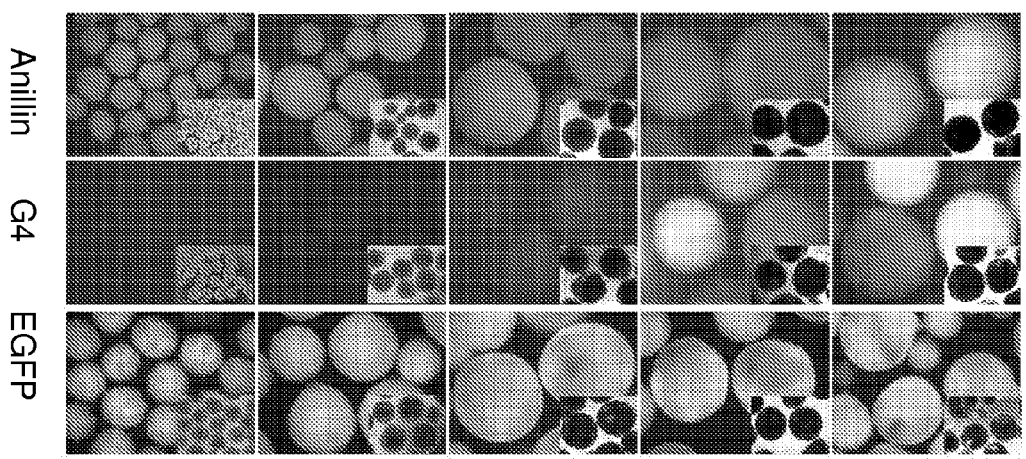
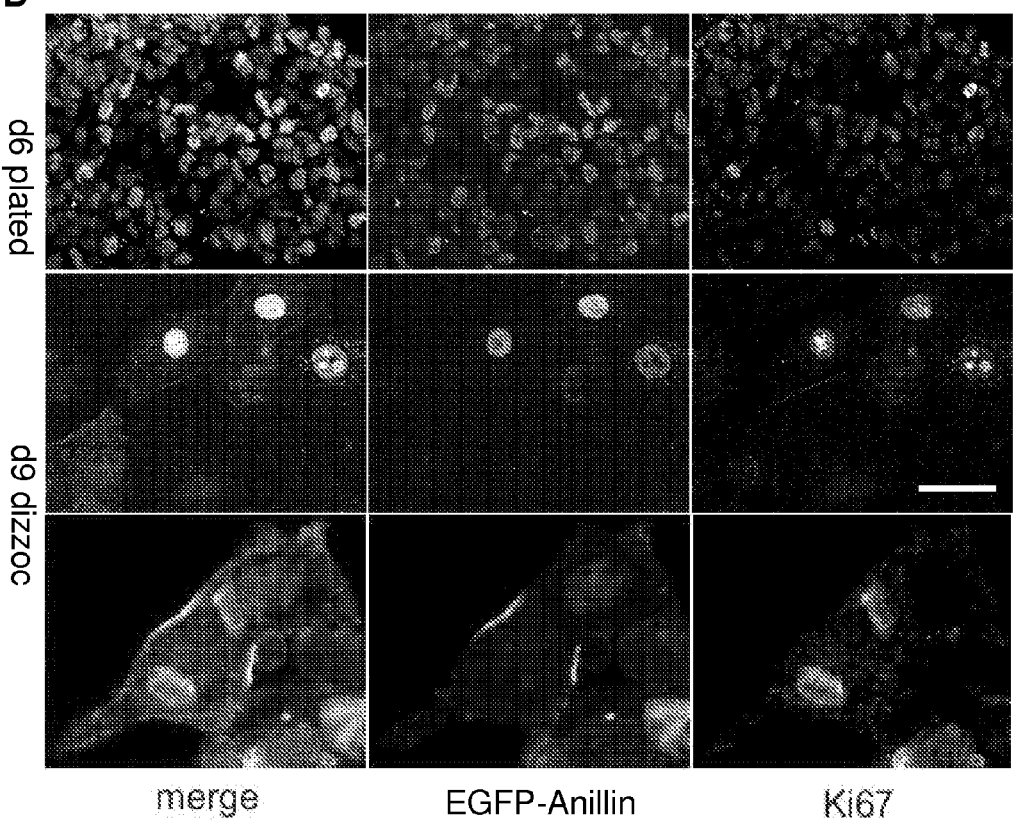

Fig. 5
A
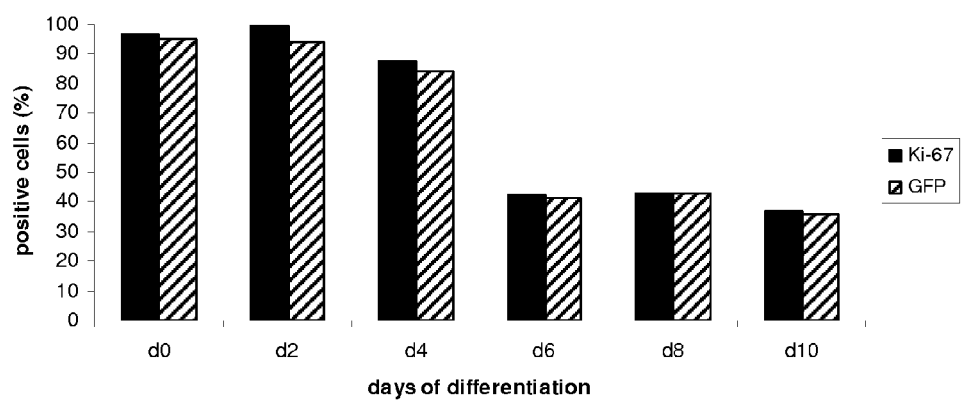
B
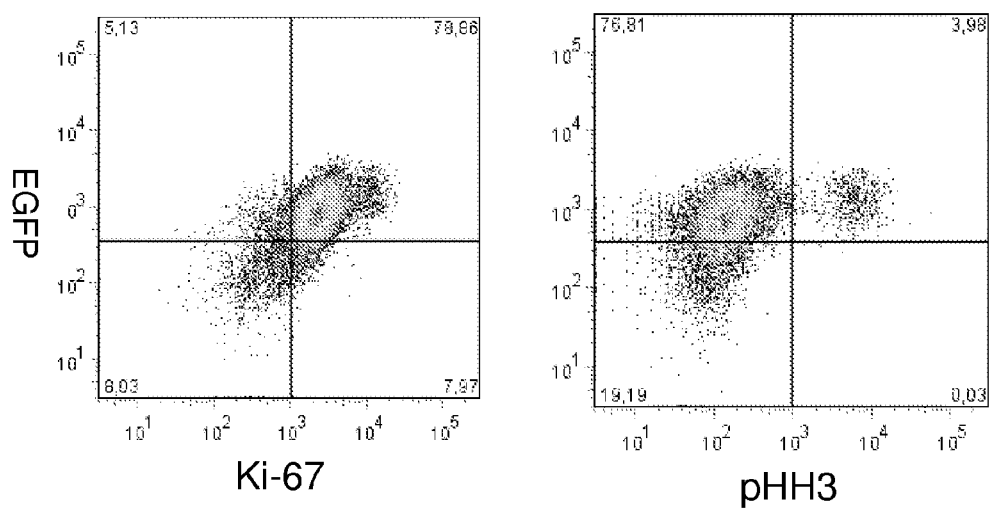

Fig. 7
A
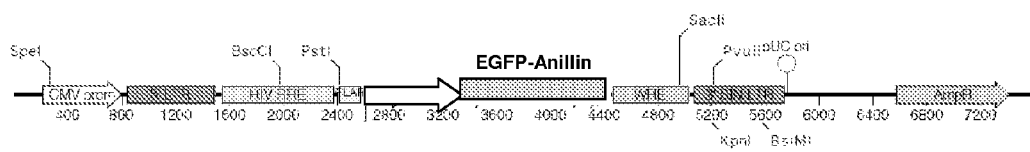
B
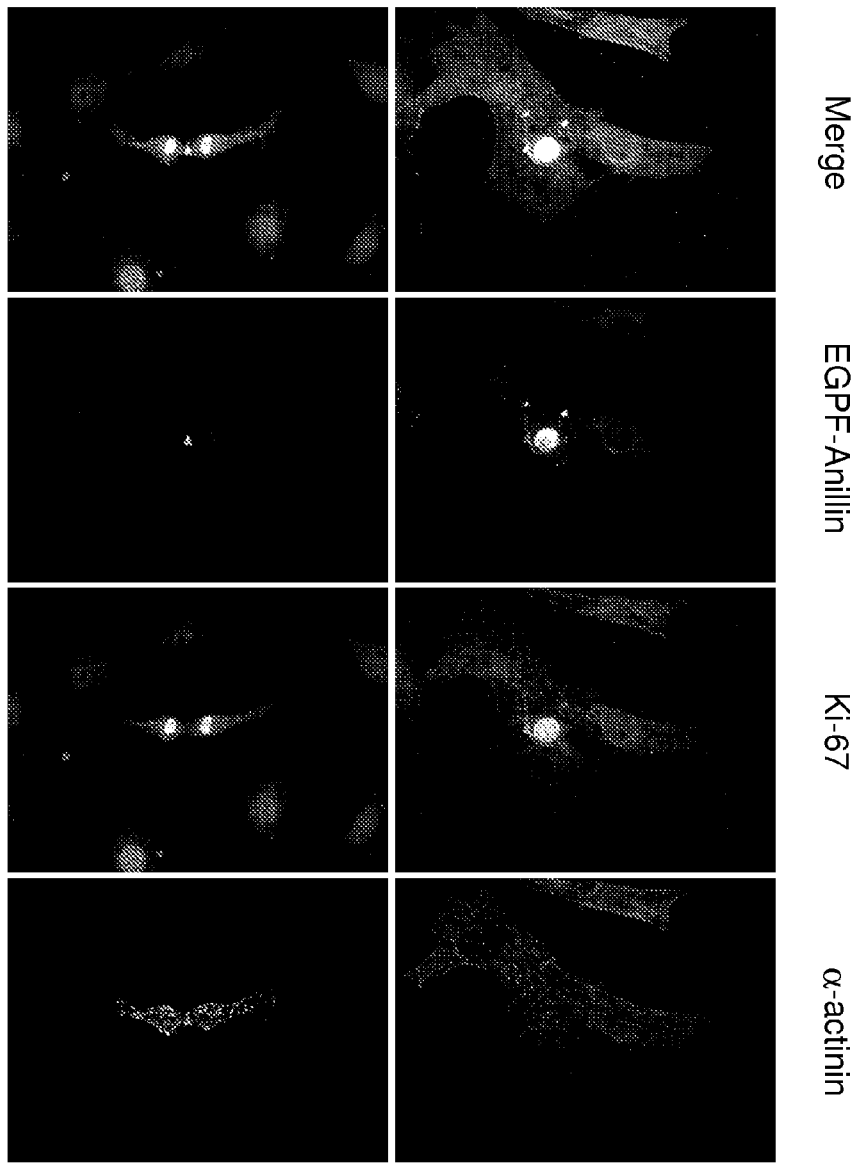

Fig. 8
A
B
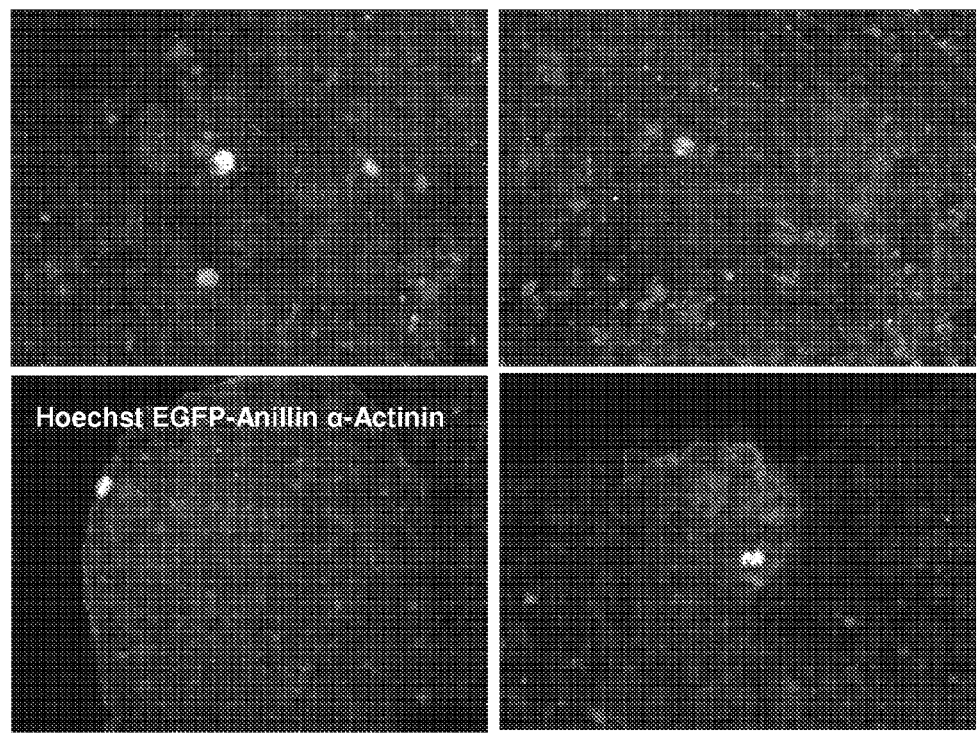

Fig. 9
A
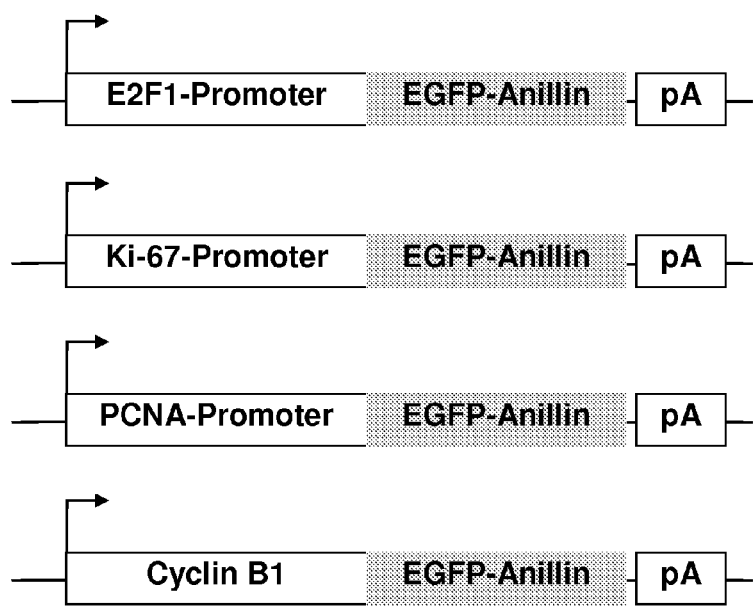
B
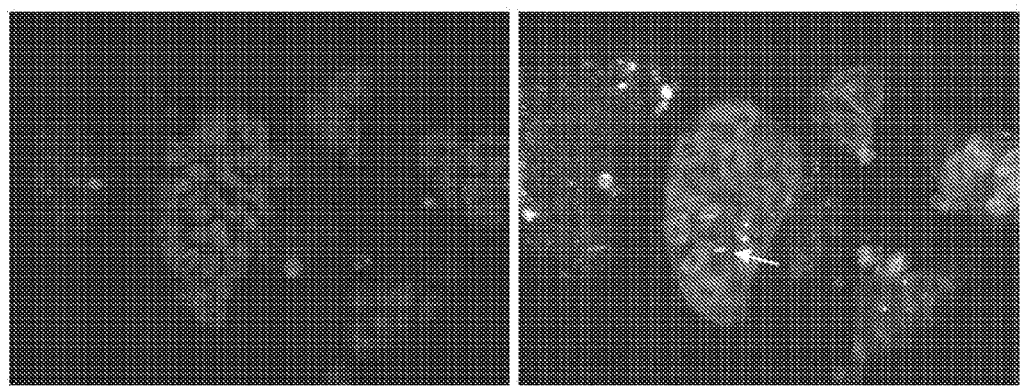

Fig. 10

SEQ ID NO.: 1

```
   1 TAGTTATTCG ACATTGATTA TTGACTAGTT ATTAATAGTA ATCAATTACG
  51 GGGTCATTAG TTCATAGCCC ATATATGGAG TTCCGCGTTA CATAACTTAC
 101 GGTAAATGGC CCGCCTGGCT GACCGCCCAA CGACCCCCGC CCATTGACGT
 151 CAATAATGAC GTATGTTCCC ATAGTAACGC CAATAGGGAC TTTCCATTGA
 201 CGTCAATGGG TGGAGTATTT ACGGTAAACT GCCCACTTGG CAGTACATCA
 251 AGTGTATCAT ATGCCAAGTA CGCCCCCTAT TGACGTCAAT GACGGTAAAT
 301 GGCCCGCCTG GCATTATGCC CAGTACATGA CCTTATGGGA CTTTCCTACT
 351 TGGCAGTACA TCTACGTATT AGTCATCGCT ATTACCATGG TCGAGGTGAG
 401 CCCCACGTTC TGCTTCACTC TCCCCATCTC CCCCCCCTCC CCACCCCCAA
 451 TTTTGTATTT ATTTATTTTT TAATTATTTT GTGCAGCGAT GGGGGCGGGG
 501 GGGGGGGGGG GGCGCGCGCC AGGCGGGGCG GGGCGGGGCG AGGGGCGGGG
 551 CGGGGCGAGG CGGAGAGGTG CGGCGGCAGC CAATCAGAGC GGCGCGCTCC
 601 GAAAGTTTCC TTTTATGGCG AGGCGGCGGC GGCGGCGGCC CTATAAAAAG
 651 CGAAGCGCGC GGCGGGCGGG AGTCGCTGCG TTGCCTTCGC CCCGTGCCCC
 701 GCTCCGCGCC GCCTCGCGCC GCCCGCCCCG GCTCTGACTG ACCGCGTTAC
 751 TCCCACAGGT GAGCGGGCGG GACGGCCCTT CTCCTCCGGG CTGTAATTAG
 801 CGCTTGGTTT AATGACGGCT CGTTTCTTTT CTGTGGCTGC GTGAAAGCCT
 851 TAAAGGGCTC CGGGAGGGCC CTTTGTGCGG GGGGAGCGG CTCGGGGGGT
 901 GCGTGCGTGT GTGTGTGCGT GGGGAGCGCC GCGTGCGGCC CGCGCTGCCC
 951 GGCGGCTGTG AGCGCTGCGG GCGCGGCGCG GGCTTTGTG CGCTCCGCGT
1001 GTGCGCGAGG GGAGCGCGGC CGGGGGCGGT GCCCCGCGGT GCGGGGGGGC
1051 TGCGAGGGGA ACAAAGGCTG CGTGCGGGGT GTGTGCGTGG GGGGTGAGC
1101 AGGGGGTGTG GGCGCGGCGG TCGGGCTGTA ACCCCCCCCT GCACCCCCCT
1151 CCCCGAGTTG CTGAGCACGG CCCGGCTTCG GGTGCGGGGC TCCGTACGGG
1201 GCGTGGCGCG GGGCTCGCCG TGCCGGGCGG GGGGTGGCGG CAGGTGGGGG
1251 TGCCGGGCGG GGCGGGGCCG CCTCGGGCCG GGGAGGGCTC GGGGGAGGGG
1301 CGCGGCGGCC CCCGGAGCGC CGGCGGCTGT CGAGGCGCGG CGAGCCGCAG
1351 CCATTGCCTT TTATGGTAAT CGTGCGAGAG GGCGCAGGGA CTTCCTTTGT
1401 CCCAAATCTG TGCGGAGCCG AAATCTGGGA GGCGCCGCCG CACCCCCTCT
1451 AGCGGGCGCG GGCGAAGCG GTGCGGCGCC GGCAGGAAGG AAATGGGCGG
1501 GGAGGGCCTT CGTGCGTCGC CGCGCCGCCG TCCCCTTCTC CCTCTCCAGC
1551 CTCGGGGCTG TCCGCGGGGG GACGGCTGCC TTCGGGGGGG ACGGGGCAGG
1601 GCGGGGTTCG GCTTCTGGCG TGTGACCGGC GGCTCTAGAG CCTCTGCTAA
1651 CCATGTTCAT GCCTTCTTCT TTTTCCTACA GCTCCTGGGC AACGTGCTGG
1701 TTATTGTGCT GTCTCATCAT TTTGGCAAAG AATTGCCCGG TCGCCACCAT
1751 GGTGAGCAAG GGCGAGGAGC TGTTCACCGG GGTGGTGCCC ATCCTGGTCG
1801 AGCTGGACGG CGACGTAAAC GGCCACAAGT TCAGCGTGTC CGGCGAGGGC
1851 GAGGGCGATG CCACCTACGG CAAGCTGACC CTGAAGTTCA TCTGCACCAC
1901 CGGCAAGCTG CCCGTGCCCT GGCCCACCCT CGTGACCACC CTGACCTACG
1951 GCGTGCAGTG CTTCAGCCGC TACCCCGACC ACATGAAGCA GCACGACTTC
2001 TTCAAGTCCG CCATGCCCGA AGGCTACGTC CAGGAGCGCA CCATCTTCTT
2051 CAAGGACGAC GGCAACTACA AGACCCGCGC CGAGGTGAAG TTCGAGGGCG
2101 ACACCCTGGT GAACCGCATC GAGCTGAAGG GCATCGACTT CAAGGAGGAC
2151 GGCAACATCC TGGGGCACAA GCTGGAGTAC AACTACAACA GCCACAACGT
2201 CTATATCATG GCCGACAAGC AGAAGAACGG CATCAAGGTG AACTTCAAGA
2251 TCCGCCACAA CATCGAGGAC GGCAGCGTGC AGCTCGCCGA CCACTACCAG
2301 CAGAACACCC CCATCGGCGA CGGCCCCGTG CTGCTGCCCG ACAACCACTA
2351 CCTGAGCACC CAGTCCGCCC TGAGCAAAGA CCCCAACGAG AAGCGCGATC
2401 ACATGGTCCT GCTGGAGTTC GTGACCGCCG CCGGGATCAC TCTCGGCATG
```

Fig. 10 (Continued I)

```
2451 GACGAGCTGT ACAAGTCCGG ACTCAGATCC GACCCGTTTA CCGAGAAGTT
2501 GCTAGAACGA ACTCGTGCCA GACGAGAGAA TCTTCAGAGA AAAATGGCTG
2551 AGAGGCCTAC GGCAGTAGCG AGATCTGCCC CGCATGCGAA GAGAGGCAGA
2601 GAGCCACTTT CAGAAGCAAG TAATCAGCAG CAGCCCCTAC CAGGGGGCGA
2651 AGAAAAATCT TGTACAAAAC CATCACCATC AAAAAAACGT TGTTCTGACA
2701 AAATTGAAGT GGGAGCTCCG GACTTAGAAA ATACAGAACC TATTGATGTT
2751 GCAAAGCCCT GTTCTCCGAT GCCTGCACCC CGGCAGGCGA AGCCCCCAGC
2801 ACCAGCTGCC ATCAGCGAGT CTGTGGCTGC CCCAGCAGCC CTGCTCAGCG
2851 CGGACAGAGG GCTGAACTCA GGATCCGAAG CATCTGCAAC CTCCTCAGTT
2901 AAAACTCGAA TGCAAAGGCT TGCTGAGCAG CGGCGCCATT GGGATAGTGA
2951 TCTCACAGAT GATGTATCAG AAAGTTCATA CTTTGCACCA GTGCCAACTG
3001 AGGACAAGGC TGCCTCACCT TCTAAGCCAC CCATTTCAAA TGCCTCAGCT
3051 ACTCCAGTTG GGAGAAGGGG CCGTCTGGCC AACCTTGCTG CAACGATTTG
3101 CTCCTGGGAA GATGATGTAA GCCACTCATC TGCAAAGCAA AATAGTGTGC
3151 AAGAACAGCC TGGTACCGCT TGTTTATCCA AATCTTCCTC TGCAAGTGGA
3201 GCATCTGCTA GCATCAATAG CAGCAGTGTT CAGCAGGAAG CTACATGCTG
3251 TTCCCCAAGG GACGGCAATG CCTCTGTCAG GAAAGACCCA TCTTCAAATG
3301 CTGCCCATGG ACCTTTGCTT AGCGCCTCAG TGTCCAGCTC TGTGAAAGCG
3351 TCTTCCCCTG TGACAGCTGC TACCTTCATC ACTGAAAACC GTGAGGCACA
3401 AAATCCTGAG CTACTTCACA AAACTGCTAG TCCTCTGAAA ACAGAGGCGC
3451 GGAAACCATG TGAGAAGCCA ACTTTGTCCC AGGGAGCTCA GCCCAAAGAG
3501 GAGGCTAACA GAGAAGTTTG TCTACAGTCA CAATCCAAGG ACAAACTTGC
3551 AACACCAGGA GGAAGAGGAA TTAACCCTTT CCTGGAACGC TTTGGAGAGC
3601 GTTGTCAAGA ACACAGTAAA GAAAGTCCGT CTTATAGAGC ATCTCATAAA
3651 ACCCCAAATA TCACTCCAAA TACAAAAGCC ATCCAGGAAA GATTATTCAA
3701 ACAAAACACA TGCTCGTCTA CTACCCATTT AGCACAGCAG CTCAAACAGG
3751 AACGTGAAAA AGAACTGGCA TGTCTTCGTG GTCGACTTGA CAAGGGCAAT
3801 TTATGGAGTG CAGAAAAGAA TGAAAAGTCA AGAAGCAAGC ATCTAGAAAC
3851 CAAACAGGAA GTTCACTGTC AGAACACTCC ACTCAAGAAA CATCAAACTG
3901 TCGCAAGCAC CCCATTGACT TCTGTAACAG ATAAGGTGGC TGAAAATGAA
3951 CCAGCAGTGA AGCTTTCTAG CACAGAGCCT GCAGGTTCCA CTGAAAGCGA
4001 AATGACAAAG TCCAGCCCTT TGAAAATCAC GTTGTTTTTA GAAGAAGAAA
4051 AATCCTTAAA AGTAGCATCA GACCTGGAGG TTGAGCAGAA CACTGAAGCA
4101 GTGCGTGAGG TTGAGATGAG TGTGGACGAT GAGGACATCA ATAGCTCCAG
4151 AGTCATTAAC GACATCTTCA GTGACGTCCT AGAGGAAGGG GAGCTGGATG
4201 TGGAAAAGAG CCAAGAGGAG ATGGACCAAG TGGGAGCAGA AAACAGTGAG
4251 GAGCAGGAAG ATGCGCTCAA TATCTCTTCA ATGTCTTTAC TTGCTCCGCT
4301 AGCTCAGACG GTCGGTGTGG TGAGCCTAGA GAATGTAATT TCTTCACCTC
4351 CGTCGGAATT GAGAGACTCT AACCTAAGCG CTGCAAGTCC TAAGCCCGGG
4401 AAATTCCAGA GAACCCGCGT CCCTCGCGCC GAATCTGCCG ATAGCCTCGG
4451 TTCTGAGGAC CGGGACCTTC TCTATAGCAT TGATGCATAT AGGTCTCAAA
4501 GATTCAAAGA AACAGAACGC CCTTCCATAA AGCAAGTGAT TGTTCGAAAG
4551 GAAGATGTTA CTTCAAAGTT GGGTGAAAAG AAAAACGTAT TTTCTGGTCA
4601 AGTTAATATC AAACAAAAAA TGCAGGAGCT CAATAATGAC ATAAATTTGC
4651 AGCAGACAGT GATCTATCAG GCCAGTCAGG CTCTCAACTG CTGTGTGGAT
4701 GAAGAACACG GGAAAGGATC CTTGGAAGAA GCTGAAGCAG AAAGACTTCT
4751 TCTGATTGCA ACTGAGAAAA GAGCACTTCT GATTGATGAG CTGAATAAGC
4801 TGAAGAGTGA AGGACCTCAG AGGAGAAACA AGACCAGTGT CATATCCCAG
4851 AGTGAATTTG CTCCATCTAA AGGGTCAGTC ACTCTGTCAG AAATCTGCTT
4901 GCCTCTGAAG GCAGATTTTG TCTGCAGCAC TGCGCAAAAA ACAGATGCAT
4951 CAAATTATTA CTACTTAATT ATGCTAAAAG CTGGGGCTGA GCAGATGGTC
5001 GCCACTCCAT TAGCAAGTAC TGCAAACTCT CTCAGTGGTG ACGCTCTGAC
```

Fig. 10 (Continued II)

```
5051 ATTTCCTACT ACATTTACTC TGCATGATGT TTCCAATGAC TTTGAAATAA
5101 ACATTGAAGT TTACAGCCTG GTACAAAAGA AAGATTCCTT GGGCCCCGAT
5151 AAGAAGAAGA AAGCCTCCAA GTCCAAGGCT ATTACTCCAA AGAGACTCCT
5201 CACATCTATA ACTTCAAAAA GCAGCCTTCA TTCTTCAGTT ATGGCCAGTC
5251 CCGGAGGTCT CGGTGCTGTG CGTACCAGCA ACTTTACCCT AGTTGGATCT
5301 CACACACTCT CCTTATCTTC TGTTGGAGAC ACTAAGTTTG CTTTGGACAA
5351 GGTACCTTTT TTGTCTCCGT TGGAAGGTCA CATCTGTTTA AAAATAAGCT
5401 GTCAAGTGAA TTCAGCTGTT GAGGAAAAGG GTTTCCTTAC CATATTTGAA
5451 GATGTTAGTG GCTTTGGTGC CTGGCACCGA AGATGGTGTG TTCTCTCTGG
5501 CAACTGTATC TCTTACTGGA CTTACCCAGA TGATGAGAGG CGAAAGAATC
5551 CCATAGGAAG GATAAATCTG GCCAATTGTA TCAGTCATCA GATAGAACCA
5601 GCCAACAGAG AATTTTGTGC AAGACGCAAC ACTCTGGAAT TGATTACTGT
5651 CCGACCACAA AGAGAAGACG ATCGAGAAAC TCTTGTCAGC CAATGTAGAG
5701 ACACACTCTG TGTCACCAAG AACTGGCTCT CTGCAGATAC TAAAGAAGAG
5751 CGGGATCTCT GGATGCAGAA ACTCAACCAG GTCATTGTTG ATATTCGCCT
5801 CTGCAGCCT GATGCATGCT ACAAGCCTGT TGGGAAGCCT TAAGCCGAGG
5851 AGCTTCTGCA CCGTGAGAGA CTTTGCTAGC TGTGTCTTCT TAAGAAGACA
5901 GTTAGAAGCA GCAGATTTGC AGGTTGTATT CTATGCTTTA AATATAAAAG
5951 GGTATGTGCA ATATTCACT ACATATTGTG CAGTATTTAT ATCTTTTCTA
6001 TGTAAAACTT CACCCAGTTT GTCTTGCATT CGTACATGTT TGACAGTCAA
6051 ATACTAACAA TATTCATGAG AATTGATGGG ATCCACCGGA TCTAGATAAC
6101 TGATCATAAT CAGCCATACC ACATTGTAG AGGTTTTACT TGCTTTAAAA
6151 AACCTCCCAC ACCTCCCCCT GAACCTGAAA CATAAAATGA ATGCAATTGT
6201 TGTTGTTGGG ATCCACCGGA TCTAGATAAC TGATCATAAT CAGCCATACC
6251 ACATTGTAG AGGTTTTACT TGCTTTAAAA AACCTCCCAC ACCTCCCCCT
6301 GAACCTGAAA CATAAAATGA ATGCAATTGT TGTTGTTGGC CGCGACTCTA
6351 GATCATAATC AGCCATACCA CATTTGTAGA GGTTTTACTT GCTTTAAAAA
6401 ACCTCCCACA CCTCCCCCTG AACCTGAAAC ATAAAATGAA TGCAATTGTT
6451 GTTGTTAACT TGTTTATTGC AGCTTATAAT GGTTACAAAT AAAGCAATAG
6501 CATCACAAAT TTCACAAATA AAGCATTTTT TTCACTGCAT TCTAGTTGTG
6551 GTTTGTCCAA ACTCATCAAT GTATCTTAAC
```

Fig. 12
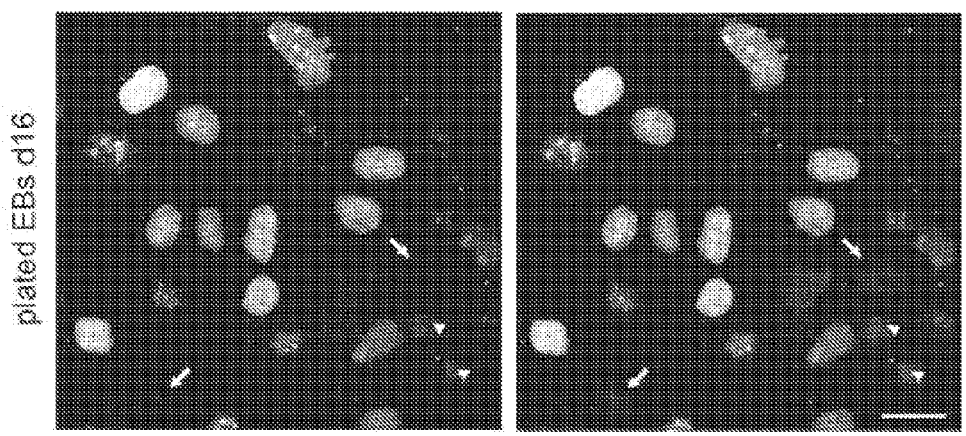
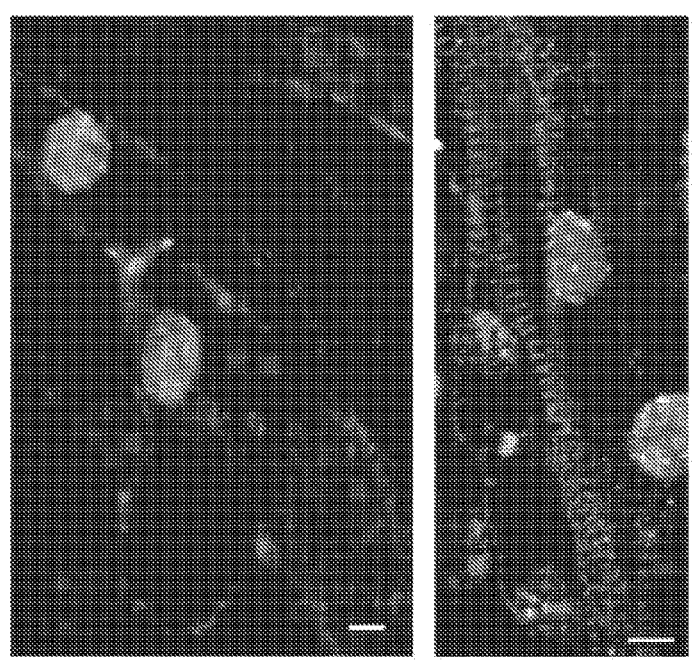

Fig. 13 (Continued)
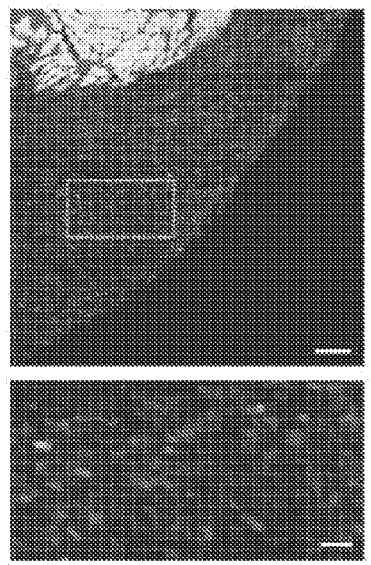
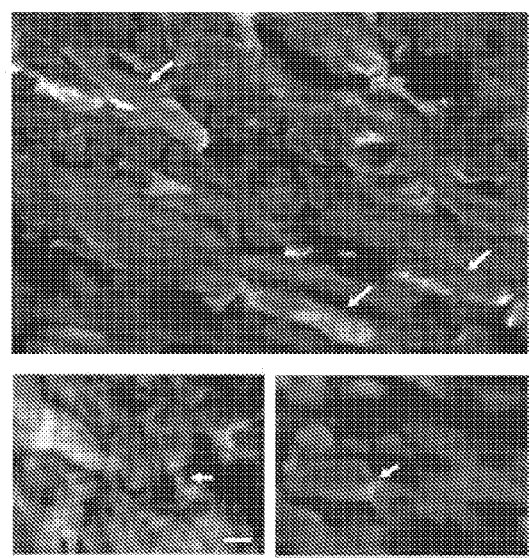
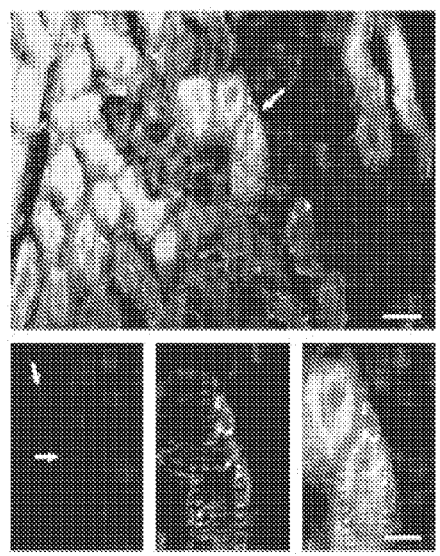

Fig. 14 (Continued)
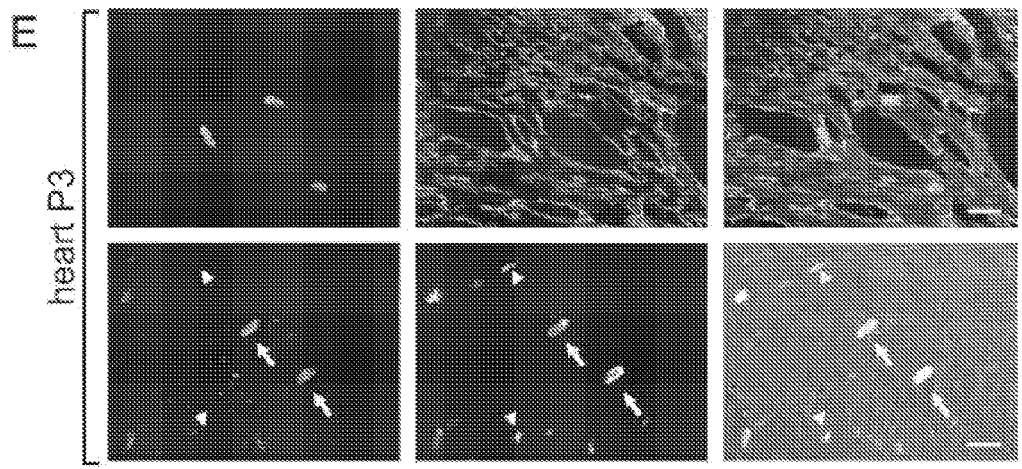
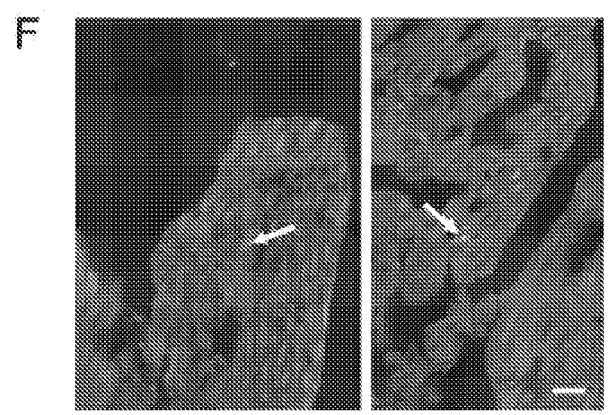
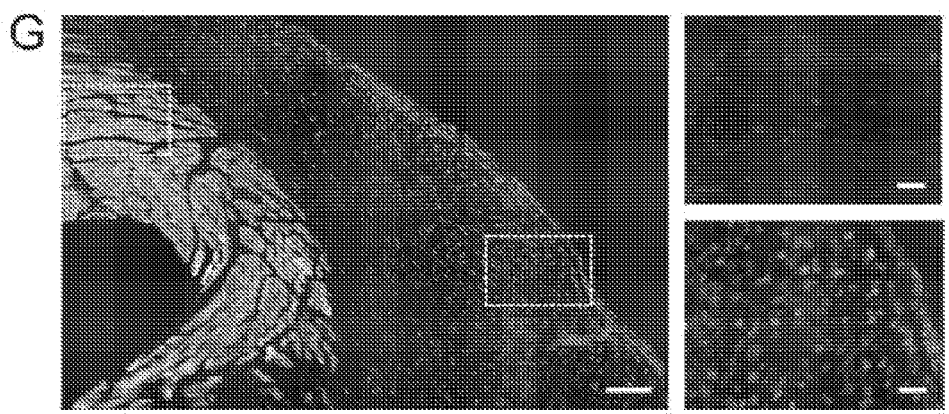

SEQUENCE LISTING

<160> NUMBER OF SEQ ID NOS: 4

<210> SEQ ID NO 1
<211> LENGTH: 6580
<212> TYPE: DNA
<213> ORGANISM: Artificial Sequence

```
<220> FEATURE:
<223> OTHER INFORMATION: EGFP-mouse anillin fusion protein

<400> SEQUENCE: 1
tagttattcg acattgatta ttgactagtt attaatagta atcaattacg gggtcattag    60
ttcatagccc atatatggag ttccgcgtta cataacttac ggtaaatggc ccgcctggct   120
gaccgcccaa cgaccccgc ccattgacgt caataatgac gtatgttccc atagtaacgc   180
caatagggac tttccattga cgtcaatggg tggagtattt acggtaaact gcccacttgg   240
cagtacatca agtgtatcat atgccaagta cgccccctat tgacgtcaat gacggtaaat   300
ggcccgcctg gcattatgcc cagtacatga ccttatggga cttcctact tggcagtaca   360 tctacgtatt agtcatcgct attaccatgg tcgaggtgag ccccacgttc tgcttcactc   420
tccccatctc ccccccctcc ccaccccaa ttttgtattt atttattttt taattatttt   480
gtgcagcgat ggggcgggg ggggggggg ggcgcgcgcc aggcggggcg gggcggggcg   540
aggggcgggg cggggcgagg cggagaggtg cggcggcagc caatcagagc ggcgcgctcc   600
gaaagtttcc ttttatggcg aggcggcggc ggcggcggcc ctataaaag cgaagcgcgc   660 ggcgggcggg agtcgctgcg ttgccttcgc ccgtgcccc gctccgcgcc gcctcgcgcc   720
gcccgccccg gctctgactg accgcgttac tcccacaggt gagcgggcgg gacggccctt   780
ctcctccggg ctgtaattag cgcttggttt aatgacggc cgtttctttt ctgtggctgc   840
gtgaaagcct taaagggctc cgggagggcc ctttgtgcgg gggggagcgg ctcgggggt   900 gcgtgcgtgt gtgtgtgcgt gggagcgcc gcgtgcggcc cgcgctgccc ggcggctgtg   960
agcgctgcgg gcgcggcgcg gggctttgtg cgctccgcgt gtgcgcgagg ggagcgcggc  1020
cggggggcgt gccccgcggt gcgggggcc tgcgagggga acaaaggctg cgtgcgggt  1080 gtgtgcgtgg gggggtgagc aggggtgtg ggcgcggcgg tcgggctgta accccccct  1140 gcaccccct ccccgagttg ctgagcacgg cccggcttcg ggtgcggggc tccgtacggg  1200
gcgtggcgcg gggctcgccg tgccgggcgg ggggtggcgg caggtggggg tgccgggcgg  1260
ggcggggccg cctcgggccg gggagggctc ggggagggg cgcggcggcc cccgagcgc  1320 cggcggctgt cgaggcgcgg cgagccgcag ccattgcctt ttatggtaat cgtgcgagag  1380
ggcgcaggga cttcctttgt cccaaatctg tgcggagccg aaatctggga ggcgccgccg  1440
caccccctct agcgggcgcg gggcgaagcg gtgcggcgcc ggcaggaagg aaatgggcgg  1500
ggagggcctt cgtgcgtcgc cgcgccgccg tcccttctc cctctccagc ctcggggctg  1560
tccgcggggg gacggctgcc ttcgggggg acggggcagg gcggggttcg gcttctggcg  1620
tgtgaccggc ggctctagag cctctgctaa ccatgttcat gccttcttct ttttcctaca  1680
gctcctgggc aacgtgctgg ttattgtgct gtctcatcat tttggcaaag aattgcccgg  1740
tcgccaccat ggtgagcaag ggcgaggagc tgttcaccgg ggtggtgccc atcctggtcg  1800
agctggacgg cgacgtaaac ggccacaagt tcagcgtgtc cggcgagggc gagggcgatg  1860
ccacctacgg caagctgacc ctgaagttca tctgcaccac cggcaagctg cccgtgccct  1920
ggcccaccct cgtgaccacc ctgacctacg gcgtgcagtg cttcagccgc taccccgacc  1980
acatgaagca gcacgacttc ttcaagtccg ccatgcccga aggctacgtc caggagcgca  2040
ccatcttctt caaggacgac ggcaactaca agacccgcgc cgaggtgaag ttcgagggcg  2100
acaccctggt gaaccgcatc gagctgaagg gcatcgactt caaggaggac ggcaacatcc  2160
tggggcacaa gctggagtac aactacaaca gccacaacgt ctatatcatg gccgacaagc  2220
```

```
agaagaacgg catcaaggtg aacttcaaga tccgccacaa catcgaggac ggcagcgtgc    2280
agctcgccga ccactaccag cagaacaccc ccatcggcga cggccccgtg ctgctgcccg    2340
acaaccacta cctgagcacc cagtccgccc tgagcaaaga ccccaacgag aagcgcgatc    2400
acatggtcct gctggagttc gtgaccgccg ccgggatcac tctcggcatg gacgagctgt    2460
acaagtccgg actcagatcc gacccgttta ccgagaagtt gctagaacga actcgtgcca    2520
gacgagagaa tcttcagaga aaaatggctg agaggcctac ggcagtagcg agatctgccc    2580
cgcatgcgaa gagaggcaga gagccacttt cagaagcaag taatcagcag cagcccctac    2640 caggggggcga agaaaaatct tgtacaaaac catcaccatc aaaaaaacgt tgttctgaca    2700
aaattgaagt gggagctccg gacttagaaa atacagaacc tattgatgtt gcaaagccct    2760
gttctccgat gcctgcaccc cggcaggcga agccccagc accagctgcc atcagcgagt    2820
ctgtggctgc cccagcagcc ctgctcagcg cggacagagg gctgaactca ggatccgaag    2880
catctgcaac ctcctcagtt aaaactcgaa tgcaaaggct tgctgagcag cggcgccatt    2940
gggatagtga tctcacagat gatgtatcag aaagttcata ctttgcacca gtgccaactg    3000
aggacaaggc tgcctcacct tctaagccac ccatttcaaa tgcctcagct actccagttg    3060
ggagaagggg ccgtctggcc aaccttgctg caacgatttg ctcctgggaa gatgatgtaa    3120
gccactcatc tgcaaagcaa atagtgtgc aagaacagcc tggtaccgct tgtttatcca    3180
aatcttcctc tgcaagtgga gcatctgcta gcatcaatag cagcagtgtt cagcaggaag    3240
ctacatgctg ttccccaagg gacggcaatg cctctgtcag gaaagaccca tcttcaaatg    3300
ctgcccatgg acctttgctt agcgcctcag tgtccagctc tgtgaaagcg tcttcccctg    3360
tgacagctgc taccttcatc actgaaaacc gtgaggcaca aaatcctgag ctacttcaca    3420
aaactgctag tcctctgaaa acagaggcgc ggaaaccatg tgagaagcca actttgtccc    3480
agggagctca gcccaaagag gaggctaaca gagaagtttg tctacagtca caatccaagg    3540
acaaacttgc aacaccagga ggaagaggaa ttaacccttt cctggaacgc tttggagagc    3600
gttgtcaaga acacagtaaa gaaagtccgt cttatagagc atctcataaa accccaaata    3660
tcactccaaa tacaaaagcc atccaggaaa gattattcaa acaaaacaca tgctcgtcta    3720
ctacccattt agcacagcag ctcaaacagg aacgtgaaaa agaactggca tgtcttcgtg    3780
gtcgacttga aagggcaat ttatggagtg cagaaaagaa tgaaaagtca agaagcaagc    3840
atctagaaac caaacaggaa gttcactgtc agaacactcc actcaagaaa catcaaactg    3900
tcgcaagcac cccattgact tctgtaacag ataaggtggc tgaaaatgaa ccagcagtga    3960
agctttctag cacagagcct gcaggttcca ctgaaagcga aatgacaaag tccagccctt    4020
tgaaaatcac gttgttttta gaagaagaaa aatccttaaa agtagcatca gacctggagg    4080
ttgagcagaa cactgaagca gtgcgtgagg ttgagatgag tgtggacgat gaggacatca    4140
atagctccag agtcattaac gacatcttca gtgacgtcct agaggaaggg gagctggatg    4200
tggaaaagag ccaagaggag atggaccaag tgggagcaga aaacagtgag gagcaggaag    4260
atgcgctcaa tatctcttca atgtctttac ttgctccgct agctcagacg gtcggtgtgg    4320
tgagcctaga gaatgtaatt tcttcacctc cgtcggaatt gagagactct aacctaagcg    4380
ctgcaagtcc taagcccggg aaattccaga gaacccgcgt ccctcgcgcc gaatctgccg    4440
atagcctcgg ttctgaggac cgggaccttc tctatagcat tgatgcatat aggtctcaaa    4500
gattcaaaga aacagaacgc ccttccataa agcaagtgat tgttcgaaag gaagatgtta    4560
cttcaaagtt gggtgaaaag aaaaacgtat tttctggtca agttaatatc aaacaaaaaa    4620
```

-continued

```
tgcaggagct caataatgac ataaatttgc agcagacagt gatctatcag gccagtcagg    4680
ctctcaactg ctgtgtggat gaagaacacg ggaaaggatc cttggaagaa gctgaagcag    4740
aaagacttct tctgattgca actgagaaaa gagcacttct gattgatgag ctgaataagc    4800
tgaagagtga aggacctcag aggagaaaca agaccagtgt catatcccag agtgaatttg    4860
ctccatctaa agggtcagtc actctgtcag aaatctgctt gcctctgaag gcagattttg    4920
tctgcagcac tgcgcaaaaa acagatgcat caaattatta ctacttaatt atgctaaaag    4980
ctggggctga gcagatggtc gccactccat tagcaagtac tgcaaactct ctcagtggtg    5040
acgctctgac atttcctact acatttactc tgcatgatgt ttccaatgac tttgaaataa    5100
acattgaagt ttacagcctg gtacaaaaga agattcctt gggccccgat aagaagaaga    5160
aagcctccaa gtccaaggct attactccaa agagactcct cacatctata acttcaaaaa    5220
gcagccttca ttcttcagtt atggccagtc ccggaggtct cggtgctgtg cgtaccagca    5280
actttaccct agttggatct cacacactct ccttatcttc tgttggagac actaagtttg    5340
ctttggacaa ggtaccttt ttgtctccgt tggaaggtca catctgttta aaaataagct    5400
gtcaagtgaa ttcagctgtt gaggaaaagg gtttccttac catatttgaa gatgttagtg    5460
gctttggtgc ctggcaccga agatggtgtg ttctctctgg caactgtatc tcttactgga    5520
cttacccaga tgatgagagg cgaaagaatc ccataggaag gataaatctg gccaattgta    5580
tcagtcatca gatagaacca gccaacagag aattttgtgc aagacgcaac actctggaat    5640
tgattactgt ccgaccacaa agagaagacg atcgagaaac tcttgtcagc caatgtagag    5700
acacactctg tgtcaccaag aactggctct ctgcagatac taaagaagag cgggatctct    5760
ggatgcagaa actcaaccag gtcattgttg atattcgcct ctggcagcct gatgcatgct    5820
acaagcctgt tgggaagcct taagccgagg agcttctgca ccgtgagaga ctttgctagc    5880
tgtgtcttct taagaagaca gttagaagca gcagatttgc aggttgtatt ctatgcttta    5940
aatataaaag ggtatgtgca atattcact acatattgtg cagtatttat atctttcta    6000 tgtaaaactt cacccagttt gtcttgcatt cgtacatgtt tgacagtcaa atactaacaa    6060
tattcatgag aattgatggg atccaccgga tctagataac tgatcataat cagccatacc    6120
acatttgtag aggttttact tgctttaaaa aacctcccac acctccccct gaacctgaaa    6180
cataaaatga atgcaattgt tgttgttggg atccaccgga tctagataac tgatcataat    6240
cagccatacc acatttgtag aggttttact tgctttaaaa aacctcccac acctccccct    6300
gaacctgaaa cataaaatga atgcaattgt tgttgttggc cgcgactcta gatcataatc    6360
agccatacca catttgtaga ggttttactt gctttaaaaa acctcccaca cctcccctg    6420 aacctgaaac ataaaatgaa tgcaattgtt gttgttaact tgtttattgc agcttataat    6480
ggttacaaat aaagcaatag catcacaaat ttcacaaata aagcattttt ttcactgcat    6540
tctagttgtg gtttgtccaa actcatcaat gtatcttaac                         6580
```

<210> SEQ ID NO 2
<211> LENGTH: 20
<212> TYPE: DNA
<213> ORGANISM: Artificial Sequence
<220> FEATURE:
<223> OTHER INFORMATION: PCR primer anillin 121 forward

<400> SEQUENCE: 2
gcctgcactc acttctttcc                                                20

```
<210> SEQ ID NO 3
<211> LENGTH: 20
<212> TYPE: DNA
<213> ORGANISM: Artificial Sequence
<220> FEATURE:
<223> OTHER INFORMATION: PCR primer anillin 4062 reverse

<400> SEQUENCE: 3
gactatgcag gcccaaatgt                                              20

<210> SEQ ID NO 4
<211> LENGTH: 25
<212> TYPE: DNA
<213> ORGANISM: Artificial Sequence
<220> FEATURE:
<223> OTHER INFORMATION: PCR primer anillin-BamH1 forward

<400> SEQUENCE: 4
cccacttcaa ttttgtcaga acaac                                        25
```

NUCLEIC ACID EXPRESSION CONSTRUCT AND ITS USE AS A CELL PROLIFERATION MARKER

CROSS REFERENCE TO PRIOR APPLICATIONS

This application is a U.S. National Phase application under 35 U.S.C. §371 of International Application No. PCT/EP2010/060208, filed on Jul. 15, 2010, and which claims benefit to European Patent Application No. 09009233.9, filed on Jul. 15, 2009. The International Application was published in English on Jan. 20, 2011 as WO 2011/006962 A1 under PCT Article 21(2).

FIELD

The present invention provides a nucleic acid expression construct, its use as a cell proliferation marker, and related methods thereof.

BACKGROUND

Eukaryotic cell division proceeds through a highly regulated event, i.e. the cell cycle, comprising consecutive phases termed G1, S, G2 and M. Disruption of the cell cycle or of the cell cycle control mechanisms can result in cellular abnormalities or disease states such as cancer. The disruption of cell cycle control can be due to multiple genetic changes that transform growth-limited cells into highly invasive cells that are unresponsive to normal control of growth. Transition of normal cells into cancer cells can arise though loss of correct function in DNA replication and DNA repair mechanisms. All dividing cells are subject to a number of control mechanisms, known as cell-cycle checkpoints, which maintain genomic integrity by arresting or inducing destruction of aberrant cells. The investigation of cell-cycle progression and cell-cycle control is therefore of significant interest for revealing the molecular mechanims underlying cell cycle proliferation, as well as its disregulation in form of, for example, cancer. Consequently, revealing the principles of cell cycle progression is a needful help in designing anticancer drugs (as described in Tyson and Novak, Curr. Biology 18, R759-R768, 2008).

The major events of the eucaryotic cell cycle—such as DNA replication, mitosis, and cytokinesis—are triggered by a well-defined and sophisticated cell cycle control system. A major component of this cell cycle control system is a family of protein kinases known as cyclin-dependent kinases (Cdks). The oscillating activity of these kinases directly correlates with the initation or regulation of cell cycle progression, wherein the cyclical changes in Cdk activity in turn are controlled by a variety of enzymes and other proteins. The most important Cdk regulators are proteins known as cyclins which undergo a cycle of synthesis and degradation in each cell cycle. That is, the cyclin dependent kinases associate successively with different cyclins to trigger the different events of the cell cycle, and the activity of the Cdks is usually terminated by cyclin-dependent proteolytic degradation.

Cell cycle control crucially depends on at least two distinct enzyme complexes that act at different times in the cycle to cause the proteolysis and thus the inactivation of key proteins of the cell cycle control system. Most notably, cyclin-Cdk complexes are inactivated by regulated proteolysis of cyclins at certain stages of the cell-cycle, wherein the destruction of cyclins occurs by a ubiquitin-dependent mechanism in that an activated enzyme complex recognizes specific amino acid sequences on the protein to be degraded and attaches multiple copies of ubiquitin to it, thereby marking the protein for complete destruction by the 26S proteasome. Ubiquitination is a covalent modification which involves the formation of an isopeptide bond between the carboxy-terminus of ubiquitin and the $\epsilon$-amino group of a lysine residue within the acceptor protein.

The accurate determination of the cell cycle status is a key requirement for investigating cellular processes that affect the cell cycle and/or cell cycle progression, for example, in the context of various biological processes including, e.g. wound healing, cancer, or development. Furthermore, the accurate determination and control of cell cycle progression has an important impact on all aspects of regenerative medicine which indispensably relies on the use of embryonic stem (ES) cells. Embryonic stem (ES) cells are characterized by their ability to develop into all cell types of the body. However, remarkably little is yet known about the exact factors that make them differentiate into a specific type of cell. The analysis of cell cycle progression on the basis of the proliferative and developmental potential of embryonic stem (ES) cells thus promises successful strategies for transplantation therapies ranging from, e.g., heart disease to Parkinson's disease to leukemia due to the almost unlimited supply of specific cell types.

Cell cycle progression is tightly regulated by the defined temporal and spartial expression, localisation and destruction of a number of cell cycle regulators which exhibit a highly dynamic behavior during the cell cycle. For example, at specific stages of the cell cycle, some proteins translocate from the nucleus to the cytoplasm, or vice versa, thereby marking and controlling the transition from one phase of the cell cycle to another, e.g. the transition from G2 phase to mitosis or its exit from mitosis. Others are expressed only at specific phases of the cell cycle and are then rapidly degraded.

The mechanisms and control elements which regulate the temporal expression and destruction of protein factors with a key role in cell cycle progression have been elucidated in a number of studies (see, for example, Nurse, P., Cell 100 (1), 71-78, Jan. 7, 2000). More recently, the visualization of spatiotemporal dynamics of eukaryotic cell cycle progression including the visualization of proteins that mark cell cycle transitions has come into focus. For example, several cell-cycle markers that identify the S phase and the subsequent transition to G2 in live cells have been developed by fusing fluorescent proteins to nuclear proteins such as proliferating cell nuclear antigen (PCNA), DNA ligase I, or the C terminus of helicase B (as described, for example, in Easwaran et al., Cell Cycle 4, 453-455, 2005). However, since identification of cell-cycle transitions requires the detection of subtle and often minute changes in the distribution pattern and intensity of fluorescence signals, these markers are not suitable to track cell cycle phase transitions with high contrast.

Determination and modulation of cell cycle progression have important implications for all aspects of stem cell biology and regenerative medicine. Current strategies in the field focus on re-induction of proliferation in postmitotic cells or use of stem cells as a source for cell replacement therapies. The most widely used approach for the identification of proliferating cells is based on staining of fixated cells with typical proliferation markers such as Ki-67 PCNA or pHH3. This, as well as the use of thymidine analogons such as BrdU, CldU or IdU, is prone to a number of artefacts, one of the most common being the labelling of cells undergoing endoreduplication, acytokinetic mitosis or DNA repair (as described, for example, in Breunig, J. J. et al., Cell Stem Cell 1, 612-627, 2007). Endoreduplication is defined as continuing rounds of DNA replication without karyokinesis or cytokinesis (as described in Storchova, Z. and Pellman, D., Nat. Rev. Mol. Cell. Biol. 5, 45-54, 2004; Brodsky, W. Y. and Uryvaeva, I. V., Int. Rev. Cytol. 50, 275-332, 1977), whereas acytokinetic mitosis is karyokinesis without cyotkinesis. Both are common processes during development and under pathological conditions in tissues such as cardiac muscle, liver, or uterine decidua. The resulting polyploidy causes false positives in proliferation assays and an overestimate of dividing cells.

During postnatal heart growth and development cardiac muscle cells undergo acytokinetic mitosis resulting in binuclear cells (as described in Soonpaa et al., Am J Phys, 271, H2183-9, 1996), followed by endoreduplication (as described in Storchova, Z. and Pellman, D., Nat. Rev. Mol. Cell. Biol. 5, 45-54, 2004); these cells are thought to be incapable of performing cytokinesis (as described in Pasumarthi, K. B. and Field, L. J., Circ. Res. 90, 1044-1054, 2002). Current approaches to assess cardiac proliferation cannot provide detailed insight into variations of the cell cycle rendering the estimate of cardiac muscle renewal inaccurate. In fact this and additional caveats are likely to underlie the substantial controversy about proliferating cardiac muscle cells reported for intact and diseased or infarcted hearts (as described in Soonpaa, M. H. and Field, L. J., Circ. Res. 83, 15-26, 1998; Hsieh, P. C. et al., Nat. Med. 13, 970-974, 2007; Beltrami, A. P. et al., N. Engl. J. Med. 344, 1750-1757, 2001). The observation of cytokinesis consisting of a contractile ring and the appearance of a midbody prior to daughter cell separation would be the only definitive proof for proliferative activity in cardiomyocytes.

Visualization of the cell-cycle transition from G1 to S phase in live cells has recently been described by the development of a dual-color imaging system in which the inversely oscillating human E3-ligase substrates Cdt and Geminin have been fused to red- and green-emitting fluorescent proteins, respectively (as described in Sakaue-Sawano et al., Cell 132, 487-498, 2008). This so called "Fucci" system (fluorescent ubiquitination-based cell cycle indicator), which employs the parallel use of two individual reporter constructs, allows for the monitoring of structural changes and cell cycle dynamics of individual cells by labeling G1 phase nuclei red and S/G2/M phase nuclei green.

WO 03/031612 describes a nucleic acid reporter construct comprising a nucleic acid sequence encoding a detectable live cell reporter molecule under the control of at least one cell cycle phase-specific expression control element and a destruction control element, as well as methods for determining the cell cycle position of a cell related thereto.

There is always need for an improved method of visualizing and analyzing cell cycle progression in eucaryotic cells, for example, for systems that allow the identification of cell division versus mere cell cycle variation. A promising approach to unequivocally prove cell division is the direct visualization of the contractile ring and midbody occurring in the late mitotic (M) phase of the cell cycle. The contractile ring assembles equatorially at the cell cortex and constricts the cell membrane, thereby forming two daughter cells. At the same time the midbody, which is a microtubule rich structure located in a small cytoplasmic bridge between the daughter cells, forms and their separation is completed by its cleavage.

The identification and modulation of proliferating cells is of high relevance for stem cell research and regenerative medicine. However, current approaches to quantify cell proliferation are inaccurate in tissue types such as heart muscle cells displaying variations of the cell cycle namely acytokinetic mitosis and endoreduplication. To overcome these limitations, the present invention provides an in vivo reporter system using a protein with a wild-type destruction signal fused to a reporter protein for high resolution of the M-phase. This enables the visualization of cytokinesis and midbody formation as hallmarks of cell division in virtually all cell types and organs of transgenic mice. Furthermore, the present invention enables cell division, acytokinetic mitosis and endoreduplication to be distinguished. Thus, this new assay allows the monitoring and quantitation of cell proliferation and division in vitro and in vivo even in tissue types prone to DNA repair and variations of the cell cycle.

SUMMARY

An aspect of the present invention is to provide a nucleic acid expression construct encoding a fusion protein comprising a reporter protein and a protein with a wild-type destruction signal, wherein the sequence encoding the fusion protein is operably linked to a non-endogenous promoter, and wherein said fusion protein localizes during cell cycle progression to subcellular structures selected from the group consisting of the cell cortex, the contractile ring, and the midbody. An alternative aspect of the present invention is to provide a nucleic acid expression construct which can be easily handeled both in in vitro and in vivo cell systems, and which provides for a high contrast and accuracy read-out without the use of dual reporter constructs.

The present invention provides a nucleic acid expression construct which encodes a fusion protein which includes a reporter protein and a protein with a wild-type destruction signal. A sequence encoding the fusion protein is operably linked to a non-endogenous promoter. The fusion protein localizes during a cell cycle progression to subcellular structures selected from a cell cortex, a contractile ring, and a midbody. Said nucleic acid expression construct has surprisingly been found to be suitable for monitoring mitotic activity in general, and also in cell types which are prone to undergoing acytokinetic mitosis and endoreduplication, since the specific localization of the fusion protein greatly improves the determination of the cell cycle phase status of individual cells and allows for the monitoring of cell cycle progression in individual cells for several cell cycles (e.g., Example 1). Consequently, the fusion protein encoded by the nucleic acid construct of the present invention is especially suitable as a reporter protein for visualizing cell cycle progression.

BRIEF DESCRIPTION OF THE FIGURES

The present invention is described in greater detail below on the basis of embodiments and of the Figures in which:

FIG. 1 shows that EGFP-anillin expression displays the endogenous localization;

FIG. 2 shows that anillin is a mitotic marker;

FIG. 3 shows that EGFP-anillin expression is specific to mitotic cells only;

FIG. 5 shows that EGFP-anillin indicates proliverative cells in EBs;

FIG. 7 shows an EGFP-anillin lentiviral system;

FIG. 8 shows a cardiac-specific expression of EGFP-anillin;

FIG. 9 shows candidate promoters for cell-cycle specific expression of EGFP-anillin;

FIG. 10 shows the nucleic acid sequence of SEQ ID NO: 1;

FIG. 12 shows that EGFP-anillin is a mitotic marker in ESC-derived differentiating cells;

SEQUENCE LISTING

Figure 4:
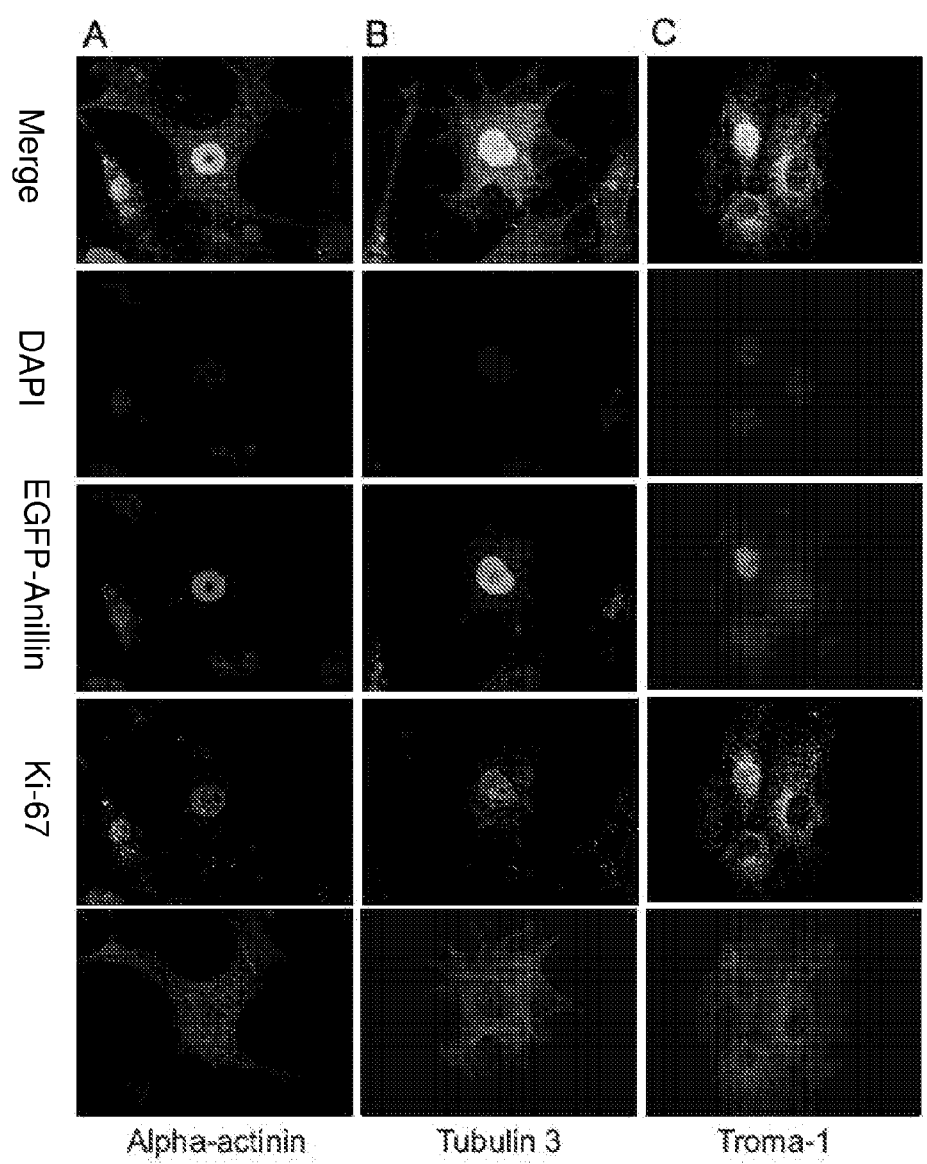
FIG. 4 shows that EGFP-anillin ES cell clones differentiate into all three germ layers.

The Sequence Listing associated with this application is filed in electronic form via EFS-Web and is hereby incorporated by reference into this specification in its entirety. The name of the text file containing the Sequence Listing is Sequence_Listing_090112. The size of the text file is 9,585 Bytes, and the text file was created on Jan. 9, 2012.

DETAILED DESCRIPTION

In the context of the present invention, the term "nucleic acid expression construct" generally refers to any kind of nucleic acid molecule that can be expressed in a cell. The nucleic acid expression construct of the present invention can be any plasmid or vector suitable for expressing a protein of interest in dividing or non-dividing cells, including, but not limited to, plasmids or vectors designed for transient or stable transfection including viral transduction. However, the expression construct of the present invention may also be a nucleic acid which encodes the fusion protein comprising a fluorescence reporter protein and a protein with a wild-type destruction signal and which is subsequently cloned into a respective vector to ensure expression.

The terms "plasmid" or "vector" include all nucleic acid constructs that are suitable for introducing or transferring a nucleic acid sequence encoding a gene of interest into a cell. Such constructs are known in the art, and can be commercially purchased from diverse suppliers including, e.g., Promega™ (Madison, Wis., USA), Qiagen® (Hilden, Germany), or Invitrogen™ (Carlsbad, Calif., USA). The plasmid or vector according to the present invention may comprise the DNA of a transmissible agent into which foreign DNA can be inserted. A common way to insert one segment of DNA into another segment of DNA involves the use of enzymes called restriction enzymes that cleave DNA at specific sites (e.g. palindrome sequences) called restriction sites. A "cassette" refers to a DNA coding sequence or a segment of DNA that encodes an expression product that can be inserted into a plasmid or vector at defined restriction sites. The term "transfection" as used herein refers to all kind of methods known in the art that are suitable to introduce a nucleic acid sequence encoding a gene of interest into a cell. The term "viral transduction" means any kind of method known in the art that is suitable to introduce a gene into a cell by viral infection. Such methods are known to the person skilled in the art and are, e.g., described in Sambrook et al., 2000 (Molecular Cloning: A laboratory manual, Third Edition).

In order to provide expression of the fusion protein, the nucleic acid construct of the present invention further comprises a non-endogenous promoter that is operably linked to the nucleic acid sequence encoding said protein and which is suitable for driving the expression of a protein in a cell. However, it is explicitly encompassed within the present invention that the claimed expression construct may represent an intermediate product, which is subsequently cloned into a suitable expression vector to ensure expression of the contruct.

The term "promoter" as used in the context of the present invention generally refers to any kind of regulatory DNA sequence operably linked to a downstream coding sequence, wherein said promoter is capable of binding RNA polymerase and initiating transcription of the encoded open reading frame in a cell, thereby driving the expression of said downstream coding sequence. The nucleic acid expression construct of the present invention encodes a fusion protein comprising a detectable reporter protein and a protein with a wild-type destruction signal, wherein a non-endogenous promoter sequence is operably linked to the nucleic acid sequence encoding the fusion protein of the present invention. The non-endogenous promoter sequence of the present invention can be any kind of promoter sequence known to the person skilled in the art, including, but not limited to, constitutive promoters, inducible promoters, cell cycle-specific promoters, and cell type-specific promoters.

The term "non-endogenous" as used herein generally refers to any promoter sequence other than the endogenous promoter sequence that is naturally operably linked to the protein with a wild-type destruction signal in the cell it is derived from.

The term "operably linked" as used herein means that the gene elements are arranged as such that they function in concert for their intended purposes, e.g. in that transcription is initiated by the promoter and proceeds through the DNA sequence encoding the fusion protein of the present invention. That is, RNA polymerase transcribes the sequence encoding the fusion protein into mRNA, which in then spliced and translated into a protein. Examples of nucleic acid expression constructs of the present invention are, e.g., illustrated in FIGS. 1, 7, 8, 9 and 10.

The nucleic acid expression construct of the present invention might further comprise all other sorts of nucleic acid sequences, including, but not limited to, polyadenylation signals, splice donor and splice acceptor signals, intervening sequences, transcriptional enhancer sequences, translational enhancer sequences, drug resistance gene(s) or alike. Optionally, the drug resistance gene and the fluorescence reporter gene may be operably linked by an internal ribosome entry site (IRES), which might be either cell cycle-specific or cell cycle-independent.

A "constitutive promoter" as referred to herein means any kind of unregulated promoter known to the person in the art that allows for a continual transcription of the encoded gene. A constitutive promoter of the present invention may further comprise additional regulatory sequences, and may be selected from the group consisting of, but not limited to, the immediate/early promoter/enhancer of cytomegalovirus (CMV promoter), the SV40 promoter, the chicken β-actin promoter, the polyubiquitin promoter, the PGK (phosphoglycerate kinase) promoter, the ROSA26 promoter, or any combination thereof.

The constitutive promoter of the present invention may, for example, be a combination of the CMV early enhancer and the chicken β-actin promoter, i.e. the CAG promoter. The CMV early enhancer/chicken β-actin promoter (CAG) promoter offers a valuable tool for the long term expression of trans genes during stem cell differentiation and has been described in the art to successfully express transgenes in undifferentiated ES cells undergoing differentiation towards neuronal, myogenic and mesodermal cell types (as described, for example, in Alexopoulou et al., BMC Cell Biology, 9:2., 2008).

In the context of the present invention, it has been found that optimal visualization of cell cycle progression is achieved when the fusion protein encoded by the nucleic acid expression construct of the present invention is expressed under the control of a constitutive promoter. Optimal results have been obtained by expressing the fusion protein under the control of, for example, the CAG promoter. Expression of the fusion protein under the control of a constitutive promoter, for example, under the control of the CAG promoter (i.e. a combination of the CMV early enhancer and the chicken β-actin promoter), is further illustrated in Examples 1, 2, 3, and 5.

In an embodiment of the present invention, the nucleic acid expression construct of the present invention can, for example, comprise a constitutive promoter.

In an embodiment of the present invention, the constitutive promoter of the present invention can, for example, be selected from the group consisting of the immediate/early promoter/enhancer of cytomegalovirus (CMV promoter) and the chicken β-actin promoter.

In an embodiment of the present invention, the constitutive promoter of the present invention can, for example, be the CMV early enhancer/chicken β-actin promoter (CAG) promoter.

A "cell cycle-specific promoter" as referred to in the context of the present invention generally includes any DNA sequences that control transcription and/or translation of one or more nucleic acid sequences including any kind of regulatory sequences, allowing for the cell cycle-specific control of gene expression. A cell cycle-specific promoter of the present invention includes any expression control element that is specifically active in one or more phases of the cell cycle. Cell cycle-specific promoter of the present invention may be selected from, but not limited to, the E2F1 promoter, the Ki-67 promoter, the PCNA promoter, Cyclin B1 promoter, Cyclin D2 promoter, Cdc25B promoter, Cdc25C promoter, Cyclin A2 promoter, Cdc2 promoter, Cyclin E promoter, Cdc6 promoter, DHFR (dihydrofolate reductase) promoter, Mcm2, and histones promoters, or any combination thereof. In addition, the cell-cycle specific promoter of the present invention may comprise cell cycle-specific IRES elements and/or other elements that influence translational control in a cell cycle specific manner. IRES elements suitable for use in the present invention include, but not limited to, G2-IRES, HCV IRES, ODC IRES, and c-myc IRES.

In the context of the present invention, cell cycle-specific promoters have successfully been used to drive the expression of the fusion protein encoded by the nucleic acid expression construct (see Example 7). In this respect, it was surprisingly found that no accumulation of the fusion protein in postmitotic cells occurred when cell cycle-specific promoters were operably linked to the sequence encoding the fusion protein of the present invention.

In an embodiment of the present invention, the nucleic acid expression construct of the present invention can, for example, comprise a cell cycle-specific promoter.

In an embodiment of the present invention, the cell cycle-specific promoter of the present invention can, for example, be selected from the group consisting of the E2F1 promoter, the Ki-67 promoter, the PCNA promoter, and the cyclin B1 promoter, or any combination thereof.

The term "cell type-specific promoter" as referred to herein generally means any promoter sequence which controls the expression of a gene of interest in a specific tissue or in a particular type of cell(s). Cell type-specific promoters of the present invention can include, but are not limited to, all kind of promoter sequences that control gene expression in primary cells, for example, in primary cardiomyocytes or fibroblasts. A cell type-specific promoter of the present invention may, for example, be selected from the group consisting of, but not limited to the cardiomyocyte-specific α-MHC promoter and the Nkx2.5 promoter.

There is ongoing controversy in the art if adult, postmitotic cardiomyocytes are still able to proliferate under certain circumstances or not. In order to address this question, the cardiomyocyte-specific α-MHC promoter has successfully been used in the context of the present invention to drive the expression of a fusion protein encoded by the nucleic acid expression construct of the present invention in embryonic stem (ES) cells. These results are described in Example 6, and are further illustrated in FIG. 8.

In an embodiment, the nucleic acid expression construct of the present invention can, for example, comprise a cell type-specific promoter, for example, the cardiomyocyte-specific α-MHC promoter.

The term "inducible promoter" as referred to herein means any promoter known to the person skilled in the art that regulates expression in response to a stimulus. An inducible promoter of the present invention can be bound by a transcription regulatory protein that either represses or activates gene expression. The repressor or activator protein in turn is responsible to the stimulus, such as the presence or absence of a nutrient, a protein, or some other environmental signal. Inducible promoters of the present invention may include, but are not limited to, the pTet-on/pTet-off system. Such systems are known in the art and can be commercially purchased from, e.g, Clontech™ (USA).

The nucleic acid expression construct of the present invention may allow for the production of either large or small amounts of stable mRNA once it is introduced into a cell of interest. The nucleic acid expression construct of the present invention may further contain any kind of regulatory sequences that function as enhancer or silencer elements, and which might regulate and/or modulate the activity of the promoter and thereby the rate of transcription and thus expression of the protein of interest. Additionally, the nucleic acid expression construct may additionally contain a strong termination codon, an insertion of transcription termination sequence and a PTIS (portable translation initiation sequence), and may be designed as to provide an adjustment of distance between promoter and cloned gene of interest. In an embodiment, the nucleic acid expression construct of the present invention may, for example, comprise all necessary sequences required for producing a living virus, for example, a living lentivirus, including, but not limited to, 5' and/or 3'-long terminal repeats, coding sequences for HIV, RRE and WRE and alike. Such constructs are known to the person skilled in the art, and can, e.g., be commercially purchased from Invitrogen™ (Carlsbad, Calif., USA).

As detailed above, an aspect of the present invention is to provide a nucleic acid expression construct that exhibit activation and destruction of a detectable reporter molecule in a cell cycle phase specific manner. Said detectable reporter molecule is represented by the fusion protein encoded by the nucleic acid expression construct of the present invention, and is further defined and explained as follows.

In the context of the present invention, the term "fusion protein" generally means any kind of protein which is designed by a reporter gene and a gene of interest. Reporter genes can be used to assay for the expression of the gene of interest, which may produce a protein that has little obvious or immediate effect on the cell culture or the organism. In these cases, the reporter is directly attached to the gene of interest to create a gene fusion. That is, the two genes are under the same promoter and are transcribed into a single messenger RNA molecule. The mRNA is then translated into protein. In these cases, it is thus important that both proteins are able to properly fold into their active conformations and interact with their substrates despite being fused. In building the DNA construct, a segment of DNA coding for a flexible polypeptide linker region is usually included so that the reporter and the gene product will only minimally interfere with one another. The fusion protein of the present invention may further comprise one or more affinity purification tag(s) which enable(s) and/or facilitate(s) the biochemical purification of the fusion protein from cellular extracts by means of affinity purification methods. Such affinity purification tags are known to the person skilled in the art and include, but are not limited to, the 6× Histidin tag, the Glutathione-S-transferase (GST) tag, the Maltose-binding protein (MBP) tag, the S-tag, the NusA and NusB tag, the HA tag, the FLAG tag, the Protein-A tag, and all kind of tandem affinity purification (TAP) tags. Such affinity tags may be either fused to the N- or C-terminal part of the reporter protein, or to the N- or C-terminal part of the protein of interest, or to the N- or C-terminal part of both the reporter gene and the protein of interest.

In the context of the present invention, it has surprisingly been found that the expression of a fusion protein comprising a detectable reporter protein and a protein with a wild-type destruction signal, wherein said fusion protein localizes during cell cycle progression to subcellular structures selected from the group consisting of the cell cortex, the contractile ring, and the midbody, is suitable to visualize cell cycle progression, since such a protein is degraded during cell division in cells when $APC^{Cdh1}$ is active. This complete proteolytic degradation is advantageous in that (i) the (over)expression of the reporter protein does not result in any toxic accumulation of the protein within the cell body, for example, not in embryonic stem (ES) cells and/or during mouse embryogenesis, in that (ii) localisation of the reporter protein during cell cycle progression can be visualized with a higher contrast since the protein moiety which is not trapped in subcellular structures is immediately degraded during late M phase, and in that (iii) the reporter protein encoded by the nucleic acid expression construct of the present invention is not detectable and/or readily visuable in postmitotic cells. That is, the nucleic acid expression construct of the present invention constitutes an optimal cell proliferation marker.

The term "reporter protein" as used herein generally refers to any protein that can be easily detected by standard biochemical or optical methods and which is not endogenously expressed or present in the research system, cell system or organism employed in the context of the present invention. A reporter protein of the present invention may be any kind of fluorescent, luminescent, or enzymatic reporter protein known in the art and may be selected from, but not limited to, beta-galactosidase (e.g., encoded by the bacterial gene lacZ), luciferase (e.g, firefly luciferase from *Photinus pyralis, Renilla reniformis, Pyrophorus plagiophthalamus*), chloramphenyl acetyltransferase (CAT; from bacteria), arabinofuranosidase, beta-glucuronidase (GUS; from bacteria) or any kind of fluorescent protein (e.g., from jelly fish).

In an embodiment, the fusion protein of the present invention can, for example, comprise a fluorescent reporter protein and a protein with a wild-type destruction signal.

The term "fluorescent reporter protein" as used herein generally refers to any kind of protein which can be visualized by means of fluorescence detection. In an embodiment of the present invention, the fluorescent reporter protein of the present invention can, for example, be a green fluorescence protein (GFP) from *Aequorea victoria* including any known functional analogues thereof in which the amino acid sequence of wild type GFP has been altered by amino acid deletion, addition, or substitution. Suitable GFP analogues for use in the present invention include, but are not limited to, EGFP (enhanced green fluorescence protein), EYFP (enhanced yellow fluorescence protein), and ECFP (enhanced cyan fluorescence protein). These fluorescence reporter proteins are known in the art, and can, e.g., be commercially purchased from Clontech™, USA. Other fluorescence reporter proteins of the present invention include, but are not limited to, *Aequorea coerulescence* jellyfish fluorescent protein (AcGPF1), DsRed, HcRed, AsRed, ZsGreen, ZsYellow, AmCyan fluorescent protein (BD Clontech, USA), *Renilla* GFP (Stratagene, USA), monomeric Kusabira-Orange (mKO1 and mKO2) and monomeric Azami-Green (mAG) (MBL Medical & Biological Laboratories Co., Ltd.), mCherry, mKate, mKatushka, TurboRFP and TagRFP (Evrogen, Russia) and any functional fragment or derivative thereof.

In an embodiment, the fluorescent reporter protein of the present invention can, for example, be EGFP (enhanced green fluorescence protein), or any functional fragment or derivative thereof.

In an embodiment, the fusion protein according to the present invention can, for example, be a fusion protein comprising a luminescent reporter protein and a protein with a wild-type destruction signal.

The term "luminescent reporter protein" as used herein generally refers to any kind of protein which is detectable due to the emission of light. A luminescent reporter protein of the present invention includes, but is not limited to, luminescent reporter proteins such as *Renilla*, or firefly luciferase, including, but not limited to, *Photinus pyralis, Renilla reniformis*, or *Pyrophorus plagiophthalamus*. Luminescent reporter proteins as well as their detection methods are known in the art and are, e.g., described in Rabinovich B. A. et al., Proc. Natl. Acad. Sci. USA, 105(38), 14342-6, 2008. Here, a combination of codon optimization, removal of cryptic splice sites and retroviral modification was used to engineer an enhanced firefly luciferase (ffLuc) vector. Luminescent reporter genes including their detection systems are, e.g., commercially available from Promega™ (Madison, Wis., USA).

In an embodiment, the reporter protein of the present invention can, for example, be a fluorescent protein, a luminescent protein or a protein in form of beta-galactosidase. The reporter protein in form of beta-galactosidase can, for example, be encoded by the bacterial gene lacZ in the context of the present invention.

In an embodiment, the fusion protein according to the present invention can, for example, be a protein comprising a fluorescent reporter protein, a protein with a wild-type destruction signal, and one or more affinity purification tag(s).

The combination of a fluorescence reporter protein and an affinity purification tag is known in the art as a localisation and affinity purification (LAP) tag. In higher eucaryotic cells, the LAP tag faciliates the generation of a stable cell line which can be sorted by FACS to obtain clonal cell lines expressing moderate amounts of the fusion protein.

The term "wild-type destruction signal" as used herein generally refers to any kind of wild-type consensus sequence and/or recognition signal targeting the protein of the present invention for proteolytic degradation. In an embodiment, the wild-type destruction signal as used in the context of the present invention can, for example, target the fusion protein for cell cycle-dependent proteolysis. The wild-type destruction signal of the present invention may, for example, be one which mediates ubiquitination of the fusion protein, thereby targeting the protein for ubiquitin-mediated proteolysis. The wild-type destruction signal of the present invention may be constituted by either one or more individual consensus sequences, for example, by two individual consensus sequences, or by three individual consensus sequences. In the context of the present invention, a consensus sequence constituting a wild-type destruction signal can have the motif of a destruction box (D-Box) or a KEN-box. The destruction box can, for example, have a consensus sequence of SEQ ID No. 5: RXXLXXXXN/D/E or RXXL, wherein X is any amino acid. The KEN-box can have a consensus sequence of SEQ ID NO. 6: KENXXXN, wherein X is any amino acid. Alternatively, a consensus sequence of the present invention can be any other sequence motif known in the art to mediate protein destruction, including, but not limited to, e.g. motifs such as SEQ ID NO. 7: LLVRGRTLVV, or cyclin A N-terminus.

According to the present invention, said wild-type destruction signal is part of a protein. This protein can, for example, localize to the subcellular structures as indicated and can therefore be responsible for the claimed localization of the fusion protein. As already indicated and discussed above, said advantageous localization enables the visualization of cell-cycle progression in all cell types. Said wild-type destruction signal may be embedded in the protein's full-length amino acid sequence. In this context, a full-length protein sequence generally refers to the protein's wild-type amino acid sequence including, but not limited to, any kind of known or putative isoforms or splice-variants that may comprise or may not comprise various post-translational modifications.

Alternatively, said wild-type destruction signal may also be functionally linked to a fragment of said protein, provided that said fragmentation does not prevent the advantageous localization.

It is therefore, in another aspect of the present invention, also included that the wild-type destruction signal is not part of the protein of interest, but instead operatively linked to the fluorescence reporter protein. In this case, it has further to be ensured that the nucleic acid expression construct of the present invention encodes a localization signal that directs the reporter protein linked to the wild-type destruction signal to the claimed specific subcellular localization. Therefore, in another embodiment, the fusion protein encoded by the nucleic acid construct of the present invention includes the reporter protein, the wild-type destruction signal and a localization signal directing the fusion protein to the subcellular structures as indicated. This localization signal may also be a nuclear localization signal (NLS).

The wild-type destruction signal triggers the degradation of the fusion protein. The spatiotemporal dynamics of cell-cycle progression largely depend on the oscillating expression and rapid degradation of protein factors which are involved in cell cycle control. In this context, the process of protein degradation—which is triggered by ubiquitin-mediated proteolysis—plays a key regulatory function, the irreversible nature of which is the heart of the unidirectional progression through the cell cycle program.

The ubiquitin-transfer reaction is catalyzed by enzymes known as ubiquitin ligases. Two ubiquitin E3-ligase complexes, termed SCF (Skp1/CUL1/F-box protein) and APC/C (anaphase promoting complex/cyclosome) control the time transitions of cell cycle phases by promoting the degradation of many key cell cycle regulators. While the SCF complex mainly functions in late G1, S, G2, and early M phases, the APC/C regulates mitosis including methaphase-anaphase transition and mitotic exit (as described in Li and Zhang, Cell Division, 4:2, 2009).

APC/C-dependent degradation of cyclin A allows cells to progress from prophase to methaphase, and the degradation of securing by the APC/C triggers the chromosome separation and anaphase onset. The APC/C is a large complex of 1.5 MDa composed of at least 11 core subunits which is conserved from yeast to humans and relies on two adaptor proteins, namely Cdc20 and Cdh1, to bring in substrates. Both $APC^{Cdc20}$ and $ACP^{Cdh1}$ are implicated in the control of mitosis through mediating ubiquitination and degradation of important mitotic regulators including, but not limited to, cyclin B1, securin, and Polo like kinase 1 (Plk1). Late in anaphase, the destruction of cyclin B1 leads to the inactivation of the Cdk1 kinase activity and exit from mitosis.

In the context of the present invention, the improved effect of the reporter protein provided herein as compared to the reporter proteins known in the art largely depends on the degradation of the expressed fusion protein during late M phase, for example, during and after cell division. That is, the reporter protein of the present invention is degraded at the end of M phase, and thus does not accumulate is cells after cell division when (over)expressed.

In an embodiment, the fusion protein encoded by the nucleic acid expression construct of the present invention can, for example, be a substrate of cell cycle-dependent ubiquitin E3-ligases.

A "substrate of cell cycle-dependent ubiquitin E3-ligases" as referred to herein means that the fusion protein of the present invention is targeted for ubiquitin-mediated proteolysis during cell cycle progression, for example, at late M-phase and early G1-phase, or for example, during cytokinesis. Cell-cycle dependent ubiquitin E3-ligases of the present invention include any kind of ubiquitin ligase complexes known to a person skilled in the art that specifically control cell cylce and/or cell cylce progression in mammalian cells, examples of which include, but are not limited to the mammalian APC/C (anaphase promoting complex/cylcosome) or the SCF (SKp1/CUL1/F-box protein).

In an embodiment, the fusion protein encoded by the nucleic acid expression construct of the present invention can, for example, be a substrate of the mammalian APC/C (anaphase promoting complex/cyclosome). The fusion protein encoded by the nucleic acid expression construct of the present invention can, for example, be a substrate of $APC/C^{Cdh1}$.

A large number of mitotic regulators are proteolytically degraded at the end of mitosis as substrates of the $APC/C^{Cdh1}$ (as described in Li and Zhang, Cell Division, 4:2, 2009). These include, but are not limited to, Aurora A kinase, Aurora B kinase, anillin, Polo-like kinase 1 (Plk1), protein regulator of cytokinesis 1 (PRC1), CKAP2, cyclin B1, and cyclin A.

The term "a functionally active fragment or derivative" as used in the context of the present invention generally refers to any kind of protein that comprises the amino acid sequence of the naturally occurring protein, but in any partially, substituted or modified form. A functionally active fragment or derivative of the protein of the present invention can be obtained by sequence alterations in the protein (e.g. by one or more amino acid deletions, substitutions and/or additions), wherein the protein with the sequence alterations retains a function of the unaltered protein, namely its ability to localize during cell cycle progression to subcellular structures selected from the group consisting of the cell cortex, the contractile ring, and the midbody, or to function as a fluorescence reporter protein. Such sequence alterations can include, but are not limited to, conservative substitutions, deletions, mutations and/or insertions.

Moreover, a functionally active derivative of the present invention might comprise one or more modified amino acids including, but not limited to, e.g. phosphorylated, acetylated, ubiquitinated, and/or sumoylated residues. A functionally active derivative of the present invention might further encompass any sort of chemical label such as, e.g., fluorescence-labeled moieties. A functionally active fragment or derivative of the protein can be identified and biologically characterized by means of standard assays, for example, in which the subcellular localization of the protein is determined by fluorescence imaging methods. Such methods are known in the art and, e.g., described in Sakaue-Sawano et al., Cell 132, 487-498, 2008. The term "functionally active derivative" further includes any kind of naturally-occurring allelic variants, as well as mutants or any other non-naturally occurring variants. An allelic variant is an alternate form of a (poly) peptide that is characterized as having a substitution, deletion, or addition of one or more amino acids that does essentially not alter the biological function of the polypeptide.

Furthermore, a functionally active fragment or derivative of the protein of the present invention may be fused to an epitope tag which provides an epitope to which an anti-tag substance can selectively bind. The epitope tag may be placed at the amino- or carboxyl-terminus of the peptide, but may also be incorporated as an internal insertion or substitution as the biological activity permits. The presence of such epitope-tagged proteins can be detected using a substance such as an antibody against the tagged peptide. Also, provision of the epitope tag enables the peptide to be readily purified by affinity purification using an anti-tag antibody or another type of affinity matrix that binds to the epitope tag. Various tag polypeptides and their respective antibodies are known in the art. Examples include poly-histidine (poly-his), poly-histidine-glycine (poly-his-gly) tags, the HA tag polypeptide, the c-myc tag, the Strep tag and the FLAG tag.

A functionally active fragment or derivative of the present invention can further be characterized by structural features. Accordingly, in an embodiment of the present invention, the functionally active fragment can, for example, consist of at least 60%, for example, at least 70%, for example, at least 80%, for example, at least 90%, for example, 95%, or, for example, 99% of the naturally occurring protein. The percentage of sequence identity can be determined by sequence alignment. Methods for sequence alignment for the purpose of sequence comparison are known in the art. Various programs and alignment algorithms have been described in, for example, in Pearson and Lipman, Proc. Natl. Acad. Sci. USA, Vol. 85 (8), 2444-8, 1988. In addition, the NCBI Basic Local Alignment Search Tool (BLAST) (as described in Altschul, S. F. et al., J. Mol. Biol., 215(3), 403-410, 1990) is available from several sources, including the National Center for Biotechnology Information (NCBI, Bethesda, Md.) and the Internet, for use in connection with the sequence analysis programs blastp, blastn, blastx, tblastn and tblastx.

As detailed above, an aspect of the present invention was the provision of a nucleic acid expression construct encoding a detectable reporter protein, wherein said reporter protein localizes to specific subcellular structures during cell cycle progression, and wherein said localization is indicative for cell cycle progression. The visualization of cell cycle progression according to the present invention, for example, the progression through M phase, is, e.g., illustrated in FIGS. 1, 2, and 11.

The term "cell cycle progression" as referred to in the context of the present invention generally means the two central subsequent events of the cell cycle, namely the replication of DNA (S-phase), followed by the chromosome segregation and cell division of the phase of mitosis (M-phase). It relates to the five distinct phases of the cell cycle: G1-phase, S-phase, G2-phase (also commonly known as interphase), and M-phase. The M-phase is itself composed of two tightly coupled processes: i) mitosis, in which the cell's chromosomes are divided between the two daughter cells, and ii) cytokinesis, in which the cell's cytoplasma divides and subsequently forms distinct cells. Mitosis itself is divided in five distinct stages. These five stages—prophase, prometaphase, metaphase, anaphase, and telophase—occur in strict sequential order, while cytokinesis begins in anaphase and continues through telophase. During prophase, the replicated chromosomes condense in step with the reorganisation of the cytoskeleton. In metaphase, the chromosomes are aligned at the equator of the mitotic spindle, and in anaphase they are segregated to the poles of the spindle. Cytoplasmic division is completed by the end of telophase, when the nucleus and cytoplasm of each of the daughter cells return to interphase. Activation of each phase is dependent on the proper progression and completion of the previous one. After cell division, each of the daughter cells is in the interphase, awaiting the round of a new cycle. Cells that have temporarily or reversibly stopped dividing entered quiescence, termed the G0 phase. Although the various stages of interphase are usually not morphologically distinguishable, each phase of the cell cycle has a distinct set of specialized biochemical processes that prepare the cell for initiation of a new round of cell division.

The nucleic acid expression construct of the present invention is suitable to visualize the transition from M to G1 phase during cell cycle progression, i.e. late M phase and cell division, processes which are significantly characterized by defined morphological changes.

In animal cells and many unicellular eukaryotes, the cell cycle culminates in the division of the cytoplasma by cytokinesis. The structure that accomplished cytokinesis is the contractile ring. The contractile ring is a dynamic assembly composed of actin and myosin II filaments, including many structural and regulatory proteins. During cytokinesis, the cytoplasm of a cell is divided in two by a contractile ring, which pinches the cell in two to create two daughter cells with one nucleus each, thereby creating a cleavage furrow. The contractile ring assembles beneath the plasma and contracts to constrict the cell into two. The central problem for a cell undergoing cytokinesis is to ensure that it occurs at the right time and in the right place. Cytokinesis must not occur too early in M-phase, or it will disrupt the path of the separating chromosomes. It must also occur at the right place to separate the two segregating sets of chromosomes properly so that each of the daughter cell receives a complete set. In animals, the contractile ring invariably forms in the plane of the metaphase plate, at right angles to the long axis of the mitotic spindle, thereby ensuring that division occurs between the two sets of separated chromosomes. Moreover, the fully assembled contractile ring may further contain any kind of proteins in addition to actin and/or myosin II. The contractile ring is finally dispensed when cleavage ends, since the plasma membrane of the cleavage furrow narrows to form the midbody. In some cell types such as hepatocytes or cardiomyocytes variations of the cell cycle such as acytokinetic mitosis or endoreduplication take place in which contractile rings or midbodies do not form.

In the context of the present invention, the fusion protein encoded by the nucleic acid expression construct provided herein highlights subcellular structures in individual live cells that are characteristic for cell cycle progression at the stage of late M phase including the process of cell division, namely the cell cortex, the contractile ring and the midbody during late M phase. As explained above, this effect may, for example, be due to the fact that the protein containing the wild-type destruction signal localizes to said subcellular structures.

Alternatively, the fusion protein may contain a localization signal that directs the fusion protein to the subcellular structures.

The term "cell cortex" as referred to herein generally refers to structures which are constituted of spectrin proteins and actin microfilaments. Spectrin proteins and actin microfilaments are attached to transmembrane proteins by attachment proteins between them and the transmembrane proteins. The cell cortex is attached to the inner (cytosolic) face of the plasma membrane in cells where the spectrin proteins and actin microfilaments form a mesh-like structure which can be broken and reformed. This breakage and reformation is referred to as dynamic instability. The cell cortex functions as a mechanical support of the plasma membrane, and can be visualized by means of fluorescence analysis. The visualization of a contractile ring by means of fluorescence readout according to the present invention is, e.g., illustrated in FIG. 1.

Moreover, the term "contractile ring" as referred to in the context of the present invention refers to any cellular structure formed during the process of cytokinesis and which morphologically indicates cell division, e.g. by localizing to the area of the cleavage furrow. The contractile ring of the present invention refers to cellular structures comprising actin filaments, for example, to actin filaments with incorporated scaffold proteins such as, e.g., anillin (as described in Zhao and Fang, Journal of Biological Chemistry Vol. 280, 33516-33524, 2005). Moreover, the contractile ring of the present invention may further contain any kind of additional proteins in addition to actin and myosin II. A contractile ring can be visualized as a subcellular structure in the area of the cleavage furrow by means of fluorescence analysis, including, but not limited to, direct fluorescence analysis, indirect immunofluorescence analysis, or methods of life cell imaging such as, e.g., time-lapse video microscopy. These methods are known to the person skilled in the art and are described, for example, in Kosodo et al., EMBO Journal 27, 3151-3163, 2008 and in Dubreuil et al., J. Cell Biol., Vol. 176, 483-495, 2007.

The term "midbody" as used in the context of the present invention refers to any kind of transient structure which is formed during the final stages of cell division, and which persists as a tether between the two daughter cells. A midbody may contain the remains of the central spindle composed of tightly packed microtubules. The midbody of the present invention may also include all kind of subcellular structures which remain on the inside of the plasma membrane of each cell after the daughter cells have completely separated, where they may serve as a mark on the cortex that helps to orient the spindle in the subsequent cell division. The midbody of the present invention also includes the cytoplasm containing the remaining of the central spindle by which the daughter cells remain attached before cell division is complete. Visualization of the midbody can be accomplished by means of standard methods known in the art including, e.g., immunofluorescence or live cell imaging methods and is described, for example, in Dubreuil et al., J. Cell Biol., Vol. 176, 483-495, 2007. The visualization of the midbody upon expression of the reporter protein according to the present invention is illustrated in, e.g., FIGS. 1 and 11 and described in Example 1.

In an embodiment of the present invention, the fusion protein can, for example, localize during cell cycle progression to the midbody.

Anillin, Aurora B kinase, Polo-like kinase 1 (Plk1), and protein regulator of cytokinesis 1 (PRC1) are suitable in the context of the present invention for visualizing cell cycle progression in individual cells when fused to a reporter protein of interest, because all of these proteins localize to the midbody.

In an embodiment, the nucleic acid expression construct of the present invention can, for example, encode a fusion protein comprising a protein with a wild-type destruction signal wherein said protein is selected from the group consisting of anillin, Aurora B kinase, Polo-like kinase 1 (Plk1), and protein regulator of cytokinesis 1 (PRC1).

In the context of the present invention, it has surprisingly been found that anillin is suitable to visualize cell cycle progression since (over)expression of this protein under the control of a non-endogenous promoter does not cause multinucleation and a concomitant increase in centrosome numbers. In contrast to a previous report (as described in Zhao and Fang, Journal of Biological Chemistry Vol. 280, 33516-33524, 2005), (over)expression of anillin was found not to result in toxic effects due to protein accumulation based on the protein's rapid and complete degradation at the end of M phase.

The term "anillin" as used herein generally means the actin-binding protein described in the art (for example, in Field, C. M. and Alberts, B. M., J. Cell Biol. 131, 165-178, 1995) with an essential function in cytokinesis, and which localizes at the cleavage furrow during cell cycle progression. The protein anillin of the present invention is, for example, a substrate of the anaphase-promoting complex/cyclosome that controls spatial contractility of myosin during late cytokinesis. The structure and function of anillin has been described in the art, and anillin has been demonstrated to localize to the cell cortex, the midbody, and to the contractile ring (as described, for example, in Zhao and Fang, Journal of Biological Chemistry Vol. 280, 33516-33524, 2005, Dubreuil et al., J. Cell Biol., Vol. 176, 483-495, 2007, and FIG. 1).

The mechanisms of cell-cycle control and cell cycle progression are conserved in a wide range of eukaryotic organisms including human, animal, fungi, and plants. Functional orthologs of a large number of mitotic regulators have been identified and characterized in a variety of model systems, including, but not limited to, human, mouse, flies (e.g. *Drosophila melanogaster*), yeast (e.g. *Saccharomyces cerevisiae*), and plants (e.g. *Arabidopsis thaliana*).

In an embodiment, the nucleic acid expression construct of the present invention can, for example, encode a fusion protein comprising a reporter protein and a protein with a wild-type destruction signal, wherein said protein with a wild-type destruction signal is derived from human, animal, fungi, or plant.

In an embodiment, the nucleic acid expression construct of the present invention can, for example, comprise or consists of a DNA cassette with the nucleic acid sequence of SEQ ID NO: 1 (see FIG. 10).

The nucleic acid sequence of SEQ ID NO: 1 encodes the CMV early enhancer/chicken β-actin promoter (CAG) promoter operably linked to a nucleic acid sequence encoding a fusion protein comprising EGFP (enhanced green fluorescence protein) and wild-type mouse anillin.

In an embodiment, the nucleic acid expression construct of the present invention can, for example, comprise or consist of a DNA cassette encoding the sequence of EGFP (enhanced green fluorescence protein) and mouse anillin operably linked to a cell-type specific promoter, for example, wherein said sequence is operably linked to the cardiomyocyte-specific α-MHC-promoter.

In an embodiment, the present invention provides a method of visualizing cell cycle progression, characterized in that said method comprises the steps of a) introducing a nucleic acid expression construct according to the present invention into a cell;

b) expressing the fusion protein encoded by the nucleic acid expression construct within the cell;

c) monitoring the expression of the fusion protein by taking advantage of the reporter protein.

In this respect, the term "visualizing cell cycle progression" as used herein means that the different phases of the cell cycle (i.e. G1, S, G2, and M phase), for example, the phases of mitosis (M-phase) and cytokinesis, are investigated by means of visual inspection. The visual inspection of cells undergoing cell cycle progression, for example, the transition from M to G1 phase or from G1 to S phase, may be carried out by a variety of standard methods including, but not limited to, fluorescence light microscopy and/or cell sorting. Such methods are known to the person skilled in the art and are described, for example, in as described in Sakaue-Sawano et al., Cell 132, 487-498, 2008 and Kosodo et al., EMBO Journal 27, 3151-3163, 2008). The visualization of cell cycle progression according to the present invention is exemplified in, e.g., Examples 1, 2, or 5.

The term "expressing" or "expression" as used herein generally mean allowing or causing the information in a gene or a DNA sequence to become manifest. In the context of the present invention, it means, for example, the intracellular production of the protein encoded by the nucleic acid expression construct of the present invention by activating the cellular functions involved in transcription and translation of the corresponding gene or DNA sequence. That is, a DNA sequence is expressed in or by a cell to form an "expression product" such as a protein. In the context of the present invention, said expression product can, for example, refer to the fusion protein encoded by the nucleic acid expression construct of the present invention. The expression of a protein in or by a cell may depend on a variety of factors, including, but not limited to, the promoter sequence which is operably linked to the DNA sequence encoding the protein of interest, the presence or absence of enhancer and/or silencer sequences or other DNA sequences which control the rate of transcription, the cell culture conditions applied to the cell carrying the respective DNA sequence including the media used for culturing the cell, and/or the number of copies of DNA sequences introduced into the cell. Successful expression of the fusion protein may be analyzed and/or visualized by standard methods known to the person skilled in the art, including, but not limited to, Western Blot analysis, Northern Blot analysis, RNase protection assays, quantitative RT-PCR, as well as methods concerning direct or indirect fluorescence readout. Such methods are, e.g., described in Sambrook, 2000 (Molecular Cloning: A laboratory manual, Third Edition).

The terms "introducing" or "introduction" of a nucleic acid expression construct as used herein generally include all methods known in the art that are appropriate to transfer a nucleic acid sequence into a cell, for example, into a host cell in which expression of the fusion protein encoded by the nucleic acid expression construct is desired. These methods may include, but are not limited to, transfection, transformation, transduction, electroporation and microinjection, and are, e.g., described in Sambrook et al., 2000. In the context of the present invention, the terms "introducing" or "introduction" can, for example, refer to the transfection of a nucleic acid sequence into a host cell, for example, to the transfection of a mammalian cell. Transfection of animal cells typically involves opening transient pores or 'holes' in the cell plasma membrane, to allow the uptake of material. Nucleic acids sequences (such as supercoiled plasmid DNA or siRNA contructs), or even proteins such as antibodies, may be transfected. In addition to electroporation, transfection can be carried out using calcium phosphate, or by mixing a cationic lipid with the material to produce liposomes, which fuse with the cell plasma membrane and deposit their cargo inside. The nucleic acid sequence introduced into a host cell can be derived from any kind of source, including cells of the same genus or species as the host cell, or cells of a different genus or species.

The nucleic acid expression construct according to the present invention may be either transiently or stably introduced into the cell.

"Transiently introduced" as referred to herein means that the transfected gene of interest is only temporarily expressed in the cell. Since the DNA which is transiently introduced into the cell is usually not inserted into the nuclear genome, the foreign DNA is lost at the later stage when the cells undergo mitosis.

"Stably introduced" as referred to herein means any kind of stable gene transfer in which a nucleic acid encoding a gene of interest is introduced into a target cell as such that it is stably integrated into the genome of said cell. Stable gene transfer can be carried out by diverse standard methods known to the person skilled in the art including, but not limited to, the use of viral vectors for expression in both dividing and non-dividing cells. Stable gene transfer is mostly accompanied by the co-introduction of a selection gene that confers resistance toward a certain substance, e.g., a certain toxin. Examples of these substances include Geneticin, also known as G418, which is a toxin that can be neutralized by the product of the neomycin resistant gene. If the toxin, towards which the co-transfected gene offers resistance, is then added to the cell culture, only those few cells with the foreign genes inserted into their genome will be able to proliferate, while other cells will die. After applying this selective selection procedure for some time, only the cells with a stable transfection remain and can be cultivated further.

In the context of the present invention, is has surprisingly been found that cell cycle progression can be visualized at a high contrast for a time period of one or more cell cycle(s) when the nucleic acid expression construct of the present invention is stably introduced into the target cell(s).

In an embodiment, the method of the present invention is further characterized in step a) in that the nucleic acid expression construct is, for example, stably introduced into the cell.

Vectors based on retrovirus and lentivirus backbones have revolutionized the ability to transfer genes into primary cells. These vectors allow for extensive ex vivo and in vivo studies following introduction of a gene of interest into a cell, and can been used clinically in individuals suffering from cancers, infections, and genetic diseases. Ex vivo lentiviral gene transfer can result in efficient transduction of progenitor cells (>80%) that can then be further differentiated into lineage cells. Alternatively, differentiated cells can themselves be transduced ex vivo with lentiviral vectors. Lentiviral-based gene expression can be used to efficiently deliver a gene of interest to mammalian cells in culture or in vivo, and provides a stable, long-term expression of the target gene both in dividing and non-dividing cells. Once the lentivirus has entered the target cell, the viral RNA is reverse-transcribed, actively imported into the nucleus, and stably integrated into the genome. After the lentiviral construct has integrated into the genome, expression of the transferred gene can be assayed by standard methods or, alternatively, antibiotic selection can be used to generate a stable cell line for long-term expression studies. Viral transduction according to the present invention may further include traditional Moloney Leukemia Virus (MoMLV)-based retroviral and Adenoviral-based systems.

Viral systems for gene transfer into mammalian cell have been described in the art (for example, in Naldini, L., Curr. Opin. Biotechnol. 9, 457-463, 1998), and are commercially available from diverse source (e.g. Invitrogen™, Carlsbad, Calif., USA). A nucleic acid expression construct according to the present invention which has been successfully used for lentiviral transduction of primary cardiomyocytes is, e.g., described in Example 5 and further illustrated in FIG. 7.

In an embodiment, the method of the present invention is further characterized in step a) in that the nucleic acid expression construct can, for example, be introduced into a cell by means of viral transduction, for example, by means of lentiviral transduction.

Since there is a need to better understand the molecular mechanisms underlying cell cycle control in humans and animals including, e.g., the processes of wound healing and/or the mechanisms underlying loss of cell cycle control in diseases such as cancer, the insight of cell cycle progression can, for example, be analysed in mammalian cells in the context of the present invention. That is, the nucleic acid expression construct of the present invention can, for example, be introduced into a mammalian cell derived from a mammalian cell line. The mammalian cell can, for example, be selected from the group consisting of stem cells, primary cardiomyocytes, primary fibroblasts, embryonic chimaeras, HEK 293 cells, and Hela cells. The successful introduction of the nucleic acid expression construct provided herein into mammalian cells including visualization of cell cycle progression is, e.g., exemplified in Examples 1, 2, and 5.

In an embodiment, the method of the present invention can be further characterized in step a) in that the cell can, for example, be derived from a mammalian cell, for example, in that the mammalian cell line is selected from the group consisting of stem cells, primary cardiomyocytes, primary fibroblasts, embryonic chimaeras, HEK 293 cells, and Hela cells.

The term "stem cells" as used herein generally includes, but is not limited to, any kind of human and non-human embryonic stem (ES) cells, adult stem cells, and induced pluripotent stem cells (iPS cells). That is, the stem cells used in the context of the present invention may be pluri-, toti- or multipotent. ES cells according to the present invention include human and non-human stem cells derived from the inner cell mass of an early stage embryo known as a blastocyst. ES cells are pluripotent and can be grown in culture. That is, they are able to differentiate into all derivatives of the three primary germ layers: ectoderm, endoderm, and mesoderm. These include each of the more than 220 cell types in the adult body they derived from. Pluripotency distinguishes ES cells from multipotent progenitor cells found in the adult; these only form a limited number of cell types. When given no stimuli for differentiation, (i.e. when grown in vitro), ES cells may maintain pluripotency through multiple cell divisions. Stem cells according to the present invention also include pluripotent stem cells which have been generated from adult fibroblast cultures (iPS=induced pluripotent stem cells), a procedure which has recently been described as an alternative method for generating stem cells (in Takahashi and Yamanaka, Cell 126, 663-676, 2006). The generation, differentitation and growth conditions of ES cells are known in the art and are described, for example, in Wobus et al., Differentiation, 48, 173-82, 1991. ES cell differentiation according to the present invention is, e.g., exemplified in Example 3 and 10.

In an embodiment of the present invention, the stem cells can, for example, be selected from the group consisting of embryonic stem (ES) cells, adult stem cells, and induced pluripotent stem (iPS) cells.

The term "cardiomyocytes" as referred to herein generally include cells derived from cardiac muscle tissue. The cardiac muscle is a type of involuntary striated muscle found in the walls of the heart, specifically the myocardium. Cardiac muscle is one of three major types of muscle, the others being skeletal and smooth muscle. The cells that comprise cardiac muscle are sometimes seen as intermediate between these two other types in terms of appearance, structure, metabolism, excitation-coupling and mechanism of contraction. Cardiac muscle shares similarities with skeletal muscle with regard to its striated appearance and contraction, with both differing significantly from smooth muscle cells. Cardiomyocytes of the present invention also include primary cardiomyocytes derived from E13.5 mouse embryos. The isolation and culturing of cardiomyocytes according to the present invention is known in the art, and e.g. exemplified in the Examples provided herein.

Human Embryonic Kidney 293 cells, also referred to as HEK 293 cells, are a specific cell line originally derived from human embryonic kidney cells grown in tissue culture. HEK 293 cells are very easy to grow and transfect very readily and have been widely-used in cell-biology research for many years. They are also used by the biotechnology industry to produce therapeutic proteins and viruses for gene therapy. HEK 293 cells have been described in the art and are, e.g., commercially available from the American Type Culture Collection (ATCC, USA).

HeLa cells as refers to herein include any sort of immortal cell line derived from cervical cancer and taken from Henriette Lacks, who died from her cancer on Oct. 4, 1951. The Hela cells of the present invention include all Hela cell lines known to the person skilled in the art and commercially obtainable, e.g. from the American Type Culture Collection (ATCC, USA).

Moreover, in the context of the present invention, the term "embryonic chimaeras" refers to cells which have been generated by diploid aggregation of morula-stage embryos with embryonic stem (ES) cells derived from stage E8.5 and E10.5 mouse embryos. In an embodiment of the present invention, the embryonic chimaeras can, for example, be generated by the aggregation of embryonic stem (ES) cells expressing EGFP-anillin with wild-type morula-stage embryos. The generation of embryonic chimaeras is, e.g., exemplified in Example 6 of the present invention.

The term "monitoring" as used herein generally refers to the visual inspection of a cell of interest. Monitoring according to the present invention means, for example, the visualization of the expression of the fusion protein with the help of the reporter protein.

In an embodiment, the method of the present invention is further characterized in step c) in that the expression of the fusion protein can, for example, be monitored by means of fluorescence, luminescence and/or enzymatic analysis.

In the context of the present invention, the visualization of cell cycle progression has been carried out by means of fluorescence analysis.

The term "fluorescence analysis" as used herein generally refers to all sorts of imaging methods known in the art that are suitable to visualize, detect, analyze and/or quantify the expression of the fusion protein encoded by the nucleic acid expression construct of the present invention within a cell. Fluorescence analysis according to the present invention includes, but is not limited to, all known methods of deconvolution and confocal fluorescence microscopy, for example, methods concerning the in vivo imaging of the fusion protein such as, e.g., time-lapse microscopy and/or live cell imaging, methods concerning the in vitro imaging of the fusion protein including, e.g., direct or indirect procedures of immunocytochemistry and/or immunofluorescence characterized by the use of either primary or secondary marker-coupled antibodies directed against the protein of interest, as well as methods concerning multiple-fluorescent-probe microscopy. Commonly used marker molecules that may be covalently coupled to a secondary antibody for use in immunofluorescence analysis may include, but not limited to, fluorescent dyes such as fluorescein, rhodamine, Cy3, Cy5, and Alexa 568 or alike. Such fluorescent dyes are known to the person skilled in the art and can, e.g., be purchased from various suppliers including, e.g., Invitrogen™ (CA, USA). Fluorescence analysis according to the present invention also includes all known methods of stimulated emission depletion (STED) microscopy. The visualization of fluorescence proteins in subcellular structures by means of STED microscopy is known to the person skilled in the art and has, e.g., been described in Hein et al., 2008, Proc. Natl. Acad. Sci. USA, Vol. 105, 14271-14276, 2008. Fluorescence analysis according to the present invention is exemplified in Examples 1 to 14.

The fluorescence analysis according to the present invention further includes flow cytometry. The term "flow cytometry" as used herein includes all methods suitable to determine the cell cycle status of cell populations using fluorescent dyes, characterized in that the fluorescent dyes stain the DNA content of cell nuclei. Flow cytometry yields quantitative information on the DNA content of cells and hence allows determination of the relative numbers of cells in the G1, S and G2, and M phases of the cell cycle. Flow cytometry techniques are known to the person skilled in the art and are carried out by standard methods in a total cell population that is examined in one sample. Flow cytometry as referred to in the context of the present invention is, e.g., exemplified in Example 2.

The term "luminescence analysis" as used herein generally refers to all methods known in the art that are suitable to visualize, detect, analyze and/or quantify the emission of light in correlation to an analyte concentration including, but not limited to, photoluminescence, bioluminescence and chemiluminescence. Luminescence is light that accompanies the transition from an electronically excited atom or molecule to a lower energy state. The forms of luminescence are distinguished by the method used to produce the electronically excited species. Methods for in vitro luminescence analysis are known in the art and detection systems can be purchased, e.g., from Promega™ (Madison, Wis., USA). Methods for in vivo luminescence analysis in animals after i.p. injection of d-luciferin with sensitive CCD video cameras are known in the art and are commercially available (e.g. Xenogen, USA).

The term "enzymatic analysis" generally refers to any kind of enzyme-based assay known in the art which is applicable to detect a reporter protein of interest and includes, but is not limited to, the detection of beta-galactosidase by enzymatic reaction. The detection of beta-galactosidase by enzymatic methods is standard knowledge to the person skilled in the art.

In certain embodiments, the expression of the reporter protein within a cell of interest may be continuously monitored for a certain period of time. This period of time may include several hours, for example, a time period of at least 14 hours, but may also refer to a time period of several days or more. During this time, the cell(s) is/are expected to undergo at least one or more rounds of cell cycles. Furthermore, the cell(s) may also undergo multiple or even an unlimited number of cell cycles. The expression of the reporter protein can further be monitored by visual inspection of the cell(s) at defined time points over a certain period of time in which the cell(s) can, for example, undergo at least one round of cell cycle. The monitoring of protein expression can, for example, takes place before, during and after nuclear breakdown. This period of time may vary from cell type to cell type and thus depends on the precise type of cell or cell population analyzed. The monitoring of cell cycle kinetics according to the present invention is, e.g., exemplified in FIG. 1, FIG. 11 and Table 1.

In an embodiment, the method of the present invention is further characterized in step c) in that the expression of the fusion protein can, for example, be monitored for a time period of one or more cell cycle(s).

Reagents for counting cells and quantitating cell proliferation are valuable research and diagnostic tools. Currently, however, there is no detectable reagent that can be specifically incorporated into cells during cell division and which can be directly detected on a single cell basis. Consequently, most cell proliferation assays known in the art estimate the number of cells either by incorporating 3H-thymidine or 5-bromo-2-deoxyuridine (BrdU) into cells during proliferation, by metabolic activity such as ATP production, or by measuring total nucleic acid or protein content of lysed cells.

Accordingly, there is always a need for an improved agent which can be used as a marker for cell cycle progression and, therefore, as a proliferation marker in either living of fixed cells.

In the context of the present invention, it has surprisingly been found that cell cycle progression in eukaryotic cells, for example, in mouse embryonic stem (ES) cells, can be easily visualized on a single cell basis by monitoring the expression of the fluorescence reporter protein encoded by the nucleic acid expression construct of the present invention.

In an embodiment, the present invention provides the use of the nucleic acid expression construct according to the present invention as a cell proliferation marker in vivo or in vitro.

The term "cell proliferation marker" as used herein generally refers to any sort of molecule which presence or absence within a cell or on a cell's surface is indicative for ongoing cell proliferation, cell cycle progression and/or mitotic activity. In the context of the present invention, a cell proliferation marker is the fusion protein encoded by the nucleic acid expression construct of the present invention. That is, the fusion protein of the present invention can serve as a cell proliferation marker since its expression can be readily detected in proliferating cells, while it not detectable and/or readily visible in resting, non-proliferating, or post-mitotic cells. Accordingly, the expression of the fusion protein of the present invention is indicative for mitotic activity, and thus serves as a marker for cell cycle progression and mitotic activity in either living or fixed cells. Examples of cell proliferation markers known in the art include, but are not limited to, pHH3 and Ki-67. Ki-67, for example, is a nuclear antigen detectable in G1, S, G2, and M phases, but not in G0, which represents a widely accepted cell proliferation marker in the art (as described, for example, in Endl and Gerdes, ExpCell Res. 257, 231-237, 2000). The cell proliferation marker of the present invention may co-localize with these known proliferation markers, and may further refer to all proteins with an essential role in cell proliferation which are present and thus detectable in dividing cells of normal and abnormal tissues including, e.g., cancer tissues.

Furthermore, the fusion protein of the present invention localizes to subcellular structures selected from the group consisting of the cell cortex, the contractile ring, and the midbody during cell cycle progression and is therefore indicative for cell division. Accordingly, the cell cycle proliferation marker of the present invention enables to distinguish acytokinetic mitosis and endoreduplication from cell division.

In the context of the present invention, the reporter protein encoded by the nucleic acid expression construct of the present invention has been successfully demonstrated to co-localize with Ki-67 and pHH3, as exemplified in Example 3.

In an embodiment, the use of the nucleic acid expression construct as a proliferation marker according to the present invention is characterized as such that the expression of the fusion protein encoded by the nucleic acid expression construct can, for example, be indicative for mitotic activity.

In the context of the present invention, the term "indicative for mitotic activity" means that the expression of the fusion protein encoded by the nucleic acid expression construct of the present invention, and accordingly its cell biological visualization within the cell, takes place during cell cycle progression, for example, during M phase. The term "indicative for mitotic activity" further means that the fusion protein is degraded during late M phase and is thus no longer visible for fluorescence inspection, thereby indicating the exit of mitosis and/or the status of postmitotic and non-proliferating cells.

In an embodiment, the use of the nucleic acid expression construct according to the present invention is characterized in that the localization of the fusion protein encoded by the nucleic acid expression construct to the contractile ring or midbody can, for example, be indicative for the formation of two daughter cells.

In an embodiment, the present invention provides the use of the nucleic acid expression construct according to the present invention for distinguishing between cell division and acytokinetic mitosis and/or endoreduplication in vivo or in vitro.

The terms "acytokinetic mitosis" and "endoreduplication" as used herein are terms of general knowledge to a person skilled in the art.

In an embodiment, the use of the nucleic acid expression construct according to the present invention is characterized in that the nucleic acid expression construct can, for example, be introduced into a cell population or into a living organism, for example, into embryonic stem (ES) cells or primary cells.

In the context of the present invention, the feasibility of the provided reporter system as a proliferation marker has been investigated in cell populations consisting of proliferating and postmitotic cells. A nucleic acid expression construct according to the present invention encoding a fluorescence reporter protein under the control of the CAG promoter has been shown to be useful. The use of said nucleic acid expression construct as a proliferation marker in embryonic stem (ES) cells as well as during mouse embryogenesis is, e.g., exemplified in Example 3.

As detailed above, in the context of the present invention, embryonic stem cells (ES cells) are found to be suitable to analyse cell cycle progression in differentiating cells. Because of their plasticity and potentially unlimited capacity for self-renewal, ES cell therapies have been proposed for regenerative medicine and tissue replacement after injury or disease. However, to date, no approved medical treatments have been derived from embryonic stem cell research. Adult stem cells and cord blood stems cells have so far been the only stem cells used to successfully treat any diseases.

Therefore, an aspect of the present invention was to provide a transgenic animal carrying the nucleic acid expression construct of the present invention for the analysis of cell cycle proliferation in vivo.

In an embodiment, of the present invention provides a transgenic animal comprising the nucleic acid expression construct according to the present invention.

The term "transgenic animal" as used herein generally refers to an animal that carries a foreign gene that has been deliberately inserted into its genome. This foreign gene which is encoded by a nucleic acid sequence is introduced into the animal using recombinant DNA technology, and must then be transmitted through the germ line so that every cell, including germ cells, of the animal contain the same modified genetic material. A transgenic animal of the present invention is a non-human animal and may be a transgenic mouse, rat, rabbit, pig, sheep, or cow. To date, there are several methods of producing transgenic animals, i.e. DNA microinjection, embryonic stem cell-mediated gene transfer, and lentiviral transduction.

DNA microinjection involves the transfer of a desired gene construct (e.g. of a single gene or of a combination of genes that are recombined and then cloned) from another member of the same species or from a different species into the pronucleus of a reproductive cell. Subsequently, the manipulated cell, which first must be cultured in vitro (i.e. not in a live animal) has to develop to a specific embryonic phase, before it is transferred to the recipient female. A major advantage of DNA microinjection is that this method is applicable to a wide variety of species. The mouse was the first animal to undergo successful gene transfer using DNA microinjection.

Embryonic Stem Cell-Mediated Gene transfer allows that the presence of transgenes can be tested at the embryonic state, and involves the isolation of totipotent stem cells (stem cells that can develop into any type of specialized cell) from embryos, the insertion of the desired gene into these cells, and the incorporation of cells containing the desired DNA into the host's embryo, resulting in a chimeric animal. This method allows testing for transgenes at the cell stage.

The tetraploid complementation approach allows for the generation of tetraploid embryos by electrofusion of two blastomeres from two-cell stage embryos (as described in Nagy et al., Proc. Natl. Acad. Sci. USA, 104, 4455-60, 2007). Replication of the genetic material followed by mitotic division results in a two-cell embryo which contains a tetraploid content of DNA. This tetraploid embryo can develop further to the blastocyst stage. Combining tetraploid blastocysts with either embryonic stem (ES) cells or diploid embryos has also become an established technique for creating mouse chimaeras with high efficiency (up to 100%). Tetraploid complementation according to the present invention is, e.g., described in Example 4.

The transgenic animal according to the present invention may be generated by any of these methods.

In an embodiment of the present invention, the transgenic animal of the present invention can, for example, be a transgenic mouse.

A "transgenic mouse" as referred to in the context of the present invention generally contains additional, artificially-introduced genetic material in every cell, for example, conferring a gain of function by expressing a new protein. The transgenic mouse of the present invention is considered to be a very useful system for studying mammalian gene function and regulation because analysis is carried out on the whole organism. The extra genetic material may be foreign DNA, but may also come from any source, including another mouse. To get the same foreign DNA sequence into every cell of the mouse, it is necessary to introduce the DNA into cells of the very early mouse embryo that will contribute to the germ line (i.e. the cells that produce eggs or sperm).

In an embodiment, the transgenic animal, for example, the transgenic mouse of the present invention comprises a gene encoding a fusion protein comprising EGFP (enhanced green fluorescence protein) and anillin, wherein the sequence encoding the fusion protein is operably linked to a constitutive promoter. Optionally, said fusion protein further comprises one or more affinity purification tag(s). A transgenic mouse according to the present invention is, e.g., exemplified in Example 11.

In an embodiment, the transgenic animal, for example, the transgenic mouse of the present invention, can comprise a gene encoding the sequence of SEQ ID NO: 1.

In an embodiment, the transgenic animal, for example, the transgenic mouse of the present invention, can comprise a gene encoding a fusion protein comprising EGFP (enhanced green fluorescence protein) and anillin, wherein the sequence encoding the fusion protein is operably linked to a cell type-specific promoter, for example, to a cardiomyocyte-specific promoter, or for example, to the cardiomyocyte-specific α-MHC-promoter.

In an embodiment, the transgenic animal, for example, the transgenic mouse of the present invention, can comprise a gene encoding a fusion protein comprising EGFP (enhanced green fluorescence protein) and anillin, wherein the sequence encoding the fusion protein is operably linked to an inducible promoter, for example, to a promoter derived from the pTet-on/pTet-off system (Clontech™, USA).

In an embodiment, the transgenic animal, for example, the transgenic mouse of the present invention, can comprise a gene encoding a fusion protein comprising EGFP (enhanced green fluorescence protein) and anillin, wherein the sequence encoding the fusion protein is operably linked to a STOP-cassette flanked by loxP sites and an ubiquitous promoter. After the addition of Cre-recombinase the STOP cassette is excised and the fusion protein gets expressed. By mating the transgenic mice harbouring the loxP flanked STOP cassette with transgenic mice expressing Cre under control of tissue specific or inducible promoters, the expression of the fusion protein gets tissue specific and/or inducible.

In an embodiment, the transgenic animal, for example, the transgenic mouse of the present invention, can comprise a gene encoding a fusion protein comprising EGFP (enhanced green fluorescence protein) and anillin, wherein the sequence encoding the fusion protein is operably linked to a cell cycle-specific promoter which is selected from the group consisting of the E2F1 promoter, the Ki-67 promoter, the PCNA promoter, and the cyclin B1 promoter, or any combination thereof.

During embryonic development, stem cells are likely to undergo an increased rate of proliferation in different organs including, but not limited to, the heart. Moreover, cardiomyocytes have been shown to even continue their proliferation during postnatal growth, although it is not yet clear to which extend and/or for how long this proliferation exactly lasts (as described in Soonpaa et al., Am J Phys, 271, H2183-9, 1996).

Accordingly, one of the main questions which arises is whether the heart bears cell type specific stem cells that are able to differentiate into cardiomyocytes during development and postnatal growth, and if so, which factors are essential to drive this differentiation. In addition, damaged heart muscle tissue, e.g., due to ischemic heart failure, could be restored through repair or regeneration. However, endogenous repair mechanism, including the presumed proliferation of cardiomyocytes under conditions of severe blood vessel stress or vessel formation and speculative tissue generation via the migration of bone-marrow-derived stem cells to the site of damage, are insufficient to restore lost heart muscle tissue, i.e. myocardium, or cardiac function. Due to the difficulty in regenerating damaged myocardial tissue, embryonic and/or adult-derived stem cells, including embryonic stem (ES) cells, myoblasts, and mesenchymal cells, have been explored to varying extents as possible sources for regenerating damaged myocardium and this for cardiac repair in animal models.

In the context of the present invention, it has been found that a transgenic animal, for example, a transgenic mouse with a gene encoding a fusion protein according to the present invention is suitable for analyzing cell proliferating in living cells and organs, especially with respect to the not yet defined proliferation rate of stem cells and/or cardiomyocytes during embryonic development and postnatal growth. Furthermore, due to the localization of the fusion protein during cell cycle progression to subcellular structures selected from the group consisting of the cell cortex, the contractile ring, and the midbody, it enables to distinguish acytokinetic mitosis and endoreduplication from cell division in cardiomyocytes. The use of a transgenic mouse according to the present invention for in vivo visualization of proliferation and/or for distinguishing cell division from acytokinetic mitosis and/or endoreduplication in cardiomyocytes is, e.g., exemplified in Example 11.

Moreover, the transgenic animal, for example, the transgenic mouse of the present invention, enables and/or facilitates the analysis of substances which successfully initiate proliferation of cardiomyocytes in the adult organism, e.g. after heart tissue damage due to ischemic heart failure or cardiomyophathy. Consequently, the transgenic animal, for example, the transgenic mouse of the present invention, enables the investigation of specific cell proliferation including the identification of proliferating stem cells or progenitor cells due the expression and visualization of the fusion protein according to the present invention in proliferating cells. The transgenic mouse of the present invention is, for example, suitable for the analysis of substances in high-throughput screening assays. To ease the identification of cardiomyocytes in such an assay, the transgenic mouse can be crossed with mice expressing a marker protein under the expressional control of a cardiac specific promoter (e.g. α-MHC-mCherry).

Accordingly, in an embodiment, the present invention provides the use of the trangenic animal according to the present invention for analyzing cell proliferation and/or distinction of cell division from acytokinetic mitosis and/or endoreduplication in vivo, for example, for analyzing cell proliferation during embryonic development, wound healing, postnatal growth, pregnancy, myocardial infarction, cardiomyophathy and/or cell replacement therapy.

The following Figures and Examples are intended to illustrate various embodiments of the present invention. As such, the specific modifications discussed therein are not to be understood as limitations of the scope of the present invention. It will be apparent to the person skilled in the art that various equivalents, changes, and modifications may be made without departing from the scope of the present invention, and it is thus to be understood that such equivalent embodiments are to be included herein.

FIGURES

FIG. 1: EGFP-anillin expression displays the endogenous localization

A: Schematic drawing of the EGFP-anillin expression construct using the ubiquitous CAG promoter. B: Colony of a stably transfected ES-cell line expressing EGFP-anillin. EGFP is predominantly located in the nucleus and in the cell cortex. C: Localization of EGFP-anillin in the nucleus, the cytoplasm, the cell cortex, or the midbody of fixed transgenic ES-cells. D: Pictures from a time-lapse movie of a dividing ES-cell in an EGFP-anillin expressing cell line. After dissolving of the nucleus, EGFP-anillin is cortically located (25', i.e. 10 minutes after dissolving of the nucleus), contributes to the contractile ring (35', i.e. 20 minutes after dissolving of the nucleus) and to the midbody eventually (40', i.e. 25 minutes after dissolving of the nucleus). After a time period of 125 minutes (125', i.e. 110 min after dissolving of the nucleus), EGFP-anillin is re-expressed in the nuclei of the daughter cells.

FIG. 2: Anillin is a mitotic marker
A: Staining of an EGFP-anillin ES-cell colony with Ki-67 and pHH3. Both proliferation markers show co-localization with EGFP-anillin. B: flow cytometric profile of an EGFP-anillin and control ES-cell clone after staining for Ki-67 or pHH3, respectively. The majority of cells stain positive for Ki-67 and are EGFP positive in the transgenic clone. pHH3 stained cells in M-phase, which display the brightest EGFP-fluorescence in EGFP-anillin clones.

FIG. 3: EGFP-anillin expression is specific to mitotic cells only
A: EGFP-anillin expression is decreasing over the course of ES-cell differentiation in EGFP-anillin clones, but stays constant in CAG-EGFP-controls. Note the increase in autofluorescence in the non transgenic controls starting at day 6. Insets show brightfield pictures of several EBs. B: plated EBs at day 6 (upper panel) and day 9 of differentiation (lower panel) stained for Ki-67, α-actinin and DNA (DAPI). The number of Ki-67 positive, mitotic cells decreased contiguous with EGFP-anillin expression. At differentiation day 9 proliferating cardiomyocytes could be detected with EGFP. Note the matching Ki-67 and EGFP-anillin expression.

FIG. 4: EGFP-anillin ES cell clones differentiate into all three germ layers
Day 12 differentiated and plated EBs from an EGFP-anillin clone. A: α-actinin positive cells as an example for mesoderm. B: Tubulin-3 as an example for neuroectodermal cells. C: Troma-1 (Keratin 8) positive cells as an example for endoderm. Proliferating cells were detected by staining for Ki-67. Nuclei stained with DAPI. Bar is 20 μm.

FIG. 5: EGFP-anillin indicates proliverative cells in EBs
A: Flow cytometry profile of day 4 differentiated and dissociated EBs from an EGFP-Anillin clone stained with either Ki-67 or pHH3. Not all EGFP-anillin expressing cells are Ki-67 positive and vice versa. All pHH3 positive cells also express EGFP-anillin. B: Percentage of Ki-67 positive and EGFP-anillin expressing cells in dissociated EBS at days 0 to 10 of differentiation. Ki-67 staining matches EGFP-anillin expression over the time course of differentiation.

Figure 6:
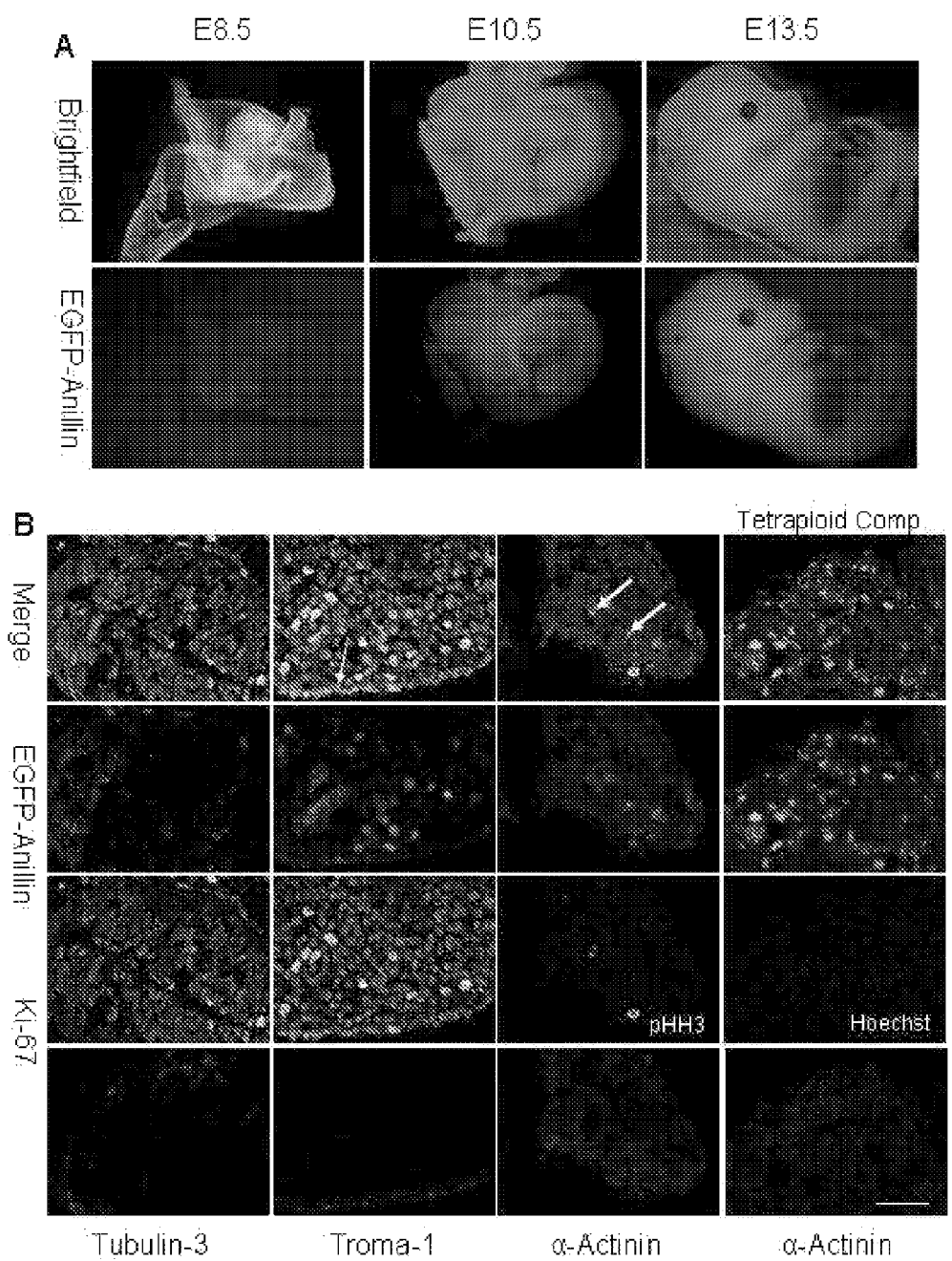
FIG. 6 shows that EGFP-anillin is an in-vivo mitotic marker during embryonic development.

FIG. 6: EGFP-anillin is an in-vivo mitotic marker during embryonic development A: Pictures of chimaeric embryos generated by diploid aggregation of morula-stage embryos with ES-cells at E8.5 and E10.5 and an embryo derived by tetraploid complementation at E13.5. All three embryos display EGFP-anillin expression due to a solid contribution of EGFP-anillin ES-cells. B: Sections of an E10.5 embryo revealed contribution of EGFP-anillin expressing ES-cells to all three germ layers. Tubulin-3, Troma-1, and α-actinin were used as representative markers for neuroectoderm, endoderm, and mesoderm, respectively. Mitotic markers Ki-67 and pHH3 were colocalized with EGFP-anillin. Localization was predominantly nuclear (thin arrow), cytoplasmatic and in midbodies (thick arrows). Cardiac section of an E13.5 embryo generated by tetraploid aggregation displayed more EGFP-Anilin positive cells due to the highest contribution of ES-cells to the embryo (fourth panel). Bar is 50 μm.

FIG. 7: An EGFP-anillin lentiviral system
A: The EGFP-anillin lentivirus and its elements. B: Transduction of E13.5 primary cardiomyocytes with EGFP-anillin lentivirus. Stably transducted and proliferating cardiomyocytes with EGFP-anillin in the midbody of two daughter cells (first panel) or nuclear in a Ki-67 positive cardiomyocyte (second panel). Bar is 50 μm.

FIG. 8: Cardiac-specific expression of EGFP-anillin
A: schematic drawing of the aMHC-EGFP-anillin vector. EGFP-anillin is under control of the cardiomyocyte specific myosin heavy chain 6 promoter. B: ES-cells stably transfected with MHC-EGFP-anillin were differentiated as EBs for 8 days, plated and stained for cardiac marker α-actinin. Cardiomyocytes with nuclear EGFP-anillin could be detected at a frequency consistent with proliferation rates at this day of differentiation. Bar is 40 μm.

FIG. 9: Candidate promoters for cell-cycle specific expression of EGFP-anillin
A: Candiate promoters for cell-cycle specific expression of EGFP-anillin include the E2F1 promoter, the Ki-67 promoter, the PCNA promoter, and the cyclin B1 promoter. These promoters are well described in the art, and detailed sequence information can, e.g., be obtained from the NCBI nucleotide sequence online database (National Centre for Biotechnology Information, Bethesda, Md., USA). B: Colony of a stably transfected ES-cell line expressing EGFP-anillin under control of the Cyclin B promoter. The left picture shows nuclei stained by Hoechst. The picture on the right displays EGFP-anillin predominantly located in the nucleus. The arrow points to a contractile ring.

FIG. 10: Nucleic acid sequence of SEQ ID NO: 1
SEQ ID NO: 1 shows the nucleic acid sequence encoding the EGFP-anillin fusion protein of the present invention under the control of the CAG promoter. The protein anillin is derived from mouse and has the NCBI accession No.: NP_082666. The cDNA sequence encoding mouse anillin has the NCBI accession No.: NM_028390.

Figure 11:
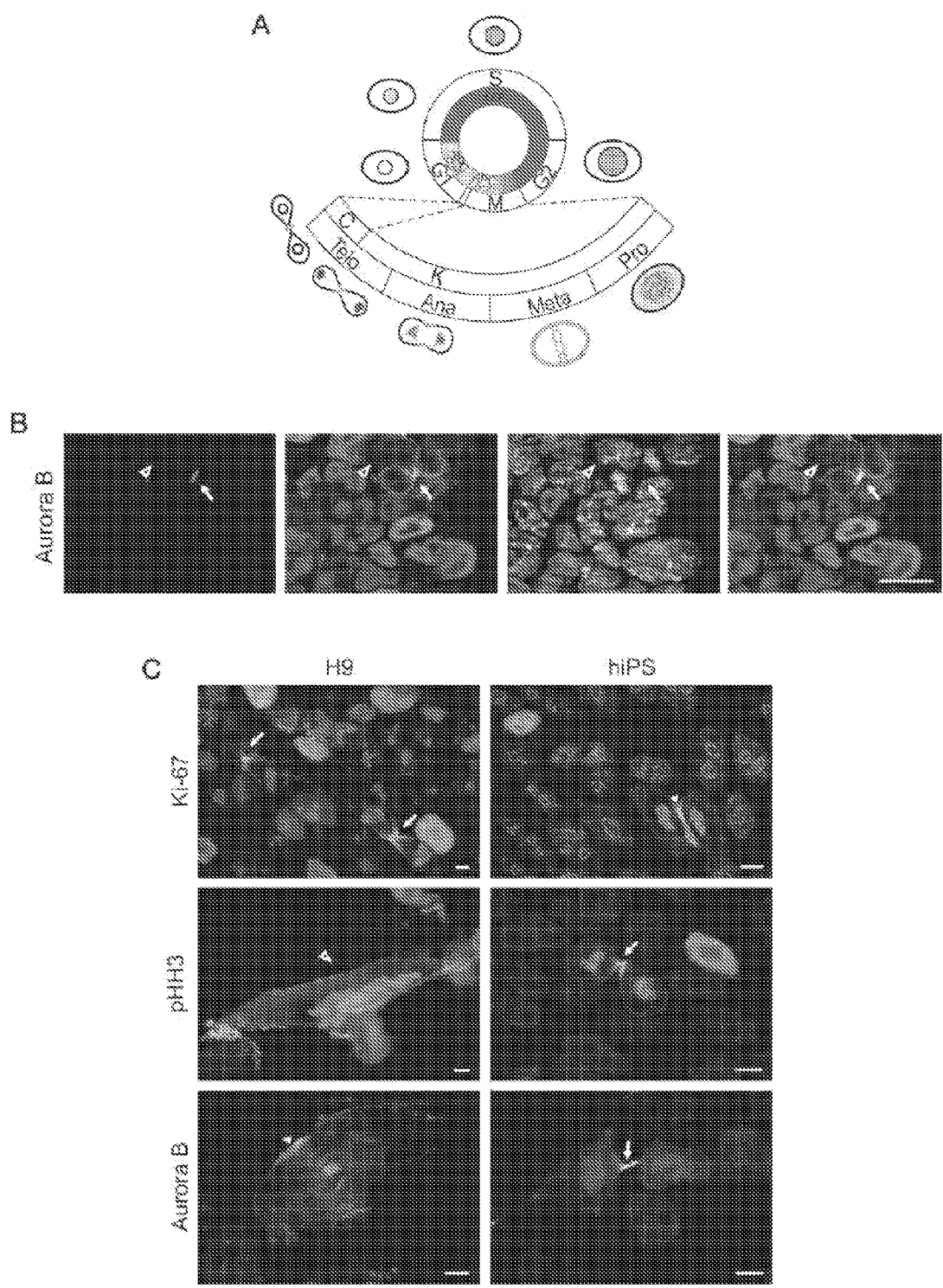
FIG. 11 shows that EGFP-anillin expression is a mitotic marker in murine and human pluripotent cells.
Figure 11:
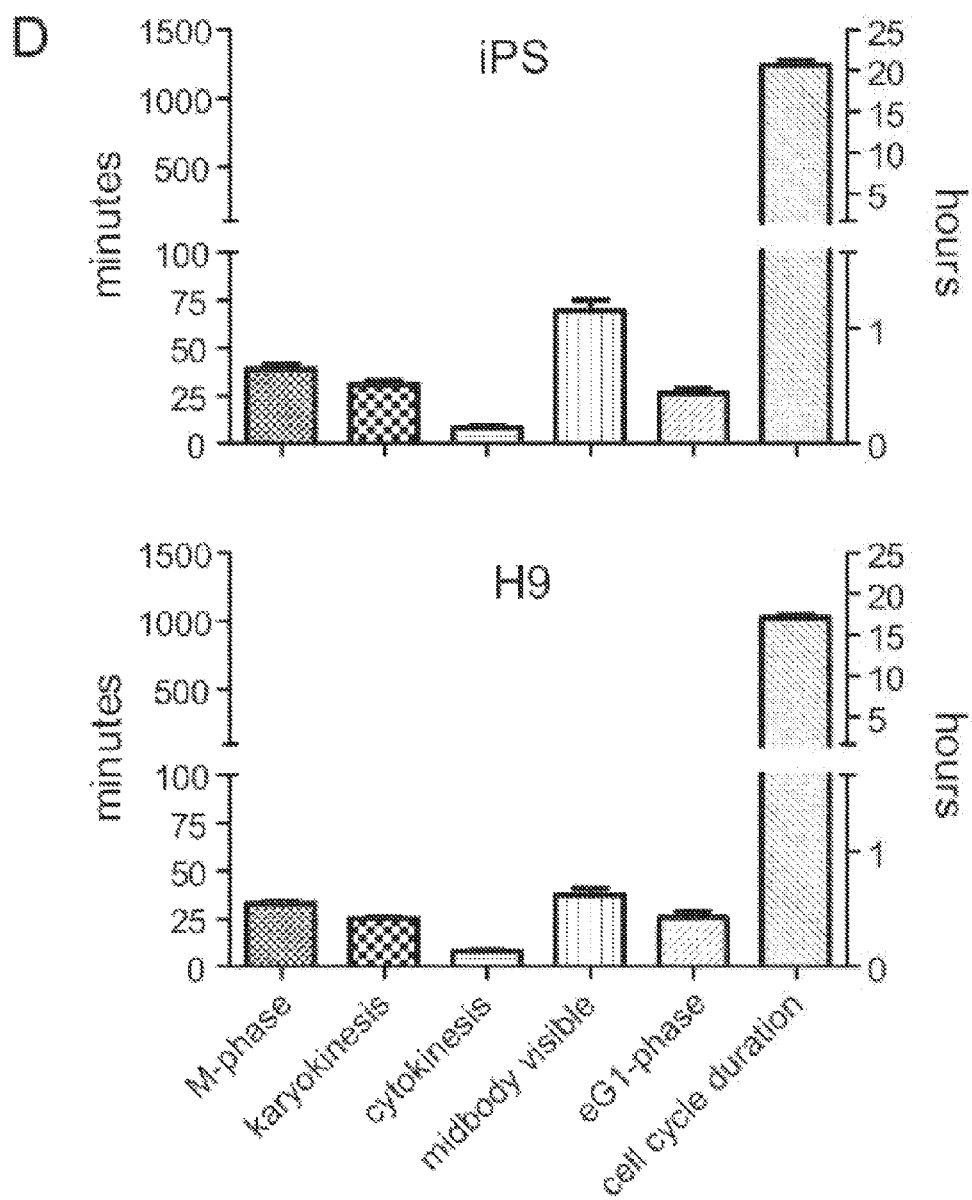

FIG. 11: EGFP-anillin expression is a mitotic marker in murine and human pluripotent cells
A: Scheme of the subcellular localization of the EGFP-anillin fusion protein during the cell cycle. K=karyokinesis, C=cytokinesis, APC=anaphase promoting complex, SCF=Skp, Cullin, F-box containing complex. B: Stainings for the proliferation marker Aurora B kinase revealed stringent co-localization with EGFP-anillin signal. Note localization in cytoplasm/cortex (open arrowheads), contractile rings (solid arrowheads), and midbodies (arrows); nuclei are stained with Hoechst dye. Bar=25 μm. C: Stainings of lentivirus CAG-EGFP-anillin transduced human iPS cells and ESCs for the proliferation markers Ki-67, pHH3 and Aurora B kinase. Note the overlap between all three cell cycle markers and the M-phase specific localization of EGFP-anillin in the nucleus, cytoplasm (open arrowhead), contractile ring (solid arrowhead), and midbodies (arrows); Ki67 stains nucleoli in human cells; nuclei are stained with Hoechst dye (blue). Bar=5 μm. D: Analysis of cell cycle kinetics of human iPS cells and ESCs by time lapse video microscopy. Note the significantly (t-test, p=0.00007) longer overall cell cycle duration in human iPS cells. Data are represented as mean±SEM. See also FIG. 14.

FIG. 12: EGFP-anillin is a mitotic marker in ESC-derived differentiating cells
A: Staining for Ki-67 (white) of plated EBs at day 16 of differentiation revealed a perfect overlap with EGFP-anillin expression. Some of the weak EGFP-anillin positive cells have a very faint, but visible Ki67 signal (arrowheads), whereas others are clearly negative for Ki-67 and EGFP-anillin (arrows); nuclei are stained with Hoechst nuclear dye. Bar=25 µm. B: EGFP-anillin marked proliferating cardiomyocytes because of its specific position in contractile rings and midbodies; the cells were identified as cardiomyocytes based on their typical shape and α-actinin positive staining. Note positive co-labelling with Ki-67 (white); nuclei are stained with Hoechst dye. Bars=10 µm. See also FIG. 14.

Figure 13:
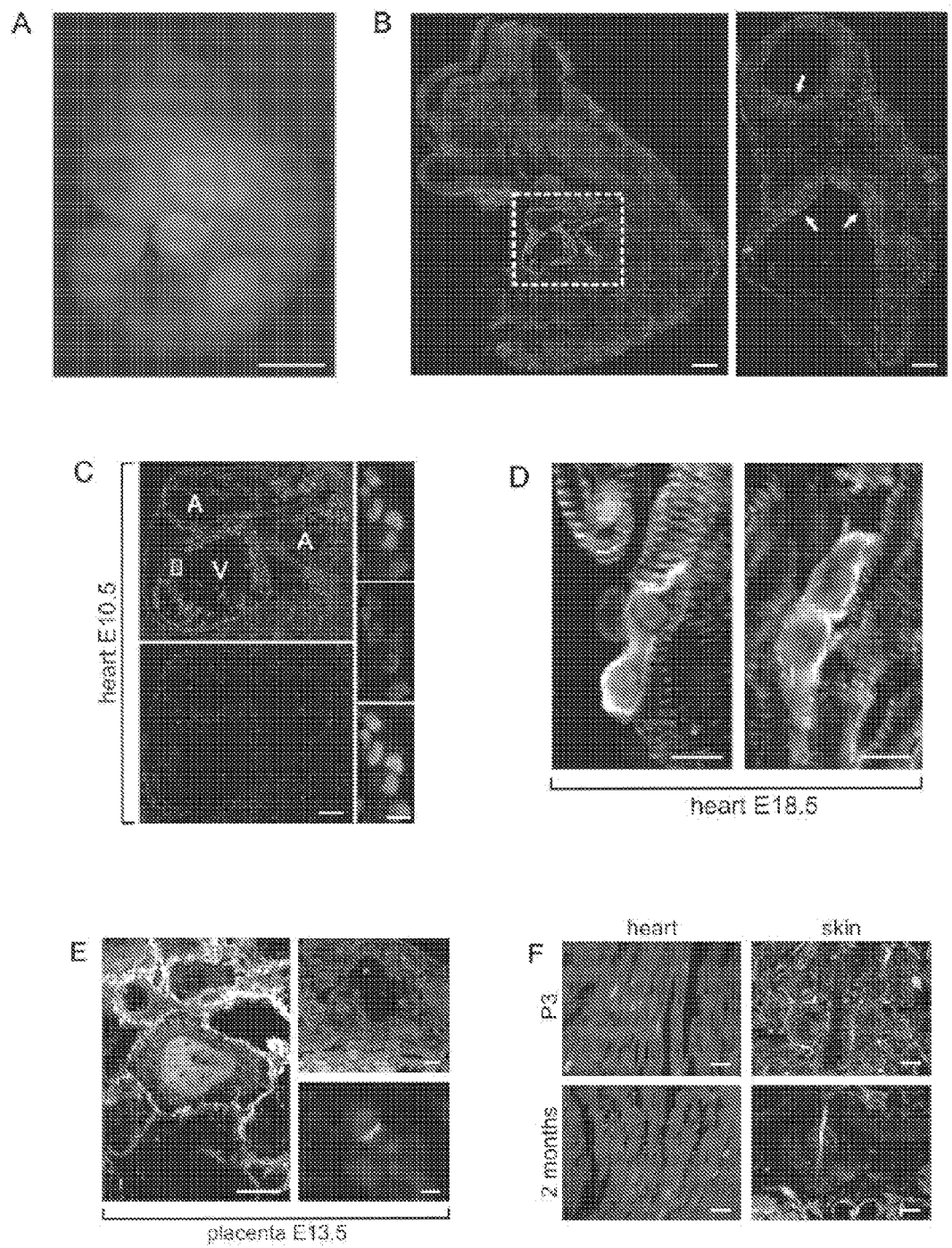
FIG. 13 shows that EGFP-anillin is a mitotic marker in vivo during embryonic development and in the adult heart post-injury.

FIG. 13: EGFP-anillin is a mitotic marker in vivo during embryonic development and in the adult heart post-injury A: Epifluorescence picture taken from an E10.5 EGFP-anillin transgenic embryo revealed strong EGFP expression (green) in the heart. Bar=1 mm. B: Sagittal sections of an E10.5 EGFP-anillin embryo revealed EGFP expression in all tissues, the strengest signal was visible in the heart; cardiomyocytes are identified by positive α-actinin staining (dashed Square; left panel); cross sections through the brain showed EGFP-anillin expression in neuroepithelium (right panel). Bar=200 µm. C: Sagittal sections through the heart of an E10.5 EGFP-anillin embryo evidenced that both, the atria (A) and the ventricle (V) were strongly EGFP-anillin positive. Ki67 staining of the same section proved a high overlap between both signals. Ventricular cardiomyocytes (right panel) display EGFP-anillin expression and stained positive for Ki-67; the right panel is a magnification of the area marked by the solid Square from the left panel; nuclei are stained with Hoechst dye in the merged image. Bars=100 µm (left panel), 10 µm (right panel). D: Proliferating α-actinin positive (white) cardiomyocytes in sections from an E18.5 EGFP-anillin heart can be clearly identified because of the EGFP-labelling (green) of contractile rings and/or midbodies; Ki67 positive nuclei are shown in red; nuclei are stained with Hoechst dye. Bar=5 µm. E: Giant trophoblast cells in placenta of EGFP-anillin mice displayed exclusively nuclear EGFP localization (left picture), whereas in the chorionic plate cells with nuclear localization (upper right picture) and typical M-phase localization (e.g. midbodies, lower right picture) were seen; nuclei are stained with Hoechst dye. Bar=25 µm. F: EGFP-anillin expression (was observed in cardiomyocytes and skin cells of P3 mice; in 2 months old mice no signal could be detected. Bar=25 µm. G: Sections through a heart of an adult EGFP-anillin transgenic mouse 4 days after cryoinfarction. EGFP-fluorescence revealed numerous proliferating cells in the scar tissue, the neighbouring intact myocardium can be identified based on its strong autofluorescence; nuclei are stained with Hoechst dye. Bars=100 µm (upper picture), 25 µm (lower picture). H: Positive staining for a-smooth muscle actin (white) identified EGFP-anillin expressing cells as myofibroblasts (arrows). High magnification of such cells revealed EGFP-anillin localization to the contractile ring and midbody (small arrows) proving cell division; nuclei are stained with Hoechst dye. Bar=5 µm. I: Some of the α-actinin positive (white) cardiomyocytes in the border zone of the lesion showed nuclear localization of EGFP-anillin (arrows in upper picture); none of these displayed a contractile ring or a midbody. Intact cardiomyocytes display yellow autofluorescence; nuclei are stained with Hoechst dye. Bars=25 µm, 5 µm (inset). See also FIG. 14.

Figure 14:
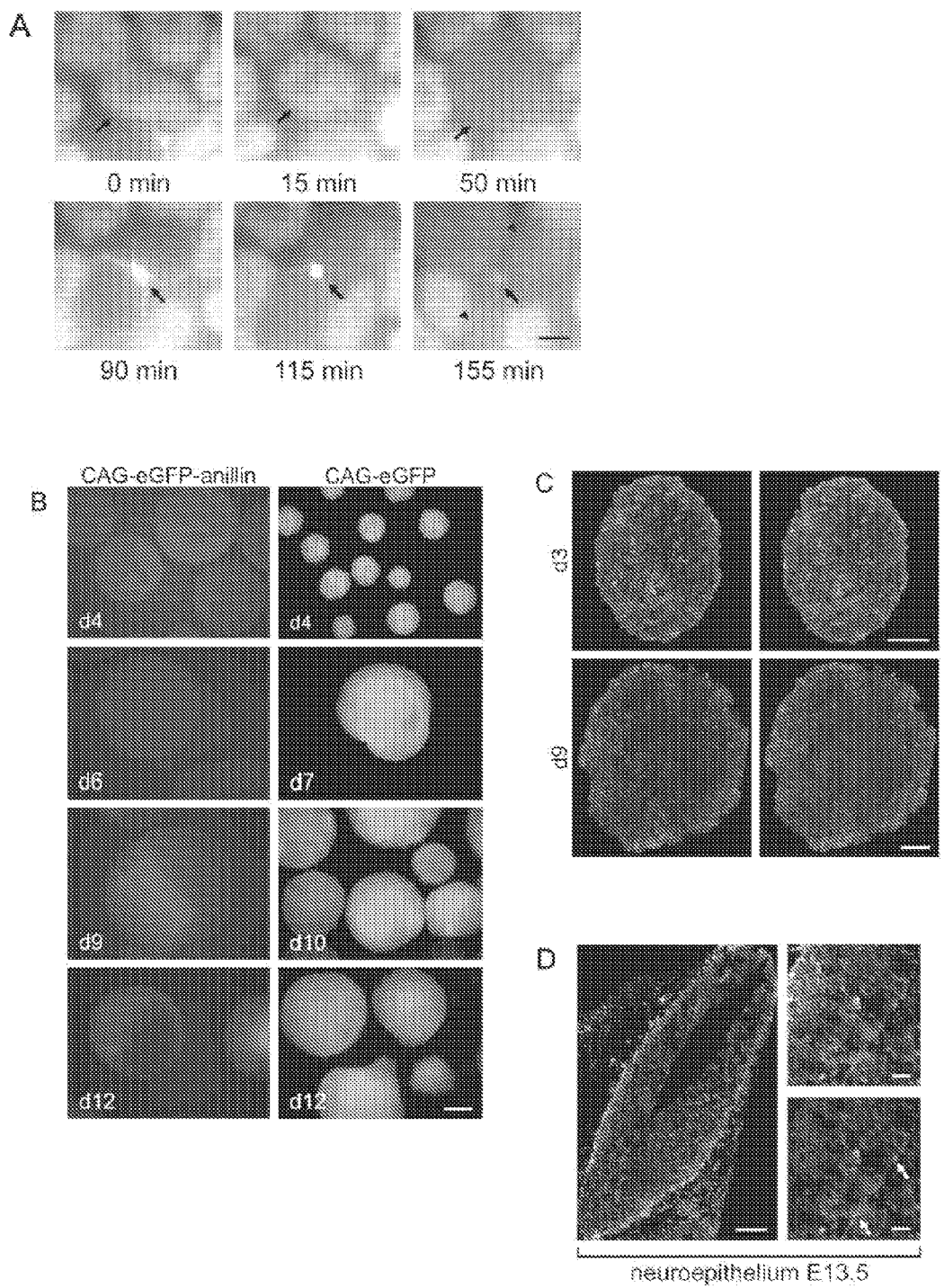
FIG. 14 shows that EGFP-anillin is a specific marker for cell division in-vitro and in-vivo.

FIG. 14: EGFP-anillin is a specific marker for cell division in-vitro and in-vivo A: Time-lapse images taken from a CAG-EGFP-anillin ESC clone. The arrows mark a cell with the changing localization of EGFP-anillin during the M-phase. The arrowheads point to the nuclei of the daughter cells. Bar=5 µm. B: Comparison of a CAG-EGFP-anillin ESC clone (left panel) with a CAG-EGFP clone (right panel) during differentiation. EGFP-anillin fluorescence declines during differentiation indicating a decline in the rate of proliferation, whereas EGFP fluorescence in CAG-EGFP cells remains strong. Bar=200 µm. C: Sections of EGFP-anillin EBs after 3 (upper panel) and 9 days (lower panel) of differentiation. On day 3, EGFP-anillin positive cells are found throughout the EB, at day 9 proliferation is restricted to the cortical areas of the EB; nuclei are stained with Hoechst dye. Bar=200 µm. D: Transversal sections of neuroepithelium of an E13.5 EGFP-anillin embryo stained for β-Tubulin 3 (white). The insets indicate the specific expression of EGFP-anillin in the less mature, β-Tubulin 3 negative cells. The arrows mark apical midbodies which are released into the extracellular space by neuroepithelial cells; nuclei are stained with Hoechst dye. Bars=100 µm, 25 µm (insets). E: Cross sections of an EGFP-anillin heart from mice at P3. The upper panel shows native EGFP-anillin fluorescence in cardiomyocytes labelled by α-actinin staining (white). Co-stainings for EGFP and Ki-67 (white) in a subsequent section (lower panel) revealed restriction of EGFP-signals exclusively to cardiomyocytes (arrows). The arrowheads mark Ki-67 positive/EGFP negative cells; nuclei are stained with Hoechst dye. Bar=25 µm. F: Sections of P3 hearts from transgenic mice revealed EGFP-anillin localization in contractile rings and midbodies (arrows). Bar=20 µm. G: Section of an adult EGFP-anillin transgenic mouse heart four days after cryoinfarction stained for Ki-67 and Hoechst nuclear dye after antigen retrieval. Proliferation was evident in the lesion (lower inset), but not in the intact myocardium (upper inset); intact myocardium displays yellow autofluorescence. Bars=100 µm, 25 µm (insets).

EXAMPLES

Material and Methods

Generation of the CAG-pEGFP-anillin$^{201-3801}$ fusion construct

Mouse Anillin-cDNA was isolated by RT-PCR of total RNA from murine, embryonic diaphragm (Primers: (1) Anillin 121 forward SEQ ID NO. 2: 5'GCCTGCACTCACT-TCTTTCC3', (2) Anillin 4062 reverse SEQ ID NO. 3: 5'GACTATGCAGGCCCAAATGT3'). A BglII-HpaI fragment was inserted in frame into the multiple cloning site (BglII, SmaI) of the pEGFP-C1 vector (CLONTECH Laboratories, Inc.). Sequencing resulted in the construct pEGFP-anillin$^{296-3801}$ (del (2962-3075). A BglII-EcoRV Anillin-fragment was inserted into the pDsRed2-C1 vector (CLONTECH Laboratories, Inc.) via BglII and SmaI. The CMV-promoter of the construct pDsRed2-Anillin$^{296-3801}$ was exchanged with the CAG-promoter from the pCIG2 plasmid (given by Carol Schuurmans, Calgary) (EcoRI, NotI, NdeI). To get rid of the deletion 2962-3075 in the EGFP-construct and to introduce the CAG-promoter, the fusion fragment EGFP-anillin (AfeI, Hind III) were ligated into the vector CAG-pDsRed2-Anillin$^{296-3801}$ (XhoI, HindIII). A linker-PCR (primers: (1) Anillin-BamH1 forward SEQ ID NO. 4:5'CCCACTTCAATTTTGTCAGAACAAC3') was used to isolate a 242 by Anillin DNA-sequence, starting 5' of the start-codon. For amplification the PCR product was subcloned into the pCR 2.1-TOPO vector (Invitrogen), cut with BamHI and AclI and ligated in frame into the truncated CAG-pEGFP-anillin$^{296-3801}$ vector (BglII, AclI) leading to the expression of full-length EGFP-anillin. The CAG-pEGFP-anillin$^{2013801}$ vector was linearized with AseI restrictase and 30 µg were transfected into D3 ES-cells and G4 ES-cells. Electroporation, G418 selection and propagation of clones was performed as reported previously (as described in Vintersten et al., Genesis, 40, 241-6, 2004).

ES (embryonic stem) cell culture, transfection and differentiation

For propagation and selection of transfected D3 ES cells, Dulbecco's modified Eagle's medium (DMEM) (Invitrogen), high-glucose, supplemented with fetal calf serum (FCS) (15% v/v) (Invitrogen), nonessential amino acids (0.1 mM), penicillin and streptomycin (50 µg/ml each), β-mercaptoethanol (0.1 mM), Leucemia inhibitory factor (LIF) (Chemicon) (500 U/ml) and G418 (300 µg/ml) was used. G4-ES cells were propagated in Knockout-DMEM (Invitrogen) supplemented with the same substances as described above, except for FCS, using 15% v/v FCS from Promega. Additionally L-Glutamine (2 mg/ml) was added and the concentration of G418 for selection was 166 µg/ml. The ES cells were kept on irradiated murine fibroblasts derived from neomycin resistant mice.

G4 hybrid ESCs (as described in George, S. H. et al., Proc. Natl. Acad. Sci. U.S.A 104, 4455-4460, 2007) were cultured in Knockout-Dulbecco's modified Eagle's medium (DMEM) (Invitrogen), high-glucose, supplemented with 15% v/v fetal calf serum (FCS) (Promega), 0.1 mM nonessential amino acids (Invitrogen), 2 mg/ml L-Glutamine (Invitrogen), 50 µg/ml each penicillin and streptomycin (Invitrogen), 0.1 mM f3-mercaptoethanol (Sigma), and 500 U/ml Leucemia inhibitory factor (LIF) (Chemicon). The ESCs were kept on irradiated murine fibroblasts derived from neomycin resistant mice. For generation of transgenic ESCs $5 \times 10^6$ cells were mixed with 30 µg of linearized plasmid DNA in PBS and electroporated at 250 V and 500 µF, 1 pulse, using a Bio-Rad Gene Pulser. The cells were plated on two 100-mm plates. Selection for neomycin resistant cells started two days after electroporation by adding 165 µg/ml G418 to the medium. Resistant colonies were picked onto mouse embryonic fibroblast-coated 24-well plates, propagated and analyzed for eGFP expression.

ES cell differentiation was performed by the Hanging prop protocol (as described in Wobus et al., Differentiation, 48, 173-82, 1991). In brief, $0.2 \times 10^6$ ES cells were suspended in 10 ml IMDM high glucose medium, supplemented with 20% FCS (Invitrogen) in the absence of LIF. 20 µl drops were incubated for 2 days at 37° C., 5% $CO_2$. The EBs were washed in bacterial dishes and cultivated with differentiation medium in suspension on a shaker. After 3 days EBs were plated separately on gelatine-coated glass coverslips in 24-well tissue plates or continuous cultivated in suspension. At all stages of differentiation, the EBs were monitored under a fluorescent microscope (Axiovert 200 M, Carl Zeiss MicroImaging, Inc.) using a FITC/TRITC filter set and ×5 or ×10 objectives.

Dissociation of EBs

For the quantification of proliferation, EBs were separated into single cells at different time points. EBs were washed and dissociated with 0.125% Trypsin/EDTA for 5 minutes. The treatment was stopped with differentiation medium containing FCS and the cells were centrifuged (210×g, 5 minutes). ~$0.1 \times 10^6$ cells were plated on coverslips pretreated with 0.1% gelatine in 24-well tissue plates. After 48 hours, the cells were fixed with 4% paraformaldehyd (PFA) at room-temperature for 30 minutes.

Life-Cell-Imaging of Undifferentiated Murine ES Cells

ES cells were sown on fibroblast-coated glass coverslips and cultivated with ES-cell medium. Life-cell-imaging was performed in a chamber with 37° C., 5% $CO_2$ under a fluorescent microscope (Axiovert 200M, Carl Zeiss MicroImaging, Inc.) using the Colibri system (blue LED, white LED), a GFP-filter and a ×40 oil-objective. Pictures and movies were generated with the Axiovision software (Zeiss). Cells were monitored for 48 hours and pictures taken every 5 min; measurements of cell cycle durations were done on the time lapse sequences. Karyokinesis was determined as the time interval between nuclear membrane dissolution and appearance of the contractile ring; duration of cytokinesis was determined as the time period in which a contractile ring was visible; M-phase duration was calculated by adding the durations of karyokinesis and cytokinesis; early G1-phase was defined as the time interval from the end of cytokinesis to the first reappearance of EGFP-anillin fluorescence in the nucleus; cell cycle duration was determined by monitoring dissolving of the nuclear membrane in the mother and daughter cells, respectively.

Life-Cell-Imaging of Undifferentiated Human iPS and ES Cells

Human ESCs were seeded on matrigel-coated glass coverslips and cultivated with conditioned medium. Life-cell-imaging was performed in a chamber with 37° C., 5% $CO_2$ under a fluorescent microscope (Axio Observer Z.1, Carl Zeiss MicroImaging, Inc.) using the Exfo x-cite 120q fluorescence light source, a GFP-filter and a x20 air-objective. Pictures and movies were documented with a Hamamatsu OrcaER C4742-80-12AG camera and generated with the Volocity 5.2.1 software (Perkin Elmer). Duration of the overall cell cycle and of the different subphases were determined as for murine ESCs. Life cell imaging of human iPS cells was performed as with murine ESCs.

Fixation, Histology and Immunofluorescent Stainings

Cryopreserved teratoma, embryos or adult tissues were sectioned (10 µm). Fixated cells and tissue slices were stained for the following differentiation markers (in 0.25% Triton X in PBS, supplemented with 5% donkey serum; 2 hours at room temperature): Oct 3/4 (1:100, Santa Cruz), α-actinin (1:400, Sigma-Aldrich), Troma-1 (1:50, Rolf Kemler, Freiburg), TuJ1 (1:1000, Covance). As proliferation markers pHH3 (1:100, Upstate Biotech), NCL-Ki67p (1:1000, Novocastra) and Ki67 (1:400, kindly provided by J. Gerdes, Kiel) were used. Primary antibodies were visualized by secondary antibodies conjugated to Cy3 and Cy5 (1:400, Jackson ImmunoResearch) diluted in Hoechst 33342 (nuclei staining) at RT for 1 hour. Pictures were taken with an inverted fluorescence microscope (Axiovert 200; Carl Zeiss MicroImaging, Inc.) equipped with a slider module (ApoTome; Carl Zeiss MicroImaging, Inc.).

Prior to immunofluorescence staining all, cells were fixed with 4% formaldehyde solution (FA) in PBS. Transgenic mouse hearts were perfused with 4% FA in PBS for 10 min at room temperature. All other organs were immersion fixed with 4% FA in PBS over night at 4° C. Cryopreserved embryos or adult tissues were sectioned with a cryotome into 10 µm thick slices. Fixated cells and tissue slices were stained for the following differentiation markers (in 0.2% Triton X in PBS, supplemented with 5% donkey serum; 2 hours at room temperature): α-actinin (1:400, Sigma-Aldrich), Troma-1 (1:50, R. Kemler, Freiburg), TuJ1 (1:1000, Covance). As proliferation markers pHH3 (1:100, Upstate Biotech), Ki67 (1:400, kindly provided by J. Gerdes, Kiel), Ki-67 TEC3 (1:200, Covance) and Aurora B (1:400, Abcam). Primary antibodies were visualized by secondary antibodies conjugated to Cy3 and Cy5 (1:400, Jackson ImmunoResearch) diluted in Hoechst 33342 (nuclei staining) at room temperature for 1 hour. Pictures were taken with an inverted fluorescence microscope (Axiovert 200; Carl Zeiss MicroImaging, Inc.) equipped with a slider module (ApoTome; Carl Zeiss MicroImaging, Inc.).

Flow Cytometry

For flow cytometry analysis undifferentiated ES cells were cultivated on gelatine-coated tissue culture dishes with ES cell medium for at least 3 passages to dispose fibroblasts, washed with phosphate-buffered saline (PBS) and then dissociated to a single-cell suspension by trypsin treatment for 2-3 minutes. The reaction was stopped with ES cell medium. After centrifugation (1000 rpm) for 5 minutes, the cells were washed in PBS and fixated (2% PFA at room-temperature for 30 minutes or in 70% ethanol at −20° C.). Differentiated EBs (day 2-day 10 of differentiation) were dissociated as described above and fixated with PFA or 70% ethanol. For all flow cytometric measurements a Canto cytometer (Becton-Dickinson) was used. Analysis was performed using the FACSDiva (Becton-Dickinson) and the FlowJo Software. Nontransfected G4 ES cells were used for negative controls, G4 CAG-EGFP transgenic ES cells for positive controls.

Embryo Aggregation and Tetraploid Complementation Experiments

Aggregation experiments with diploid embryos were performed with morula stage CD1 embryos and clumps of G4 ES cells (as described in Nagy et al., Proc. Natl. Acad. Sci. USA 90 (18), 9424-9428, 1993). Tetraploid complementation experiments were performed by using G4 ES cell clones and tetraploid CD1 embryos generated by electrofusion as described by Nagy et al., Proc. Natl. Acad. Sci. USA, 104: 4455-60. 2007.

Generation of Transgenic Mice

Transgenic mice were generated by aggregation of transgenic G4 ESCs from two individual EGFP-anillin clones with tetraploid CD-1 embryos as described previously (as described in Nagy et al., Proc. Natl. Acad. Sci. USA 90 (18), 9424-9428, 1993). Transgenic mice generated by this method were bred to CD-1 mice for testing germline transmission. Offspring with agouti coat colour was analysed for inheritance of the transgene by PCR. The two transgenic EGFP-anillin mouse lines did not display any obvious differences with respect to transgene expression pattern.

Cryoinfarction 8-12 weeks-old CAG-EGFP-anillin mice were anesthetized and transmural cryolesions at the anterolateral left ventricular wall were generated using liquid-nitrogen-cooled copper probes 3 mm in diameter as described previously (as described in Roell, W. et al., Transplantation 73, 462-465, 2002). All animal experiments were approved by the local authorities.

Establishment of a CAG-EGFP-Anillin Lentivirus

The pSico vector (as described in Ventura et al., Proc. Natl. Acad. Sci. USA, 101, 10380-5, 2004) was truncated via excision of an XbaI-XhoI fragment in exchange with a CAG-EGFP-anillin$^{201-3801}$ fragment (AseI, HpaI) in a blunt-ended ligation. Lentiviral particles were prepared as described previously (as described in Pfeifer et al., Proc. Natl. Acad. Sci. USA, 46, 1540-52002). The functionality of the lentivirus was tested by transduction of active murine fibroblasts and primary embryonic cardiomyocytes prepared from CD1 embryos at the embryonic stage E13.5 by collagenase-dissociation. The cells were incubated with the virus in DMEM supplemented with FCS (15% v/v), nonessential amino acids (0.1 mM), penicillin and streptomycin (50 µg/ml each) and β-mercaptoethanol (0.1 mM). After 24 hours the medium was exchanged and 24, hours later the cells were fixated for immunohistochemistry.

Generation of CAG-Anillin-EGFP Transgenic Human iPS Cells and ESCs

Human iPS cells were generated by retroviral transduction of human cord blood derived unrestricted somatic stem cells with OCT4 SOX2, KLF4 and cMYC and further cultivation as described (as described in Kim, J. B. et al., Nature 461, 649-3, 2009 and in Zaehres, H. et al., Experimental Hematology in press, 2010). The human iPS cells and H9 human ESCs (as described in Thomson, J. A. et al., Science 282, 1145-1147, 1998) were transduced with CAG-EGFP-anillin lentivirus on matrigel in conditioned media by single round infections for 24 hours. Work with human ES cells (H9/WA09) was approved by RKI (Robert-Koch-Institut) license 37 from Jan. 20, 2009 and performed at the MPI Münster.

Quantification and Statistical Analysis

In cryosections of infarcted CAG-EGFP-anillin hearts the intact area of myocardium discriminated against the infarcted area by autofluorescence using a FITC/TRITC filter. The borderzone was determined as the area including all cells within a distance of 200 µm from the infarction. Using a wheat germ agglutinin staining to visualize cell membranes a quantification of cardiomyocytes/mm$^2$ was performed in a representative slice resulting in 1764 cardiomyocytes/mm$^2$. This number was used to estimate the number of cardiomyocytes in the borderzone of non-stained slices (one slice per mouse, n=5 mice). The number of EGFP-anillin positive cardiomyocytes in the borderzone was put in relation to the estimated number of cardiomyocytes.

The percentual distribution of EGFP-anillin localization in CAG-EGFP-anillin ESC colonies was determined by counting at least 200 cells from three different colonies. Quantitation of EGFP-anillin positive, Ki67 positive, pHH3 positive, and double positive cells from undifferentiated ESCs was performed on cells from three different CAG-EGFP-anillin clones (n=3). For the quantitation of differentiated cells from CAG-EGFP-anillin ESC clones three different differentiation experiments (n=3) were performed and counted for day 12 and one (n=1) for day 16 of differentiation. A minimum of 500 cells was counted per experiment. The quantitation of EGFP-anillin positive and Ki67 positive cell populations by flow cytometry was performed by analysis of two individual differentiation experiments (n=2) using FlowJo software. Gates were set according to isotype controls for Ki-67 stainings and autofluorescence of non transgenic G4 ESC for EGFP-anillin fluorescence.

Example 1

Cell Cycle Phase Specific Localization of EGFP-Anillin in ES-Cells

Anillin is a scaffolding protein and component of the contractile ring during M-phase of mitosis. During the cell cycle it is located in the nucleus during G1, S, and G2-phase, in the cytoplasm and cell cortex in early M-Phase, in the contractile ring during cytokinesis and eventually in the midbody. At the end of mitosis Anillin gets ubiquitinated by the anaphase promoting complex APC associated to Cdh1 and degraded by the proteasome. These properties render Anillin a perfect candidate for an in-vivo cell cycle marker. By cloning, the full length mouse Anillin cDNA was fused to the fluorescence marker EGFP. The expression of the fusion protein is driven by the ubiquitous chicken β-actin promoter with a CMV enhancer element (CAG promoter, FIG. 1A).

To proof the feasibility of the EGFP-anillin fusion protein as a cell cycle marker a stably transfected ES-cell line was generated. In vivo imaging of EGFP fluorescence in an EGFP-anillin ES-cell colony demonstrated nuclear and cortical as well as localization in the contractile ring and midbody of cycling cells (FIG. 1B). After fixation and nuclear staining with Hoechst EGFP was detected in nuclei, cytoplasm, cell cortex/contractile ring, and midbodies of G4 ES-cells (FIG. 1C). The time-dependent cell phase specific localization of EGFP-anillin was especially obvious by life cell imaging (FIG. 1D). By monitoring individual cells the duration of the complete cell cycle as well as several events during M-phase could be determined with great accuracy (Table 1).

Example 2

EGFP-Anillin Expression Specifically Correlates to Proliferating Cells

The specificity of EGFP-anillin as a proliferation marker was tested by immunofluorescence stainings with the mitotic markers Ki-67 and pHH3. Due to their highly proliferative nature Ki-67 stained nuclei of all ES cells but not irradiated fibroblasts (FIG. 2A). EGFP expression could also be observed in all ES cells but differentially located. Most cells displayed nuclear localization while in approximately 10% of the cells EGFP-anillin was detected in the cytoplasma, cortex, contractile ring or midbody. This is in accordance with the length of the phases of the mitotic cell cycle in which M-phase is the shortest of the four phases. The mitotic marker pHH3 stains proliferating cells from early prophase through metaphase, anaphase and telophase. Therefore the fraction of stained cells was significant lower than with Ki-67. EGFP-anillin was co-expressed in all pHH3 positive cells and localized predominantly in the cytoplasm, cell cortex or contractile ring as expected from the localisation of endogenous Anillin protein in M-phase (FIG. 2A). Flow cytometric analysis confirmed the results from immunofluorescence staining (FIG. 2B). Untransfected controls displayed a cell population of 90-95% positive for Ki-67 and 14-20% positive for pHH3. In ES-cell clones stably transfected with EGFP-anillin cell populations positive for Ki-67 and pHH3 were also expressing EGFP-anillin, thereby corroborating the role of Anillin as a mitotic marker (FIG. 2B). Almost all pHH3 positive cells displayed the highest expression levels of EGFP-anillin due to its accumulation during the earlier cell cycle phases. However 3-5% of the EGFP positive cells did not co-stain with Ki-67. This is most likely due to the late onset of Ki-67 expression in G1 phase.

Example 3

Differentiation of EGFP-Anillin Clones

To address the feasibility of the EGFP-anillin system as a proliferation marker in cell populations consisting of proliferating and postmitotic cells, the EGFP-anillin ES-cell clones were differentiated to embryoid bodies (EBs) by using the hanging drop protocol. As a control an ES-cell clone stably transfected with the ubiquitous CAG promoter driving the expression of EGFP was used. The intensity of EGFP fluorescence decreased over the time course of differentiation in EGFP-anillin clones while in CAG-EGFP control clones fluorescence intensity remained unchanged for the first 6 days (FIG. 3A). Starting at day 8 of differentiation EGFP expression was also reduced in the CAG-EGFP control clone (FIG. 3A lower panel). This effect is caused by the changes in expression levels of the CAG-promoter in different cell types. The same phenomenon was observed in the EGFP-anillin clones, combined with a loss of expression in non-dividing/postmitotic cells (FIG. 3A upper panel). At day 10 of differentiation EGFP fluorescence was only evident in well defined regions of EGFP-anillin EBs, thereby indicating regions of high mitotic activity. To further analyze the specificity of EGFP-anillin in differentiating cells, EBs were plated at day 5 of differentiation on coverslips and stained for mitotic activity with Ki-67 antibody one day later (FIG. 3B upper panel). There was a solid overlap of EGFP-anillin fluorescence with Ki-67 staining. Surprisingly, EGFP-anillin did not accumulate in non cycling, Ki-67 negative cells, suggesting a constitutive active $APC^{Cdh1}$ in post-mitotic differentiated cells in EBs. To be able to quantify mitotic staining, EBs were dissociated and the resulting single cell suspension was plated on coverslips (FIG. 3B two lower panels). At day 12 of differentiation quantification revealed that approximately half of the total cells (50.1%) were still proliferating as measured by Ki-67 staining. Also half of all investigated cells (47.4%) were expressing EGFP-anillin which suggested a good match between Ki-67 and the transgene (89.1%). However, at this time point 10.9% of all Ki-67 positive cells did not express EGFP-anillin, while 5.2% of the EGFP-anillin positive cells did not stain for Ki-67. This is a population of 2.6% false positive and 5.5% false negative cells referring to the total population. Immunofluorescence staining revealed that EGFP-anillin ES-cell clones were able to differentiate into all three germ layers. Proliferating, Ki-67 positive and EGFP-anillin expressing cells could be detected costaining with α-actinin as an example for mesoderm (FIGS. 3B and 4A), Tubulin-3 for neuroectodermal cells (FIG. 4B) and Troma-1 for endodermal cells (FIG. 4C). EGFP-anillin was predominantly located in the nucleus but all the other expected localizations could also be detected (FIG. 3B lower panel).

Quantification of EGFP-anillin and mitotic markers Ki-67 and pHH3 during proliferation was also performed by flow cytometry. Differentiated EBs were dissociated, stained for proliferation markers Ki-67 and pHH3 and analysed in a flow cytometer. There was a good overall correlation between GFP-positive and Ki-67 positive cell percentage of the total population (FIG. 5A). Proliferation rate significantly dropped at day 6 of differentiation and slightly decreased onwards. As early as day 4 of differentiation, a cell population of EGFP-anillin positive but Ki-67 negative cells and a population positive for Ki-67 and negative for EGFP-anillin was found (FIG. 5B). This result correlated to the quantification on dissociated and plated EBs. Staining for the M-phase specific marker pHH3 revealed that all pHH3 positive cells also expressed EGFP-anillin (FIG. 5B), demonstrating the high accuracy of the EGFP-anillin system for indicating cycling cells in M-phase.

Example 4

Aggregation Chimaeras of EGFP-Anillin Clones

To elucidate the feasibility of EGFP-anillin as a proliferation marker in vivo, embryonic chimaeras were generated by aggregation of EGFP-anillin G4 ES-cells with either morula stage CD1 embryos or tetraploid wildtype 4 cell-stage embryos. Dissection at E8.5 revealed EGFP expression in all tissues of the developing embryo (FIG. 6A). The same was true for embryos at E10.5 in which the mosaic nature of the chimaeric embryos with patches of non expressing wildtype cells was evident (FIG. 6A). Sectioning and immunofluorescence staining of E10.5 chimaeric embryos demonstrated the contribution of EGFP-anillin transgenic ES-cells to all germ layers. Tubulin-3 was used as a marker for neuroectoderm, Troma-1 for endodermal cells and α-actinin for mesodermal cardiac muscle cells. EGFP-anillin expressing cells were found in the neural tube (FIG. 6B first panel), in the primitive endoderm (FIG. 6B second panel, arrow), and the heart (FIG. 6B third panel). EGFP expression was predominantly nuclear localized, but could also be observed in the midbody/contractile ring or cytoplasmatic (FIG. 6B, arrows). Staining for proliferation markers Ki-67 and pHH3 revealed a colocalization with EGFP in all cells analyzed (FIG. 6B). However due to the chimaerism there were more cells staining positive for the proliferation markers than expressing EGFP-anillin. Unfortunately the experimental design of diploid aggregation did not allow a quantification of the contribution of EGFP-anillin ES-cells. In contrast, the tetraploid complementation technique allows the generation of completely ES-cell derived embryos (as described in Nagy et al., Proc. Natl. Acad. Sci. USA 90 (18), 9424-9428, 1993). In accordance to this, cardiac sections of embryos derived by tetraploid complementation displayed more EGFP-anillin expressing cells than sections from chimaeric embryos (FIG. 6B fourth panel).

Example 5

Lentiviral Transduction of Primary Cardiomyocytes

A powerful tool for delivery of a transgene to cells and tissues in vivo is the lentiviral system. By transduction of CAG-EGFP-anillin into the border zone of a myocardial infarction or a skin wound it would be possible to track proliferating cells and to analyze regenerative patterns of wound healing. Advantage was taken of such a system by cloning CAG-EGFP-anillin cassette into pSico, a well established $2^{nd}$ generation lentiviral vector (as described in Ventura et al., Proc. Natl. Acad. Sci. USA, 101, 10380-5, 2004). To test the resulting EGFP-anillin-lentivirus (FIG. 7A), primary cardiomyocytes derived from an E13.5 mouse embryo were tranduced, which were still proliferative. Approximately 10% of all analyzed cardiomyocytes, which were identified by α-actinin staining, expressed EGFP-anillin (FIG. 7B). All of these cells stained positively for Ki-67 and therefore no false positive cells could be detected. The percentage of false negative cells was impossible to determine due to the unknown transduction efficiency. However, nuclear localization as well as localization in the contractile ring/midbody was apparent in transduced cardiomyocytes, thereby verifying the feasibility of the EGFP-anillin lentiviral system.

Example 6

Generation of an ES-Cell Line with Cardiac Specific EGFP-Anillin Expression

There is an ongoing controversy if adult, postmitotic cardiomyocytes are still able to proliferate under certain circumstances or not. A transgenic in-vivo system to proof either hypothesis would be a cardiomyocyte specific expression of the EGFP-anillin in a transgenic mouse. A vector consisting of the cardiomyocyte specific aMHC promoter driving the expression of the EGFP-anillin fusion protein was cloned (FIG. 8A). After electroporation in G4 ES-cells and generation of stable transfected lines, several clones to embryoid bodies were differentiated. At day 8 of differentiation at which beating areas could be observed the EBs were fixed, cryosectioned and stained for cardiomyocytes with α-actinin antibody (FIG. 8B). In areas staining positive for α-actinin several EGFP-expres sing cells could be detected. The localization was predominantly nuclear. The frequency of EGFP-anillin positive cells was 1-2% which matched the Ki-67 frequencies of day 9 differentiated EBs. The generation of a transgenic mouse with this ES-cell line enables the analysis of the proliferation of cardiomyocytes during embryonic development, postnatal growth as well as physiological and pathological situations such as pregnancy, myocardial infarction and cardiomyopathy.

Example 7

Expression of EGFP-Anillin Under Control of Cell-Cycle Specific Promoters

A drawback of the CAG-EGFP-anillin system could be the accumulation of the fusion protein in postmitotic cells. Although not observed in differentiating ES-cells or chimaeric embryos to be the case, it might be possible to take place in some tissues of transgenic mice. This would inevitably lead to an overestimation of proliferating cells due to false positives. To circumvent such a source of false positive cells, vectors with cell cycle specific promoters such as E2F1 Ki-67 PCNA, and Cyclin B1 were cloned (FIG. 9A), driving the expression of EGFP-anillin. Those vectors are tested in the ES-cell system and will reveal the feasibility of this approach. So far, an ES cell clone stably expressing EGFP-anillin under transcriptional control of the Cyclin B1 promoter was generated. While the expression was weak compared to the CAG-EGFP-anillin clone, the typical subcellular localization could be observed (FIG. 9B).

Example 8

EGFP-Anillin Expression Marks Proliferating Cells and is Localized in a Cell Cycle Specific Fashion in ESCs The scaffolding protein anillin is a component of the contractile ring and appeared a perfect candidate for an in vivo proliferation marker because of its M-phase specific localization and complete degradation at the end of mitosis (as described by D' Avino, P. P., J. Cell Sci. 122, 1071-1079, 2009). Anillin is located in the nucleus during late G1, S, and G2-phase of the cell cycle, in the cytoplasm and cell cortex in early M-phase, in the contractile ring during cytokinesis and eventually in the midbody (FIG. 11A). At the end of mitosis and early G1-phase, anillin is ubiquitinated by the anaphase promoting complex (APC) associated to Cdh1 and degraded by the proteasome (as described in Zhao and Fang, Journal of Biological Chemistry Vol. 280, 33516-33524, 2005). In order to visualize anillin localization, the full length murine anillin protein was fused to the C-terminus of the fluorescence marker EGFP. Expression of the fusion protein is under control of the chicken β-actin promoter with a CMV enhancer element (CAG promoter). This promoter element has been reported to be ubiquitously active in muscle tissue (as described in Okabe, M. et al., FEBS Lett. 407, 313-319, 1997). To prove the functionality of the EGFP-anillin fusion protein as a cell cycle marker in stem cells, stably transfected G4 embryonic stem cell (ESC) lines were generated. Live cell imaging of EGFP fluorescence in an EGFP-anillin ESC colony demonstrated nuclear localization in the majority of cells (94.2%), but also cytoplasmatic/cortical (3.6%), contractile ring (0.9%) and midbody (1.3%) localization as expected from anillin localization in proliferating cells. These data were confirmed by a more detailed analysis after fixation and nuclear staining with Hoechst dye. In addition, the specificity of EGFP-anillin as a general proliferation marker was tested by immunofluorescence co-staining with Ki-67, a mitotic marker for all cell cycle phases. Quantitation revealed that 98.3% of all ESCs stained Ki-67 positive and 97.5% displayed EGFP-anillin fluorescence due to their highly proliferative nature. The overlap of Ki-67 staining with EGFP-anillin expression was 96% using microscopic analysis and 99% assessed by flow cytometry (Table 2). pHH3, a mitotic marker staining proliferating cells in M-phase, was also stained for. The fraction of pHH3 stained cells was, as expected, significantly lower (24.1% and 22.2% as determined by microscopy and flow cytometry, repectively) than with Ki-67, but importantly all pHH3 positive cells were also EGFP-anillin positive. In pHH3 positive cells EGFP-anillin localized predominantly to the cytoplasm, cell cortex or contractile ring as expected from the localization of endogenous anillin protein in M-phase. Staining for Aurora B kinase proved EGFP-anillin localization to the midbody after cytokinesis (FIG. 11B). To demonstrate the utility of EGFP-anillin as an excellent in vitro proliferation marker, time lapse microscopy was performed. The obtained videos revealed continuous EGFP-anillin expression in all proliferating cells, and the expected M-phase distribution of the fusion protein in the cytoplasm after nucleus dissolution followed by localizaton in the contractile ring and in the midbody. In summary, the EGFP-anillin construct is a highly sensitive marker of cell cycle activity and cell division.

Example 9

EGFP-Anillin as a Tool for Measuring Cell Cycle Kinetics in Human ESC and Induced Pluripotent Stem (iPS) Cell Lines An investigation was undertaken whether murine EGFP-anillin also worked in pluripotent human ESCs and iPS cells as proliferation marker. Such a system could provide new insights into differentiation processes and a screening system for the identification of molecules with proliferative or anti-proliferative actions. Human ESCs (H9) and iPS cells with an CAG-EGFP-anillin lentivirus were transduced and compared their cell cycle kinetics. Approximately 15% of all hESCs and hiPS cells were transduced, expressed EGFP-anillin and displayed a complete overlap with Ki-67 staining (FIG. 1C). Nuclear and cytoplasmic localization of EGFP-anillin as well as localization in the contractile ring or midbody was apparent in transduced human ESCs (FIG. 1C, arrows) corroborating the feasibility of the EGFP-anillin lentiviral system. The M-phase marker pHH3 stained condensed chromosomes in cells with cytoplasmatic or cortical EGFP-anillin localization while Aurora B kinase staining and EGFP-anillin co-localized in midbodies (FIG. 1C), indicating cell division.

The time-dependent cell phase specific localization of EGFP-anillin could be determined by life cell imaging (FIG. 14A). Monitoring of individual cells and their daughter cells enabled precise measurements of the duration of individual phases and of the complete cell cycle at single cell level (FIG. 1D). Cell cycle duration of H9 human ESCs was 17.0±0.5 hours whereas that of human iPS cells was significantly longer with 20.6±0.6 hours (p<0.0001). Also the duration of M-phase (p=0.0377), and karyokinesis (P=0.0174) were significantly longer in human iPS cells, while cytokinesis (p=0.9545) and early G1-phase (p=0.9268) did not differ significantly. The presence of the midbody after cytokinesis lasted significantly (p<0.0001) longer in human iPS cells (69.5±5.8 min) compared to human ESCs (37.5±3.6 min). In summary, the murine anillin gene works also as a bona fide cell cycle marker in human pluripotent cells and enabled us to measure the cell cycle kinetics of human iPS cells and ESCs.

Example 10

EGFP-Anillin is a Proliferation Marker in Differentiating Cells

To assess the specificity of the EGFP-anillin system for the identification of proliferating progenitor and transient amplifying cells, murine EGFP-anillin ESC clones were differentiated into embryoid bodies (EBs). The intensity of EGFP fluorescence decreased during in vitro differentiation when compared to control EBs expressing EGFP under control of the CAG promoter (FIG. 14B). At day 9 EGFP fluorescence was only evident in well defined cortical regions of EGFP-anillin EBs, suggesting mitotic activity at the rim of the EBs as confirmed by cross sections (FIG. 14C). In analogy to the analysis of undifferentiated ES cells, an investigation was undertaken on the specificity of EGFP-anillin expression in differentiating cells using anti-Ki-67 staining of plated EBs at day 16 of differentiation (FIG. 2A). There was a high overlap of EGFP-anillin fluorescence with Ki-67 staining (Table 2). Importantly, accumulation of EGFP-anillin in non-cycling, Ki-67 negative cells could be ruled out (FIG. 2A arrows, and Table 2), clearly suggesting constitutive activity of $APC^{Cdh1}$ in the post-mitotic differentiating cells. For quantitation, EBs and re-plated the cells were dissociated at low density on glass coverslips. At day 12 of differentiation approximately half of the cells were still proliferating based on Ki-67 staining and EGFP-anillin expression which was also true for plated EBs at day 16 (Table 2). The accuracy of the EGFP-anillin system was further corroborated by staining EGFP-anillin EBs for Ki-67 during the course of differentiation followed by flow cytometric analysis. This revealed a very good correlation between EGFP-anillin expressing and Ki-67 positive cell percentages. An investigation was undertaken whether the EGFP-anillin construct marked proliferating and differentiating ESC-derived cells of all three germ layers. Ki-67 positive and EGFP-anillin expressing cells of the mesodermal (α-actinin co-staining), neuroectodermal (β-Tubulin 3 co-staining) and endodermal lineage (Keratin 8 co-staining) were observed.

A goal was the identification of proliferating cardiomyocytes, which is challenging because of acytokinetic mitosis and endoreduplication. EB-derived cardiomyocytes were analyzed and it was found that EGFP-anillin was predominantly located in nuclei but also in contractile rings and in midbodies, clearly indicating the proliferation of these cells (FIG. 12B). The nuclei of all cardiomyocytes with EGFP-anillin expression were also Ki67 positive, demonstrating those cells to be in the cell cycle. Especially the presence of an EGFP-anillin positive midbody enabled the identification of cardiomyocytes that had just separated, a conclusion which cannot be drawn from Ki-67 or pHH3 stainings, which are unable to distinguish between endoreduplication/acytokinetic mitosis and cell division.

Thus, EGFP-anillin is a highly specific marker for proliferating cells in vitro that allows the accurate and easy determination of proliferating cell populations as well as subphases of M-phase. In addition, definitive proof was provided that the EGFP-anillin system labels proliferating cardiomyocytes because of the specific localization of the EGFP signal to the contractile ring and the midbody.

Example 11

A Transgenic EGFP-Anillin Mouse Line for In Vivo Visualization of Proliferation

To evaluate the feasibility of EGFP-anillin as a proliferation marker in vivo, a transgenic mouse line was generated by aggregation of EGFP-anillin ESCs from two different, individual clones with wild type tetraploid embryos (as described in Nagy et al., Proc. Natl. Acad. Sci. USA 90 (18), 9424-9428, 1993). Mice obtained by this method displayed 100% chimerism as indicated by coat colour and provided transmission to the germ line. The EGFP-anillin transgene was inherited to 50% of the offspring and the two mouse lines did display very similar transgene expression patterns. Dissection of embryos at E10.5 revealed the strongest EGFP-anillin signal in embryonic hearts (FIG. 13B, dotted square), but Signals were also found in all other tissues (FIG. 13A) such as in the neuroepithelium of the embryonic brain (FIG. 13B, arrows). Notably, accumulations of apical midbodies were detected, which were released by neuroepithelial cells into the extracellular space (FIG. 14D) as previously described (as described by Dubreuil et al., J. Cell Biol., Vol. 176, 483-495, 2007).

Staining for Ki-67 of E10.5 embryonic hearts revealed an >90% overlap with EGFP-anillin expression in atria and ventricles (FIG. 13C). Most importantly, EGFP-anillin could be observed in the contractile ring and midbody in cardiomyocytes even from late embryonic stages as E18.5 (FIG. 13D) unequivocally proving ongoing proliferation and cell division. A goal was to be able to distinguish cell division from endoreduplication and acytokinetic mitosis. A tissue that contains polyploid and diploid nuclei during embryonic development is the placenta (as described by Cross, J. C., Placenta 26 Suppl A, S3-S9, 2005). Trophoblast giant cells of the placenta are an example of massive endoreduplication as their DNA content can be as high as 1024C (as described in Zybina, E. V. and Zybina, T. G., Int. Rev. Cytol. 165, 53-119, 1996). In placentas of EGFP-anillin mice, trophoblast giant cells displayed nuclear localization of EGFP-anillin (FIG. 13E, left picture) but contractile rings or midbodies could never be observed proving DNA-synthesis without karyokinesis or cytokinesis. In contrast, in cells from the chorionic plate, EGFP-anillin was found in the nucleus, in the cytoplasm (FIG. 13E, right panel upper picture) or in midbodies (FIG. 13E, right panel lower picture) proving their cell division. These data further confirm the Utility of EGFP-anillin as an in vivo proliferation marker during embryonic development that accurately marks cells in the cell cycle and distinguishes between cell division and endoreduplication. While the $APC^{Cdh1}$ was active in postmitotic embryonic cells, the question remained whether this is also the case at postnatal and adult stages or whether unspecific accumulation of EGFP-anillin was found. An examination of mice at day 3 after birth (P3) was undertaken. Analysis of cardiac tissue revealed EGFP-anillin expression in cardiomyocytes (FIG. 13F, left panel) identified by α-actinin staining (FIG. 14E). At this stage contractile rings and midbodies as definitive proofs for cell division could still be observed (FIG. 14F, arrows). Skin of P3 mice also displayed substantial EGFP-anillin expressing cells (FIG. 13F, right panel), demonstrating postnatal growth by proliferation. At later stages EGFP fluorescence declined and in 8 weeks old mice even tissues with strong activity of the CAG promoter such as cardiac (FIG. 13F) or skeletal muscle did not show EGFP-anillin expression or accumulation (FIG. 13F) with the exception of some smooth muscle cells of intestine and urinary bladder (data not shown). Given the lack of EGFP-anillin protein in adult cardiac muscle, these mice could be an interesting model for the investigation of cardiac regeneration, myocardial infarctions were therefore induced (as described in Roell, W. et al., Transplantation 73, 462-465, 2002). A large population of EGFP-anillin expressing cells could be detected on day 4 after lesion equally distributed in the infarcted area (FIG. 13G); these cells stained also positive for Ki-67 (FIG. 14G). Staining for the cell type-specific marker α-smooth muscle actin revealed that the majority of EGFP-anillin expressing cells were myofibroblasts (FIG. 13H, arrows in upper picture). In some of these cells (8.1%) localization of EGFP-anillin in the contractile ring or the midbody was evident (FIG. 13H, arrows in lower pictures) indicating numerous cell divisions. Staining for Ki-67 in subsequent sections indicated overlap with EGFP-anillin expressing cells, although more cells were Ki-67 than EGFP-anillin positive (FIG. 14G). Approximately 5.5% of the cardiomyocytes in the border zone of the lesion expressed EGFP-anillin in the nucleus (FIG. 13I), but neither contractile rings nor midbodies could be observed suggesting re-entry into the cell cycle but no cell division. Nuclear localization of EGFP-anillin indicates increase of the DNA-content in cardiomyocytes by endoreduplication, which has been described in humans after myocardial infarction (as described in Herget, G. W. et al., Cardiovasc. Res. 36, 45-51, 1997; Meckert, P. C. et al., Cardiovasc. Res. 67, 116-123, 2005). The myocardial infarction model demonstrates the feasibility of the EGFP-anillin system for analyzing proliferation in vivo especially for therapeutic approaches in clinical relevant models exploring disease and regeneration in muscle.

Current approaches assessing proliferation in tissues with variations of the cell cycle such as heart and liver overestimate the number of dividing cells because of acytokinetic mitosis, endoreduplication and DNA repair. An elegant way to solve this problem is the direct visualization of cytokinesis and cell Separation as hallmarks of cell division. For this purpose, a fluorescent based System consisting of EGFP and anillin, a scaffolding protein of the contractile ring, which marks the different stages of the M-phase, was generated. Another critical advantage of anillin is that it is ubiquitinated by the $APC^{Cdh1}$ and completely degraded by the proteasome after every cell division and also in postmitotic cells preventing its accumulation in non proliferating cells. Recently, a System allowing detection of the cell cycle transition from G1 to S phase in live cells has been described (as described in Sakaue-Sawano et al., Cell 132, 487-498, 2008). Although this System provides a useful tool for detecting cells during specific proliferative phases at the embryonic stage, it is however not suited for the detailed analysis of M-phase and cell division. The β-actin promoter was chosen to drive the EGFP-anillin expression because of its ubiquitous and strong expression in murine and human ESCs as well as in embryonic and adult muscle tissue (as described in Okabe, M. et al., FEBS Lett. 407, 313-319, 1997). Consequently, the feasibility of this novel System was tested in murine and human ESCs and iPS cells because of its relevance for regenerative medicine and its Utility as an in vitro screening System for small molecules and factors modulating the cell cycle. The EGFP-anillin System was demonstrated to work in cells of all three germ layers derived from mouse ESCs, implying its functionality in virtually all cell types. The occurrence of EGFP-anillin negative/Ki67 positive cells is due to continuous degradation of EGFP-anillin by the $APC^{Cdh1}$ during early G1 (as described in Zhao and Fang, Journal of Biological Chemistry Vol. 280, 33516-33524, 2005). As G1-phase lasts longer in differentiating cells compared to ESCs (as described by White, J. and Dalton, S. et al., Stem Cell Rev. 1, 131-138, 2005), this population was larger (6%) in EBs than in EGFP-anillin ESC clones (2.5%). The EGFP-anillin positive/Ki67 negative cells are most likely due to staining artefacts because of formaldehyde fixation, a prerequisite for EGFP preservation, which has been reported to diminish Ki67 immunoreactivity (as described in Munakata, S, and Hendricks, J. B., J. Histochem. Cytochem. 41, 1241-1246, 1993).

Interestingly, the EGFP-anillin system also allows determining precisely the duration of early G1-phase, M-phase, karyokinesis, cytokinesis and of the overall cell cycle. Significantly shorter durations of for human ESCs (17 hours) compared to iPS cells (21 hours) were detected. The shorter cell cycle duration of human ESCs is in accordance with other reports that determined an average cell cycle duration of 15-16 hours for human (as described by Becker K. A. et al., J. Cell Physiol 209, 883-893, 2006) and 15 hours for primate ESCs (as described in Fluckiger, A. C. et al., Stem Cells 24, 547-556, 2006) whereas longer durations of 30-36 hours have been reported by (as described by White, J. and Dalton, S. et al., Stem Cell Rev. 1, 131-138, 2005). This discrepancy could be due to a period of cell cycle prolongation and adaptation after passaging, as described for primate ESCs that required 3 days of adaptation with a doubling time of 70 hours, followed by 2 days of optimal growth (as described in Fluckiger, A. C. et al., Stem Cells 24, 547-556, 2006). A similar mechanism is most likely responsible for the short cell cycle duration in human ESCs which was determined at day 4 after plating (as described by Becker K. A. et al., J. Cell Physiol 209, 883-893, 2006). The difference in the duration of the presence of the midbody in human ESCs compared to iPS cells could be due to a variation of timing of abscission and autophagocytotic degradation of the midbody as has been also proposed for other cell types (as described in Pohl, C. and Jentsch, S., Cell 132, 832-845, 2008). Future analysis of cell cycle kinetics with the EGFP-anillin system in different human ESCs and iPS cell lines could be helpful to better understand the known cell biological differences between lines and also between different types of pluripotent stem cells. The in vivo analysis of proliferation during embryonic development would open up new perspectives for studying developmental processes. For this purpose, CAG-EGFP-anillin transgenic mouse lines were generated using tetraploid complementation. This technique instead of pronuclear injection was chosen because it provided identical genetic background for comparative in vitro and in vivo studies. During embryonic development proliferating cells could be easily detected in all tissues in general and, for example, in the hearts of transgenic mice. Postmitotic cells such as β-Tubulin 3 positive neurons in the neuroepithelium did not express EGFP-anillin, clearly proving its efficient degradation by the proteasome and excluding false positives. The specificity of the EGFP-anillin was further underscored by analyzing giant trophoblast cells of the placenta, known to undergo endoreduplication. In these cells, contractile rings and midbodies were never observed in contrast to the proliferating cells in the chorionic plate. The occurrence of midbodies and contractile rings allowed to identify cells in late M-phase and to unequivocally confirm cell division. This is of utter importance for the analysis of cardiomyocytes that undergo variations of the normal cell cycle during their differentiation. For future therapeutic approaches in cardiovascular medicine aimed at manipulating the cell cycle, it is mandatory to perform an initial screening of substances in a cell culture system, followed by verification in the transgenic mouse as an in vivo system for cycling adult cardiomyocytes. In this context, the ESC system appears to be powerful for screening assays for small molecules bringing cardiomyocytes back in the cell cycle, as these cells are not yet differentiated and could be more permissive for such manipulations (as described in Kolossov, E. et al., J. Exp. Med. 203, 2315-2327, 2006). For screening of components re-inducing proliferation in cardiomyocytes double transgenic ESC lines with EGFP-anillin and another fluorophore driven by a cardiac specific promoter such as Myh6 would be useful.

Besides its use in in vitro and in vivo screening for substances with inductive or inhibitory action on proliferation, the EGFP-anillin system also provides a useful tool for in vivo monitoring of proliferation. In contrast to earlier reported models, which focused on embryonic development (as described in Sakaue-Sawano et al., Cell 132, 487-498, 2008), at postnatal day 3 EGFP-anillin expression was detected to be still preserved, but declined during later stages even in muscle tissue. It is assumed that the $APC^{Cdh1}$ is still active in these tissues as its components are detectable in postmitotic organs such as heart, liver or brain (as described in Gieffers, C et al., Proc. Natl. Acad. Sci. U.S.A 96, 11317-11322, 1999). The utility of the EGFP-anillin system was investigated under conditions of increased turnover such as tissue injury and regeneration and induced myocardial lesions in adult transgenic mice. It was demonstrated that proliferating cells can be detected using this approach after myocardial infarction in adult mice. The EGFP-anillin positive cells located in the infarct area were mainly cardiac myofibroblasts, known to proliferate after myocardial infarction (as described in Virag, J. I. and Murry, C. E., Am. J. Pathol. 163, 2433-2440, 2003). Surprisingly, EGFP-anillin positive cardiomyocytes were observed in the border zone of the infarction. However, these cells displayed exclusively nuclear localization of EGFP-anillin indicating their re-entry into cell cycle without cell division. To this end, EGFP-anillin mice are the first in vivo model for the verification of proliferation/cell division inducing strategies in cardiac tissue. Taken together the CAG-EGFP-anillin System provides an easy and reliable method for identifying proliferative cells in vitro and in vivo. Because of its high spatiotemporal resolution of the M-phase it allows to discriminate between cells that divide and that undergo DNA repair, endoreduplication or acytokinetic mitosis. Future strategies are aimed to replace the β-actin promoter by cell cycle specific promoters which could enable cell cycle analysis at all postnatal stages.

Tables

TABLE 1

Cell cycle kinetics of EGFP-anillin cells

| Event | Duration |
| --- | --- |
| Nucleus dissolving | 7 min |
| EGFP in cortex | 24 min |
| Cytokinesis | 10 min |
| Midbody visible | 57 min |
| Cell cycle duration | 13.7 hours |

TABLE 2

Quantification of EGFP-anillin expressing cells stained for Ki-67 and pHH3

| | Quantification method | | | |
| --- | --- | --- | --- | --- |
| Cell type | IF ESCs | Flow cytometry ESCs | IF EBs dl2 | IF EBs dl6 |
| EGFP-anillin+ | 97.5 | 99.0 | 47.6 | 50.7 |
| Ki-67+ | 98.3 | 99.2 | 50.6 | 51.8 |
| pHH3+ | 23.0 | 22.2 | n/d | n/d |
| Ki-67+EGFP-anillin+ | 95.8 | 98.5 | 44.6 | 47.3 |
| Ki-67+EGFP-anillm | 2.5 | 0.7 | 6 | 4.6 |
| Ki-67–EGFP-anillin+ | 1.7 | 0.5 | 3 | 3.5 |
| pHH3+EGFP-anillin+ | 23.0 | 22.0 | n/d | n/d |
| pHH3+EGFP-anillin– | 0 | 0.2 | n/d | n/d |

IF: immunofluorescence; ESCs embryonic stem cells; EBs embryoid bodies differentiation day 12 or 16

The present invention is not limited to embodiments described herein; reference should be had to the appended claims.

What is claimed is:

1. A mammalian nucleic acid expression construct which encodes a fusion protein comprising:
    a reporter protein;
    a localization protein; and
    a protein with a wild-type destruction signal;
    wherein the nucleic acid expression construct encoding the fusion protein comprises a non-endogenous promoter, the fusion protein, when expressed, localizes during a cell cycle progression to subcellular structures selected from a cell cortex, a contractile ring, and a midbody via the localization signal, the protein with a wild-type destruction signal is anillin or a functionally active fragment or derivative thereof, and the fusion protein, when expressed, is capable of being monitored via the reporter protein so as to allow a cell cycle progression in a live mammalian cell to be visualized during an interphase and an M-phase for more than one cell cycle and to distinguish between at least one of a cell division, an acytokinetic mitosis, and an endoreduplication in a live mammalian cell for more than one cell cycle.

2. The mammalian nucleic acid expression construct as recited in claim 1, wherein the reporter protein is a fluorescent protein, a luminescent protein or a beta-galactosidase.

3. The mammalian nucleic acid expression construct as recited in claim 1, wherein the anillin is a human or non-human animal anillin.

4. The mammalian nucleic acid expression construct as recited in claim 3, wherein the non-human animal anillin is a mouse anillin.

5. The mammalian nucleic acid expression construct as recited in claim 1, wherein the non-endogenous promoter is at least one of a constitutive promoter, a cell cycle-specific promoter, a cell type-specific promoter, and a cardiomyocyte-specific α-MHC promoter.

6. The mammalian nucleic acid expression construct of claim 5,
    wherein the constitutive promoter is selected from at least one of an immediate/early promoter/enhancer of a cytomegalovirus (CMV promoter), a chicken β-actin promoter, and a CMV early enhancer/chicken β-actin (CAG) promoter, or
    wherein the cell cycle-specific promoter is selected from at least one of an E2F1 promoter, a Ki-67 promoter, a PCNA promoter, and a cyclin B1 promoter.

7. A method of visualizing cell cycle progression, the method comprising:
    a) introducing the nucleic acid expression construct as recited in claim 1 into a cell;
    b) expressing the fusion protein encoded by the nucleic acid expression construct within the cell; and
    c) monitoring an expression of the fusion protein via the reporter protein.

8. The method as recited in claim 7, wherein step a) further comprises stably introducing the nucleic acid expression construct into the cell.

9. The method as recited in claim 8, wherein the nucleic acid expression construct is stably introduced into the cell by at least one of a viral transduction and a lentiviral transduction.

10. The method of claim 7, wherein the cell is a mammalian cell line.

11. The method of claim 10, wherein the mammalian cell line is selected from the group consisting of: a stem cell line, a cardiomyocyte cell line, a fibroblast cell line, a chimeric embryonic cell line, a HEK 293 cell, and a Hela cell.

12. The method of claim 11, wherein the stem cell line is selected from the group consisting of: an embryonic stem (ES) cell line, an adult stem cell line, and an induced pluripotent (iPS) cell line.

13. The method as recited in claim 7, wherein the monitoring in step c) is performed by means of a fluorescence, a luminescence or an enzymatic analysis.

14. The method as recited in claim 13, wherein the monitoring in step c) is preformed for a time period of at least one cell cycle.

* * * * *